(12) United States Patent
Agrofoglio et al.

(10) Patent No.: US 11,479,571 B2
(45) Date of Patent: Oct. 25, 2022

(54) BENZIMIDAZOL DERIVATIVES FOR TREATING FILOVIRUS INFECTION

(71) Applicants: Centre national de la recherche scientifique, Paris (FR); UNIVERSITE D'ORLEANS, Orleans (FR)

(72) Inventors: Luigi Agrofoglio, Orleans (FR); Vincent Roy, Outarville (FR); Elzbieta Plebanek, Orleans (FR); Maxime Bessieres, Les Loges (FR)

(73) Assignees: CENTRE NATIONAL DE LA RECHERCHE SCIENTIFIQUE, Paris (FR); UNIVERSITE D'ORLEANS, Orleans (FR)

( * ) Notice: Subject to any disclaimer, the term of this patent is extended or adjusted under 35 U.S.C. 154(b) by 669 days.

(21) Appl. No.: 16/332,666

(22) PCT Filed: Sep. 14, 2017

(86) PCT No.: PCT/EP2017/073185
§ 371 (c)(1),
(2) Date: Mar. 12, 2019

(87) PCT Pub. No.: WO2018/050771
PCT Pub. Date: Mar. 22, 2018

(65) Prior Publication Data
US 2021/0292350 A1    Sep. 23, 2021

(30) Foreign Application Priority Data

Sep. 15, 2016 (EP) ..................... 16306177

(51) Int. Cl.
*C07D 235/04* (2006.01)
*C07F 9/6558* (2006.01)
*A61P 31/14* (2006.01)
*C07D 235/06* (2006.01)
*C07D 401/04* (2006.01)

(52) U.S. Cl.
CPC .......... *C07F 9/65583* (2013.01); *A61P 31/14* (2018.01); *C07D 235/06* (2013.01); *C07D 401/04* (2013.01)

(58) Field of Classification Search
CPC .................................... C07D 235/04
See application file for complete search history.

(56) References Cited

FOREIGN PATENT DOCUMENTS

| FR | 2831537 | 5/2003 | |
|----|---------|--------|----|
| JP | 2004067629 | 3/2004 | |
| WO | WO-2014141015 A1 * | 9/2014 | ............ A61P 35/00 |

OTHER PUBLICATIONS

International Search Report for PCT/EP2017/073185, dated Oct. 20, 2017.
Written Opinion of the International Searching Authority for PCT/EP2017/073185, dated Oct. 20, 2017.

* cited by examiner

*Primary Examiner* — John S Kenyon
(74) *Attorney, Agent, or Firm* — B. Aaron Schulman, Esq.; Stites & Harbison, PLLC

(57) ABSTRACT

The present invention relates to compounds comprising a benzimidazole scaffold, and the use of such compounds for the treatment of viral diseases. The invention also relates to pharmaceutical compositions comprising said compounds as an active ingredient. In particular the compounds of the invention comprising a benzimidazole scaffold are used for the treatment of filoviruses or retroviruses, and preferably for the treatment of Ebola virus or HIV virus.

19 Claims, No Drawings

BENZIMIDAZOL DERIVATIVES FOR TREATING FILOVIRUS INFECTION

The present invention relates to compounds comprising a benzimidazole scaffold, and the use of such compounds for the treatment of viral diseases. The invention also relates to pharmaceutical compositions comprising said compounds as active ingredient.

In particular the compounds of the invention comprising a benzimidazole scaffold are used for the treatment of filoviruses or retroviruses, and preferably for the treatment of Ebola virus or HIV virus.

Viruses can infect all types of life forms, from bacteria to human beings. In humans, problems appear when the immune system cannot destroy the virus, and it brings a disease. There is a large number of identified viruses, being pathogenic for humans. Depending on the type of virus they can easily and rapidly spread through organisms and cause a problem of public health. Some of them are difficult to control and over the years of human history they caused epidemics with many fatalities as the Spanish flu in 1918 with about 30 million deaths, polio in the 30s, the herpes virus in the 60s, AIDS since the 80s, and more recently Ebola virus. Until the 1960s the strategy to fight viral infections was largely based on vaccination. However over the last fifty years the researchers focused on developing small molecules which selectively interfere with one or more biological processes participating in virus life cycle.

Thus, there is a need to develop new molecules to interfere with viruses and fight against viral diseases. Indeed, for filoviruses for instance, the unpredictable onset, simplicity of transmission, fast progression of disease, high fatality make difficult to produce an efficient treatment. Thus, the developing of specific treatment is necessary. Specifically, the developing of specific treatment for disease linked to filoviruses is necessary.

Ebola virus is a RNA-virus belonging to the filovirus family. Different ways to fight the virus are known and possible, such as blocking the virus at the entry of the host cell or blocking the replication of the virus as well as host immune responses. To date, there is no vaccine available or approved antiviral for use against Ebola virus. Nevertheless, new compounds are widely studied. In particular, molecules have been synthesized aiming to inhibit Ebola virus blocking its entry into the host cell.

Côté et al. identified a benzylpiperazine adamantane-derived compound as effective inhibitor of Ebola virus entry (Côté, M.; Misasi, J. Small molecule inhibitors reveal NPC1 is essential for Ebola virus infection. *Nature* 2011, 477, 344-348). However, these compounds have some limitations; the most important limiting pharmacokinetic parameter is the short biological half-life.

Basu et al. reported that the benzodiazepine derivatives are specific inhibitors of EBOV entry (Basu, A.; Li, B., Identification of a small-molecule entry inhibitor for Filoviruses. *J. Virol.* 2011, 85, 3106-3119). However, these molecules are very specific to Ebola virus and present a very weak activity against other viruses.

Thus, there is a need to develop new molecules especially showing an Ebola virus inhibition activity, but also an inhibition against other filoviruses, or retroviruses, or other diseases or pathologies.

The present invention relates to a compound of formula (I)

in which:
X represents:
  a C=O group;
  an alkyl group, linear or branched, comprising 1 to 6 carbon atoms; or
  a group of formula —NR—($C_1$-$C_6$)alkyl-, the alkyl being linear or branched;
Y represents CH or nitrogen atom;
$R^1$ represents:
  an aryl group, comprising 6 to 10 carbon atoms, non-substituted or substituted by at least one group chosen among: haloalkyl, haloalkoxyl, alkyl or alkoxyl group, the alkyl being linear or branched, and comprising 1 to 6 carbon atoms;
  an heteroaryl group, comprising 5 to 10 members, non-substituted or substituted by at least one group chosen among: haloalkyl, haloalkoxyl, alkyl or alkoxyl group, the alkyl being linear or branched, and comprising 1 to 6 carbon atoms;
  a CH-(aryl)$_2$ group, the aryl comprising 6 to 10 carbon atoms, non-substituted or substituted by at least one group chosen among: haloalkyl, haloalkoxyl, alkyl or alkoxyl group, the alkyl being linear or branched, and comprising 1 to 6 carbon atoms; or
  a CH-(heteroaryl)$_2$ group, the heteroaryl comprising 5 to 10 members, non-substituted or substituted by at least one group chosen among: haloalkyl, haloalkoxyl, alkyl or alkoxyl group, the alkyl being linear or branched, and comprising 1 to 6 carbon atoms;
$R^2$ represents:
  a ($C_1$-$C_6$)alkyl-aryl-$R^3$ group, the aryl comprising 6 to 10 carbon atoms and the alkyl being linear or branched;
  a C(O)N(R)-aryl-$R^5$ group, the aryl comprising between 6 to 10 carbon atoms;
  a C(O)—($C_1$-$C_6$)alkyl-O-aryl-Hal group, with Hal represents an halogen, the aryl comprising between 6 and 10 carbon atoms and the alkyl being linear or branched;
  a C(O)O—($C_1$-$C_6$)alkyl-aryl group, the aryl comprising between 6 to 10 carbon atoms and the alkyl being linear or branched; or
  a O-aryl-$R^3$ group, the aryl comprising between 6 to 10 carbon atoms;
$R^3$ represents a $OR^4$ group, haloalkyl or haloakoxyl, wherein the alkyl is linear or branched, and comprises 1 to 6 carbon atoms;
$R^4$ represents a ($C_1$-$C_6$)alkyl-aryl-COOR group, a haloalkyl group or a ($C_1$-$C_6$)alkyl-aryl-($C_1$-$C_6$)alkyl-PO(OR)$_2$ group, wherein alkyl is linear or branched and comprises 1 to 6 carbon atoms and the aryl comprises between 6 and 10 carbon atoms;
$R^5$ represents an alkyl group, linear or branched, comprising 1 to 6 carbon atoms; or a haloalkyl, linear or branched, comprising 1 to 6 carbon atoms;
R represents an alkyl group, linear or branched, comprising 1 to 6 carbon atoms, or a hydrogen atom;

or their pharmaceutically acceptable salts, hydrates, solvates, esters or their optical isomers, racemates, diastereoisomers, enantiomers, tautomers, or a mixture thereof.

In one embodiment, the present invention relates to a compound of formula (I) in which:

X represents:
- a C=O group;
- an alkyl group, linear or branched, comprising 1 to 6 carbon atoms; or
- a group of formula —NR—($C_1$-$C_6$)alkyl-, the alkyl being linear or branched;

Y represents CH or nitrogen atom;

$R^1$ represents:
- an aryl group, comprising 6 to 10 carbon atoms, non-substituted or substituted by at least one group chosen among: haloalkyl, haloalkoxyl, alkyl or alkoxyl group, the alkyl being linear or branched, and comprising 1 to 6 carbon atoms;
- an heteroaryl group, comprising 5 to 10 members, non-substituted or substituted by at least one group chosen among: haloalkyl, haloalkoxyl, alkyl or alkoxyl group, the alkyl being linear or branched, and comprising 1 to 6 carbon atoms;
- a CH-(aryl)$_2$ group, the aryl comprising 6 to 10 carbon atoms, non-substituted or substituted by at least one group chosen among: haloalkyl, haloalkoxyl, alkyl or alkoxyl group, the alkyl being linear or branched, and comprising 1 to 6 carbon atoms; or
- a CH-(heteroaryl)$_2$ group, the heteroaryl comprising 5 to 10 members, non-substituted or substituted by at least one group chosen among: haloalkyl, haloalkoxyl, alkyl or alkoxyl group, the alkyl being linear or branched, and comprising 1 to 6 carbon atoms;

$R^2$ represents:
- a ($C_1$-$C_6$)alkyl-aryl-$R^3$ group, the aryl comprising 6 to 10 carbon atoms and the alkyl being linear or branched;
- a C(O)N(R)-aryl-$R^5$ group, the aryl comprising between 6 to 10 carbon atoms; or
- a C(O)—($C_1$-$C_6$)alkyl-O-aryl-Hal group, with Hal represents an halogen, the aryl comprising between 6 and 10 carbon atoms and the alkyl being linear or branched;

$R^3$ represents a $OR^4$ group, haloalkyl or haloakoxyl, wherein the alkyl is linear or branched, and comprises 1 to 6 carbon atoms;

$R^4$ represents a ($C_1$-$C_6$)alkyl-aryl-COOR group, a haloalkyl group or a ($C_1$-$C_6$)alkyl-aryl-($C_1$-$C_6$)alkyl-PO(OR)$_2$ group, wherein alkyl is linear or branched and comprises 1 to 6 carbon atoms and the aryl comprises between 6 and 10 carbon atoms;

$R^5$ represents an alkyl group, linear or branched, comprising 1 to 6 carbon atoms; or a haloalkyl, linear or branched, comprising 1 to 6 carbon atoms;

R represents an alkyl group, linear or branched, comprising 1 to 6 carbon atoms, or a hydrogen atom;

or their pharmaceutically acceptable salts, hydrates, solvates, esters or their optical isomers, racemates, diastereoisomers, enantiomers, tautomers, or a mixture thereof.

Preferably, in the compound of formula (I), $R^1$ is chosen among:
- a phenyl group, non-substituted or substituted by at least one group chosen among: haloalkyl, haloalkoxyl, alkyl or alkoxyl group, the alkyl being linear or branched, and comprising 1 to 6 carbon atoms;
- a pyridine group non-substituted or substituted by at least one group chosen among: haloalkyl, haloalkoxyl, alkyl or alkoxyl group, the alkyl being linear or branched, and comprising 1 to 6 carbon atoms;
- a pyrimidine group, non-substituted or substituted by at least one group chosen among: haloalkyl, haloalkoxyl, alkyl or alkoxyl group, the alkyl being linear or branched, and comprising 1 to 6 carbon atoms; or
- a benzhydryl group non-substituted or substituted by at least one group chosen among: haloalkyl, haloalkoxyl, alkyl or alkoxyl group, the alkyl being linear or branched, and comprising 1 to 6 carbon atoms.

Preferably, in the compound of formula (I), $R^1$ is chosen among:
- a phenyl group non-substituted or substituted by at least one group chosen among: fluoroalkyl, fluoroalkoxyl, alkyl or alcoxyl group, the alkyl being linear or branched, and comprising 1 to 6 carbon atoms;
- a pyridine group non-substituted or substituted by at least one group chosen among: haloalkyl, haloalkoxyl, alkyl or alkoxyl group, the alkyl being linear or branched, and comprising 1 to 6 carbon atoms; or
- a benzhydryl group non-substituted or substituted by at least one group chosen among: fluoroalkyl, fluoroalkoxyl, alkyl or alcoxyl group, the alkyl being linear or branched, and comprising 1 to 6 carbon atoms.

Preferably, in the compound of formula (I), X represents:
- a (C=O) group; or
- an alkyl group, linear or branched, comprising 1 to 3 carbon atoms.

Preferably, in the compound of formula (I), Y represents a CH group. In another preferred embodiment of the invention, Y preferably represents a nitrogen atom.

Preferably, in the compound of formula (I), $R^1$ is chosen among:
- a phenyl group, non-substituted or substituted by at least one group chosen among: haloalkyl, haloalkoxyl, alkyl or alkoxyl group, the alkyl being linear or branched, and comprising 1 to 6 carbon atoms;
- a pyridine group non-substituted or substituted by at least one group chosen among: haloalkyl, haloalkoxyl, alkyl or alkoxyl group, the alkyl being linear or branched, and comprising 1 to 6 carbon atoms;
- a pyrimidine group, non-substituted or substituted by at least one group chosen among: haloalkyl, haloalkoxyl, alkyl or alkoxyl group, the alkyl being linear or branched, and comprising 1 to 6 carbon atoms; or
- a benzhydryl group non-substituted or substituted by at least one group chosen among: haloalkyl, haloalkoxyl, alkyl or alkoxyl group, the alkyl being linear or branched, and comprising 1 to 6 carbon atoms;

and X represents:
- a (C=O) group; or
- an alkyl group, linear or branched, comprising 1 to 3 carbon atoms.

Preferably, in the compound of formula (I), $R^1$ is chosen among:
- a phenyl group, non-substituted or substituted by at least one group chosen among: haloalkyl, haloalkoxyl, alkyl or alkoxyl group, the alkyl being linear or branched, and comprising 1 to 6 carbon atoms;
- a pyridine group non-substituted or substituted by at least one group chosen among: haloalkyl, haloalkoxyl, alkyl or alkoxyl group, the alkyl being linear or branched, and comprising 1 to 6 carbon atoms;
- a pyrimidine group, non-substituted or substituted by at least one group chosen among: haloalkyl, haloalkoxyl, alkyl or alkoxyl group, the alkyl being linear or branched, and comprising 1 to 6 carbon atoms; or
a benzhydryl group non-substituted or substituted by at least one group chosen among: haloalkyl, haloalkoxyl, alkyl or alkoxyl group, the alkyl being linear or branched, and comprising 1 to 6 carbon atoms;
and Y represents a CH group.

Preferably, in the compound of formula (I), $R^1$ is chosen among:
a phenyl group, non-substituted or substituted by at least one group chosen among: haloalkyl, haloalkoxyl, alkyl or alkoxyl group, the alkyl being linear or branched, and comprising 1 to 6 carbon atoms;
a pyridine group non-substituted or substituted by at least one group chosen among: haloalkyl, haloalkoxyl, alkyl or alkoxyl group, the alkyl being linear or branched, and comprising 1 to 6 carbon atoms;
a pyrimidine group, non-substituted or substituted by at least one group chosen among: haloalkyl, haloalkoxyl, alkyl or alkoxyl group, the alkyl being linear or branched, and comprising 1 to 6 carbon atoms; or
a benzhydryl group non-substituted or substituted by at least one group chosen among: haloalkyl, haloalkoxyl, alkyl or alkoxyl group, the alkyl being linear or branched, and comprising 1 to 6 carbon atoms;
and Y represents a nitrogen atom.

Preferably, in the compound of formula (I), X represents:
a (C=O) group; or
an alkyl group, linear or branched, comprising 1 to 3 carbon atoms;
and Y represents a CH group.

Preferably, in the compound of formula (I), X represents:
a (C=O) group; or
an alkyl group, linear or branched, comprising 1 to 3 carbon atoms;
and Y represents a nitrogen atom.

Preferably, in the compound of formula (I), $R^1$ is chosen among:
a phenyl group, non-substituted or substituted by at least one group chosen among: haloalkyl, haloalkoxyl, alkyl or alkoxyl group, the alkyl being linear or branched, and comprising 1 to 6 carbon atoms;
a pyridine group non-substituted or substituted by at least one group chosen among: haloalkyl, haloalkoxyl, alkyl or alkoxyl group, the alkyl being linear or branched, and comprising 1 to 6 carbon atoms;
a pyrimidine group, non-substituted or substituted by at least one group chosen among: haloalkyl, haloalkoxyl, alkyl or alkoxyl group, the alkyl being linear or branched, and comprising 1 to 6 carbon atoms; or
a benzhydryl group non-substituted or substituted by at least one group chosen among: haloalkyl, haloalkoxyl, alkyl or alkoxyl group, the alkyl being linear or branched, and comprising 1 to 6 carbon atoms.
and X represents:
a (C=O) group; or
an alkyl group, linear or branched, comprising 1 to 3 carbon atoms;
and Y represents a CH group.

Preferably, in the compound of formula (I), $R^1$ is chosen among:
a phenyl group, non-substituted or substituted by at least one group chosen among: haloalkyl, haloalkoxyl, alkyl or alkoxyl group, the alkyl being linear or branched, and comprising 1 to 6 carbon atoms;
a pyridine group non-substituted or substituted by at least one group chosen among: haloalkyl, haloalkoxyl, alkyl or alkoxyl group, the alkyl being linear or branched, and comprising 1 to 6 carbon atoms;
a pyrimidine group, non-substituted or substituted by at least one group chosen among: haloalkyl, haloalkoxyl, alkyl or alkoxyl group, the alkyl being linear or branched, and comprising 1 to 6 carbon atoms; or
a benzhydryl group non-substituted or substituted by at least one group chosen among: haloalkyl, haloalkoxyl, alkyl or alkoxyl group, the alkyl being linear or branched, and comprising 1 to 6 carbon atoms.
and X represents:
a (C=O) group; or
an alkyl group, linear or branched, comprising 1 to 3 carbon atoms;
and Y represents a nitrogen group.

As used hereabove or hereafter:
"Alkyl" means an aliphatic hydrocarbon group which may be straight or branched having 1 to 6 carbon atoms in the chain. "Branched" means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl.

"Alkoxyl" means an O-alkyl group, the alkyl group being as described above.

"Alken" or "alkenyl" means an aliphatic hydrocarbon group containing a carbon-carbon double bond and which may be straight or branched having 2 to 6 carbon atoms in the chain. Preferred alkenyl groups have 2 to 6 carbon atoms in the chain; and more preferably about 2 to 4 carbon atoms in the chain. Exemplary alkenyl groups include ethenyl, propenyl, n-butenyl, i-butenyl, 3-methylbut-2-enyl, n-pentenyl.

"Aryl" means an aromatic monocyclic or multicyclic hydrocarbon ring system of 6 to 14 carbon atoms, preferably of 6 to 10 carbon atoms, substituted or not. Exemplary aryl groups include phenyl or naphthyl.

"Halogen atom" refers to fluorine, chlorine, bromine or iodine atom; preferably fluorine atom.

"Haloalkyl" refers to an alkyl group as described above substituted by at least one halogen atom as described above, for example substituted by 1 to 6 halogen atoms, preferably by 1 to 3 halogen atoms. Exemplary haloalkyl group includes trifluoromethyl group.

"Haloalkoxyl" refers to an alkoxyl group as described above substituted by at least one halogen atom as described above, for example substituted by 1 to 6 halogen atoms, preferably by 1 to 3 halogen atoms, for example —$OCF_3$.

As used herein, the term "heteroaryl" refers to a 5 to 14, preferably 5 to 10-membered aromatic hetero, mono-, bi- or multicyclic ring comprising at least one heteroatom preferably chosen among: O, N or S, preferably from 1 to 5 heteroatoms, for example from 1 to 4 heteroatoms, especially one, two or three heteroatoms. Examples include pyrrolyl, pyridyl, pyrazolyl, thienyl, pyrimidinyl, pyrazinyl, tetrazolyl, indolyl, quinolinyl, purinyl, imidazolyl, thienyl, thiazolyl, benzothiazolyl, furanyl, benzofuranyl, 1,2,4-thiadiazolyl, isothiazolyl, triazoyl, tetrazolyl, isoquinolyl, benzothienyl, isobenzofuryl, pyrazolyl, carbazolyl, benzimidazolyl, isoxazolyl, pyridyl-N-oxide, as well as the fused systems resulting from the condensation with a phenyl group.

"Alkyl", "aryl", "alkoxyl", "haloalkoxyl", "haloalkyl", "heteroaryl" and the likes refers also to the corresponding "alkylene", "arylene", "alkoxylene", "haloalkoxylene", "haloalkylene" "heteroarylene" and the likes which are formed by the removal of two hydrogen atoms. Alkyl and alkylene are used herein interchangeably.

As used herein, the expression "pharmaceutically acceptable" refers to those compounds, materials, excipients, compositions or dosage forms which are, within the scope of sound medical judgment, suitable for contact with the tissues of human beings and animals without excessive toxicity, irritation, allergic response or other problem complications commensurate with a reasonable benefit/risk ratio.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like, including mono, di or tri-salts thereof; and the salts prepared from organic acids such as acetic, propionic, succinic, tartaric, citric, methanesulfonic, benzenesulfonic, glucoronic, glutamic, benzoic, salicylic, toluenesulfonic, oxalic, fumaric, maleic, lactic and the like. Further addition salts include ammonium salts such as tromethamine, meglumine, epolamine, etc., metal salts such as sodium, potassium, calcium, zinc or magnesium.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences*, 20$^{th}$ ed., Mack Publishing Company, Easton, Pa., 2000, the disclosure of which is hereby incorporated by reference.

The compounds of the general formula (I) having geometrical and stereoisomers are also a part of the invention.

The compounds of the present invention may be prepared in a number of ways well-known to those skilled in the art. The compounds can be synthesized, for example, by application or adaptation of the methods known by the skilled person. The appropriate modifications and substitutions will be readily apparent and well known or readily obtainable from the scientific literature to those skilled in the art.

It will be appreciated that the compounds of the present invention may contain one or more asymmetrically substituted carbon atoms, and may be isolated in optically active or racemic forms. Thus, all chiral, diastereomeric, racemic forms, isomeric forms of a structure are intended, unless the specific stereochemistry or isomeric form is specifically indicated. It is well-known in the art how to prepare and isolate such optically active forms. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes as shown in the examples, which can be adapted by the skilled person based on its knowledge with regards to the desired compounds.

The present invention also relates to pharmaceutical compositions comprising at least one compound of formula (I) as active principle. Preferably, the present invention also relates to pharmaceutical compositions comprising at least one compound of formula (I) as active principle and at least one excipient pharmaceutically acceptable.

According to the invention, the terms "patient" or "patient in need thereof", are intended for an animal such as a valuable animal for breeding, company or preservation purposes, or a human or a human child, being affected or likely to be affected with one or more diseases and conditions described herein. Preferably, the patient is human.

The identification of those subjects who are in need of treatment of herein-described diseases and conditions is well within the ability and knowledge of one skilled in the art. A veterinarian or a physician skilled in the art can readily identify, by the use of clinical tests, physical examination, medical/family history or biological and diagnostic tests, those subjects who are in need of such treatment.

As used herein, a "therapeutically effective amount" refers to an amount of a compound of the present invention which is effective in preventing, reducing, eliminating, treating or controlling the symptoms of the herein-described diseases and conditions. The term "controlling" is intended to refer to all processes wherein there may be a slowing, interrupting, arresting, or stopping of the progression of the diseases and conditions described herein, but does not necessarily indicate a total elimination of all disease and condition symptoms, and is intended to include prophylactic treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a compound of formula (I), which is required to achieve the desired biological effect, will vary depending upon a number of factors, including the chemical characteristics of the compounds employed, the potency of the compounds, the type of disease, the species to which the patient belongs, the diseased state of the patient, the route of administration, the bioavailability of the compound by the chosen route, all factors which dictate the required dose amounts, delivery and regimen to be administered.

As used herein, "pharmaceutically acceptable excipient" includes any carriers, diluents, adjuvants, or vehicles, such as preserving or antioxidant agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well-known in the art. Except insofar as any conventional media or agent is incompatible with the active ingredient, its use in the therapeutic compositions is contemplated. Supplementary active ingredients can also be incorporated into the compositions as suitable therapeutic combinations.

In the context of the invention, the term "treating" or "treatment", as used herein, means reversing, alleviating, inhibiting the progress of, or preventing the disorder or condition to which such term applies, or one or more symptoms of such disorder or condition.

The preferred dosage of drug to be administered is likely to depend on such variables as the type and extent of progression of the disease or disorder, the overall health status of the particular patient, the relative biological efficacy of the compound selected, the formulation of the compound, the route of administration (intravenous, intramuscular, or other), the pharmacokinetic properties of the compound by the chosen delivery route, and the speed (bolus or continuous infusion) and schedule of administrations (number of repetitions in a given period of time).

The compound of formula (I) of the present invention is also capable of being administered in unit dose forms, wherein the expression "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. Compounds provided herein can be formulated into pharmaceutical compositions by admixture with one or more pharmaceutically acceptable excipients. Such unit dose compositions may be prepared for use by oral administration, particularly in the form of tablets, simple capsules or soft gel capsules; or intranasally, particularly in the form of powders, nasal drops, or aerosols; or dermally, for example, topically in ointments, creams, lotions, gels or sprays, or via trans-dermal patches.

The compositions may conveniently be administered in unit dosage form and may be prepared by any of the methods well-known in the pharmaceutical art.

For oral administration, tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolved, modified-release or sustained-release preparations and formulations, and wherein such sustained-release formulations are preferably bi-modal. Preferred tablets contain lactose, cornstarch, magnesium silicate, croscarmellose sodium, povidone, magnesium stearate, or talc in any combination.

Liquid preparations for parenteral administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

The present invention also relates to at least one compound of formula (I) of the invention, or to the composition of the invention for use for the treatment of viral diseases.

In the present invention "compound X for the treatment of Y" is equivalent to "compound X for use in a method for the treatment of Y" or "compound X for use in the therapy of Y".

The present invention also relates to the use of at least one compound of formula (I) of the invention or of the composition of the invention for the preparation of a medicine for the treatment of viral diseases.

The present invention also relates to a method of treatment of viral diseases comprising the administration of a therapeutically effective amount of at least one compound of formula (I) of the invention or of the composition of the invention to a patient in need thereof.

The present invention also relates to at least one compound of formula (I) of the invention or to the composition of the invention for use for the treatment of infections with a filovirus. Preferably, the invention relates to at least one compound of formula (I) of the invention or to the composition of the invention for use for the treatment of infections with Ebola virus.

The present invention also relates to the use of at least one compound of formula (I) of the invention or of the composition of the invention for the preparation of a medicine for the treatment of infections with filovirus. Preferably, the invention relates to the use of at least one compound of formula (I) of the invention or of the composition of the invention for the preparation of a medicine for the treatment of infections with Ebola virus.

The present invention also relates to a method of treatment of infections with a filovirus comprising the administration of a therapeutically effective amount of at least one compound of formula (I) of the invention or of the composition of the invention to a patient in the need thereof. Preferably, the invention relates to a method of treatment of infections with Ebola virus comprising the administration of a therapeutically effective amount of at least one compound of formula (I) of the invention or of the composition of the invention to a patient in the need thereof.

The present invention also relates to at least one compound of formula (I) of the invention for use for the treatment of infections with a retrovirus. Preferably, the invention relates to at least one compound of formula (I) of the invention or of the composition of the invention for use for the treatment of infections with Human Immunodeficiency Virus (HIV).

The present invention also relates to the use of at least one compound of formula (I) of the invention or of the composition of the invention for the preparation of a medicine for the treatment of infections with a retrovirus. Preferably, the invention relates to the use of at least one compound of formula (I) of the invention or of the composition of the invention for the preparation of a medicine the treatment of infections with Human Immunodeficiency Virus (HIV).

The present invention also relates to a method of treatment of infections with a retrovirus comprising the administration of a therapeutically effective amount of at least one compound of formula (I) of the invention or of the composition of the invention to a patient in the need thereof. Preferably, the invention relates to a method of treatment of infections with Human Immunodeficiency Virus (HIV) comprising the administration of a therapeutically effective amount of at least one compound of formula (I) of the invention or of the composition of the invention to a patient in the need thereof.

The present invention also relates to at least a compound of formula (I) of the invention or of the composition of the invention for use for the treatment of pathologies such as cholesterol, metabolic disorders, obesity, AIDS, and some congenital and genetic diseases such as Niemann-Pick disease type C1.

The present invention also relates to the use of at least one compound of formula (I) of the invention or of the composition of the invention for the preparation of a medicine for the treatment of pathologies such as cholesterol, metabolic disorders, obesity, AIDS, and some congenital and genetic diseases such as Niemann-Pick disease type C1.

The present invention also relates to a method of treatment of pathologies such as cholesterol, metabolic disorders, obesity, AIDS, and some congenital and genetic diseases such as Niemann-Pick disease type C1 comprising the administration of a therapeutically effective amount of at least one compound of formula (I) of the invention or of the composition of the invention to a patient in the need thereof.

The present invention will now be described with the help of non-limitative examples.

EXAMPLES

Commercially available chemicals were of reagent grade and used as received. All reactions requiring anhydrous conditions were carried out using oven-dried glassware and under an atmosphere of dry Ar or $N_2$. Microwave reactions were carried out in a Biotage Initiator apparatus. The reactions under ultrasound were carried out with Elmasonic P30H apparatus with a frequency of 80 kHz and effective power of 100 W. The reactions were monitored by thin layer chromatography (TLC) analysis using silica gel precoated plates (Kieselgel 60F254, E. Merck). Compounds were visualized by UV irradiation and/or spraying with phosphomolybdic acid (PMA) stain, potassium permanganate solution or ninhydrin stain, followed by charring at around 150° C. Flash column chromatography was performed on Silica Gel 60 M (0.040-0.063 mm, E. Merck). The infrared spectra were measured with Perkin-Elmer Spectrometer. The $^1H$ and $^{13}C$ NMR spectra were recorded on Bruker Avance DPX 250 or Bruker Avance 400 Spectrometers. Chemical shifts are given in ppm and are referenced to the deuterated solvent signal or to TMS as internal standard and multiplicities are reported as s (singlet), d (doublet), t (triplet), q (quartet) and m (multiplet). Carbon multiplicities were assigned by distortionless enhancement by polarization transfer (DEPT) experiments. $^1H$ and $^{13}C$ signals were attributed on the basis of H—H and H—C correlations. High Resolution Mass spectra were performed on a Bruker Q-TOF MaXis spectrometer.

General Procedures:

Compounds of the invention have been synthesized following 10 general procedures, described as follow:

General Procedure 1:

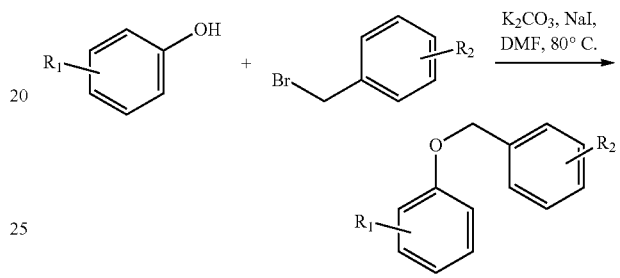

A microwave vial was charged with bromomethylbenzene derivative (0.4 mmol, 1 equiv), appropriated phenol derivative (0.44 mmol, 1.1 equiv), $K_2CO_3$ (0.8 mmol, 2 equiv), few crystals of NaI and dimethylformamide (DMF) (1.4 mL). The reaction mixture was heated under microwave irradiation at 80° C. for 10 minutes. Then, resulted mixture was poured into water and extracted with ethyl acetate. Combined organic phases were washed with brine, dried over $MgSO_4$ and concentrated under vacuum. The residue was purified by column chromatography on silica gel ($CH_2Cl_2$/MeOH).

General Procedure 2:

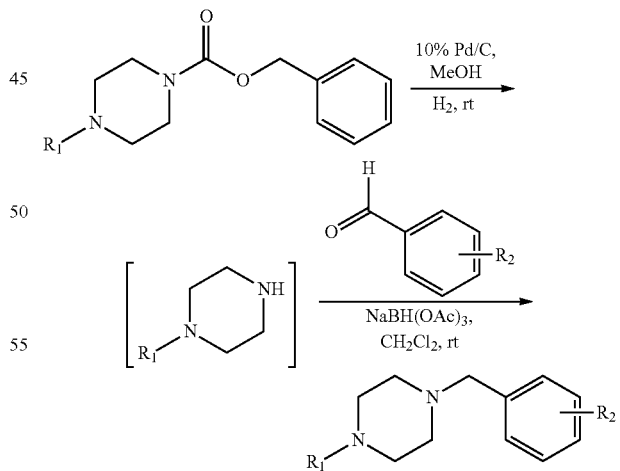

To a solution of piperazine-Cbz derivative (1 equiv) in MeOH (1.6 mL) palladium on carbon (0.02 g, 0.19 mmol, 1.2 eq) was added and mixture was stirred under hydrogen atmosphere overnight at room temperature. Then, palladium catalyst was filtered off. The filtrate was concentrated and dissolved in $CH_2Cl_2$ (3 mL). To the obtained solution were added aldehyde derivative (1 equiv) and sodium triacetoxyborohydride (0.04 g, 0.19 mmol, 1.2 equiv). The reaction mixture was stirred at room temperature till the completion (~20 h), then after addition of water, the solution was extracted with ethyl acetate. The combined organic phases were washed with brine, dried over MgSO₄ and concentrated. The crude was purified by column chromatography (CH₂Cl₂/MeOH).

General Procedure 3:

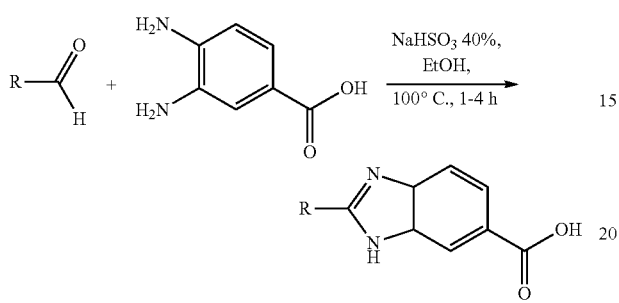

A solution of aldehyde (1 equiv) in 40% NaHSO₃ (2 mL) was stirred for 1 h at room temperature. Then a solution of 3,4-diaminobenzoic acid (0.30 g, 1.97 mmol, 1 equiv) in ethanol (1 mL) was added. Reaction mixture was stirred at 100° C. for 1-4 h, and then concentrated. Residue was dissolved in water, and then the obtained mixture was acidified to pH 3-4 by adding HCl. The resulting precipitate was collected by filtration to give desired product.

General Procedure 4:

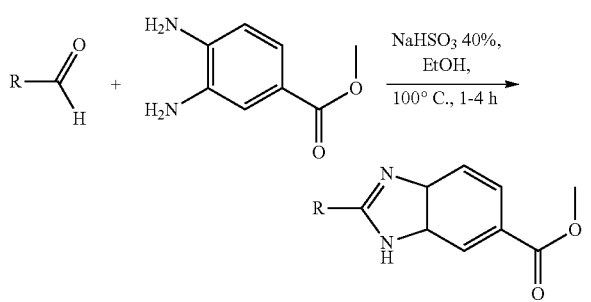

A solution of aldehyde (1 equiv) in 40% NaHSO₃ (4 mL) was stirred for 1 h at room temperature, then a solution of methyl 3,4-diaminobenzoate (0.65 g, 3.94 mmol, 1 equiv) in ethanol (2 mL) was added. The resulting mixture was stirred at 100° C. for 1-4 h, and then concentrated. The residue was dissolved in water and extracted with ethyl acetate. The combined organic phases were dried over MgSO₄ and concentrated. The crude product was purified by flash column chromatography (PE/EtOAc or CH₂Cl₂/MeOH) to afford desired product.

General Procedure 5:

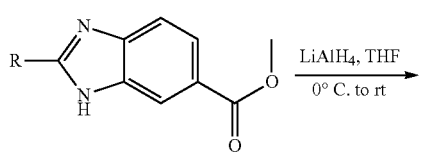

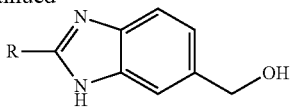

To a mixture of LiAlH₄ (0.03 g, 0.8 mmol, 2 equiv) in dry tetrahydrofuran (THF) (1 mL), cooled at 0° C., a solution of methyl 2-substituted-benzimidazole-5 carboxylate (1 equiv) in dry THF (1 mL) was slowly added. The ice bath was removed and the reaction mixture was stirred for 2-4 h. After completion ethyl acetate and water were added. Then, the aqueous phase was extracted with ethyl acetate (3×) and the combined organic phases were dried over MgSO₄ and concentrated to give the desired product.

General Procedure 6:

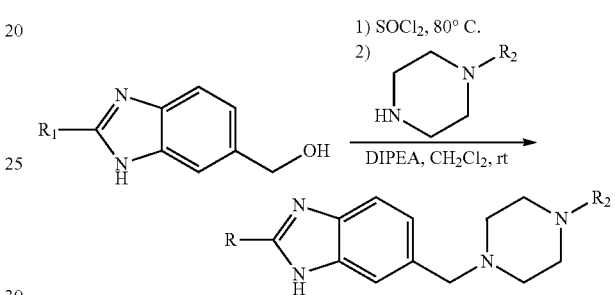

To a flask with hydroxymethyl benzimidazole derivative (1 equiv) SOCl₂ (0.84 mL, 11.6 mmol, 29 equiv) was added and the resulted mixture was stirred for 2 h30 min at 80° C. After cooling to room temperature, SOCl₂ was evaporated and the obtained solid was diluted with CH₂Cl₂ (4 mL) and cooled to 0° C. Then, to the obtained solution piperazine derivative (1 equiv) and diisopropylethylamine (0.37 mL, 2.12 mmol, 5.3 equiv) were added. The ice bath was removed and the reaction mixture was stirred for 16-19 h at room temperature. Then, the reaction mixture was washed with water (4×), brine and dried over MgSO₄. After concentration, the crude product was purified by column chromatography (CH₂Cl₂/MeOH) to give the desired product.

General Procedure 7:

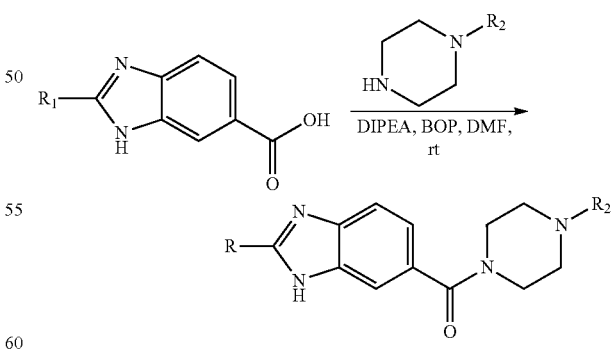

To a mixture of piperazine derivative (1.1 equiv) and benzimidazole-carboxylic acid derivative (1 equiv) in DMF (1 mL), (benzotriazol-1-yloxy)tris(dimethylamino)phosphonium hexafluorophosphate (BOP) (0.24 g, 0.55 mmol, 1.3 equiv) and diisopropylethylamine (0.22 mL, 1.26 mmol, 3 equiv) were added. The reaction mixture was stirred at room temperature for 16 h then NaCl$_{sat}$ was added. The aqueous phase was extracted with ethyl acetate (3×), then the combined organic phases were washed with 5% NaHCO$_3$ and NaCl$_{sat}$, dried over MgSO$_4$ and concentrated. The crude product was purified by column chromatography (PE/EtOAc or CH$_2$Cl$_2$/MeOH) to obtain the desired product.

General Procedure 8:

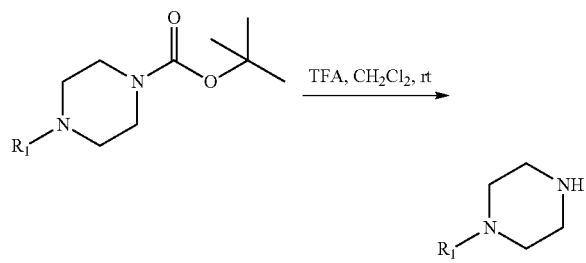

To a solution of Boc-piperazine derivative in CH$_2$Cl$_2$ TFA (0.6 mL) was added and the reaction mixture was stirred till completion, under N$_2$ at room temperature. Then, the obtained mixture was concentrated and the residue was dissolved in CH$_2$Cl$_2$ and NaHCO$_{3sat}$ was added. The aqueous phase was extracted with CH$_2$Cl$_2$. The combined organic phases were washed with water, dried over MgSO$_4$ and concentrated. The crude product was used directly in the further step or purified by column chromatography (CH$_2$Cl$_2$/MeOH) to give the desired product.

General Procedure 9:

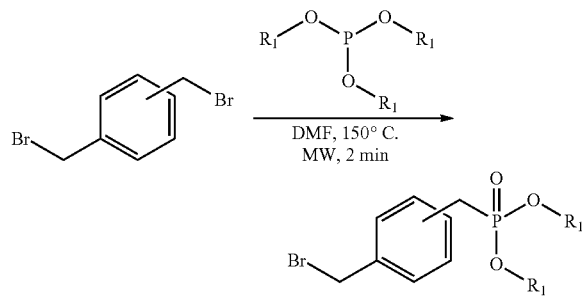

A microwave vial was charged with α,α-dibromo-m/p-xylene (0.40 g, 1.5 mmol, 2 equiv), phosphite derivative (0.75 mmol, 1 equiv) and DMF (0.8 mL). The reaction mixture was heated at 150° C. for 2 minutes through microwave activation. Then, the mixture was poured into water and the product was extracted with ethyl acetate. The combined organic phases were washed with water and brine, then dried over MgSO$_4$ and concentrated under vacuum. Purification by column chromatography on silica gel (PE/EtOAc or CH$_2$Cl$_2$/MeOH) gave the desired product.

General Procedure 10:

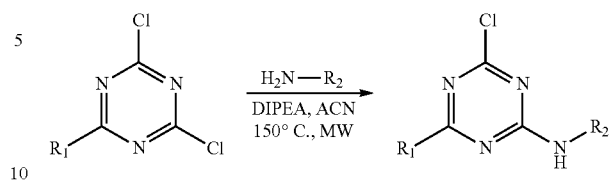

A microwave vial was charged with 2-substituted 4,6-dichloro-1,3,5-triazine (0.9 mmol, 1 equiv), amine derivative (0.9 mmol, 1 equiv), N,N-diisopropylethylamine (DIPEA) (0.17 mL, 0.99 mmol, 1.1 equiv) and acetonitrile (3 mL). The reaction mixture was heated at 150° C. under microwave irradiation, and then was concentrated. The resulted crude product was dissolved in CH$_2$Cl$_2$ or ethyl acetate and washed with 2M HCl and water. The collected organic phase was dried over MgSO$_4$ and concentrated to give the desired product.

General Procedure 11:

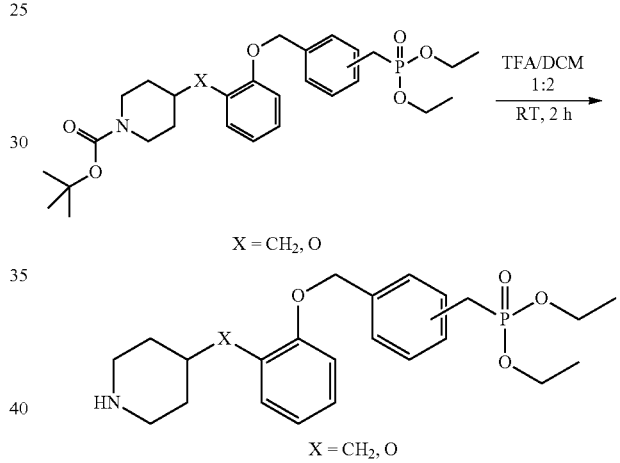

Trifluoroacetic acid (100 eq.) was added dropwise to a mixture of Boc-compound (1 eq.) in CH$_2$Cl$_2$ (2:1 CH$_2$Cl$_2$/trifluoroacetic acid v/v). The reaction was stirred at room temperature for 2 h and then volatiles were removed under reduced pressure. The crude product was extracted with ethyl acetate, washed with NaHCO$_3$ until pH 7, dried over MgSO$_4$, filtrated and concentrated under vacuum. Pure compounds were obtained after purification by flash column chromatography with dichloromethane/methanol (95:5) as eluent.

General Procedure 12:

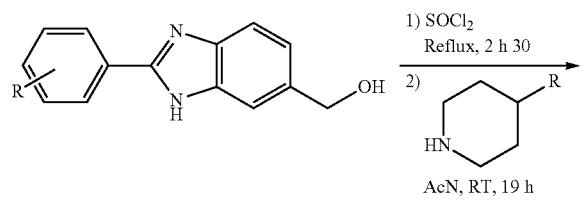

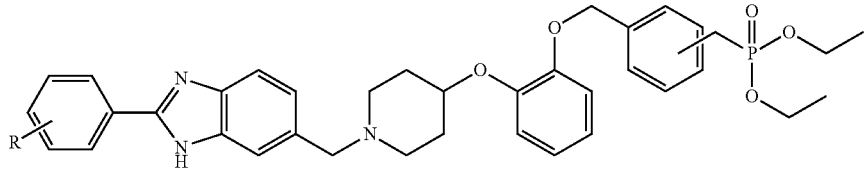

To a flask containing benzimidazole derivative (1 eq.), SOCl$_2$ (29 eq.) was added and the resulted mixture was stirred for 2 h30 at 80° C. After cooling to room temperature, SOCl$_2$ was evaporated and the obtained solid was diluted with acetonitrile (4 mL) and cooled to 0° C. Then, to the obtained solution, piperidine derivative (1 eq.) and diisopropylethylamine (5.3 eq.) were added. The ice bath was removed and the reaction mixture was allowed to stir for 16-19 h at room temperature. After concentration, the crude product was purified by column chromatography (CH$_2$Cl$_2$/MeOH) to give the desired product.

Example 1: Synthesis of N1-(benzyloxycarbonyl)-N4-[(2-phenyl-benzimidazol-5-yl)methyl]-piperazine (E1)

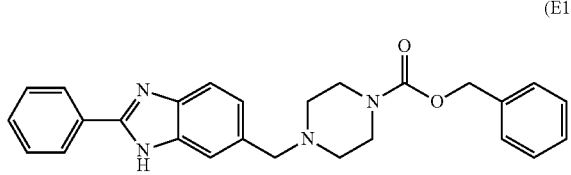

(E1)

Procedure:

1. Synthesis of Compound (1) N-(benzyloxycarbonyl)-piperazine

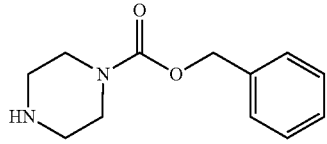

(1)

To a cooled solution of imidazole at 0° C. (1.00 g, 14.7 mmol, 2 equiv) in CH$_2$Cl$_2$ (18 mL), benzyl chloroformate (1.03 mL, 7.35 mmol, 1 equiv) was slowly added. After 1 h45 of stirring the white solid (imidazole hydrochloride) was filtered off. The obtained filtrate was concentrated, and then solubilised in ethanol (17.5 mL). In another flask the solution of piperazine dihydrochloride (1.75 g, 11.03 mmol, 1.5 equiv) in water (17.5 mL) was prepared, then added dropwisely to ethanolic solution of Cbz-imidazole. The resulted mixture was stirred for 4 h30 at room temperature and then concentrated to ¼$^{th}$ of its volume. Obtained aqueous phase was extracted with chloroform (4×) to remove the diacylated product, then NaOH$_{sat}$ was added to the previous aqueous phase (pH 9-10). The resulted aqueous phase was extracted again with chloroform (4×) to recover the monoacylated product. The organic phase with monoacylated product was washed with water (4×), dried over MgSO$_4$ and concentrated to give (1) (0.809 g, 50% in two steps) as a colorless oil.

2. Synthesis of Compound (2) 5-methyl carboxylate-2-phenyl-benzimidazole

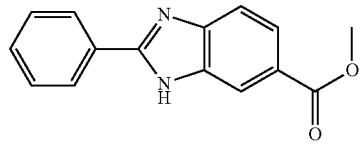

(2)

The title compound was prepared from benzaldehyde (0.4 mL, 3.94 mmol, 1 equiv) following the general procedure 4. Compound (2) (0.97 g, 97%) was obtained as a white solid.

3. Synthesis of Compound (3) 5-hydroxymethyl-2-phenyl-benzimidazole

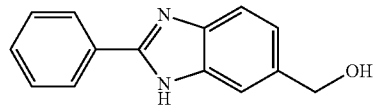

(3)

The title compound was prepared from (2) (0.10 g, 0.4 mmol, 1 equiv) following the general procedure 5. Compound (3) (0.09 g, quantitative) was obtained as a white solid.

4. Synthesis of Compound (E1)

The title compound was prepared from (3) (0.10 g, 0.4 mmol, 1 equiv) and (1) (0.09 g, 0.4 mmol, 1 equiv) following the general procedure 6. Compound (E1) (0.17 g, 87%) was obtained as a white solid.

Characterization:

$^1$H NMR: (400 MHz, CDCl$_3$) δ 11.08 (s, 1H, NH), 8.17-8.03 (m, 2H), 7.67-7.46 (m, 2H), 7.45-7.39 (m, 3H), 7.37-7.29 (m, 5H), 7.20 (dd, J=8.3, 1.3 Hz, 1H), 5.15 (s, 2H, CH$_2$), 3.60 (s, 2H, CH$_2$), 3.51 (bs, 4H, CH$_2$), 2.42 (bs, 4H, CH$_2$).

$^{13}$C NMR: (101 MHz, CDCl$_3$) δ 155.50, 152.36, 136.76, 130.23, 130.05, 129.14, 128.63, 128.17, 127.96, 126.81, 124.37, 67.34 (CH$_2$), 63.35 (CH$_2$), 52.76 (CH$_2$), 44.00 (CH$_2$).

HRMS (ESI): m/z [M+H]$^+$ calcd for C$_{26}$H$_{27}$N$_4$O$_2$ 427.2129 found 427.2129.

IR (cm$^{-1}$): 3064, 2929, 2809, 1699, 1431, 1362, 1286, 1237, 1122, 1078, 1001, 779, 762, 695.

Mp: 112° C.

R$_f$: 0.53 (CH$_2$Cl$_2$/MeOH 9:1)

Example 2: Synthesis of N1-[(2-benzhydryl-benzimidazol-5-yl)methyl]-N4-(benzyloxycarbonyl)-piperazine (E2)

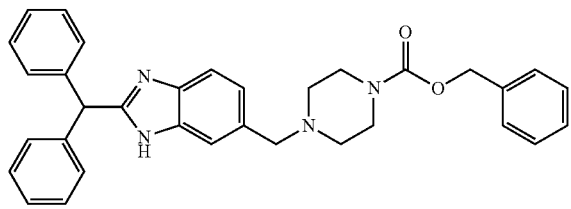

Procedure:

1. Synthesis of Compound (4) 2-benzhydryl-5-methyl carboxylate-benzimidazole

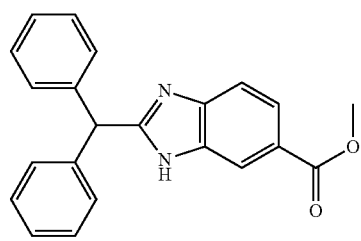

The title compound was prepared from diphenylacetaldehyde (0.16 mL, 0.9 mmol, 1 equiv) following the general procedure 4. Compound (4) (0.24 g, 79%) was obtained as an amorphous creamy solid.

2. Synthesis of Compound (5) 2-benzhydryl-5-hydroxymethyl-benzimidazole

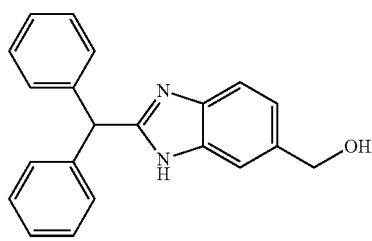

The title compound was prepared from (4) (0.21 g, 0.6 mmol, 1 equiv) following the general procedure 5. Compound (5) (0.19 g, quantitative) was obtained as an amorphous creamy solid.

3. Synthesis of Compound (E2)

The title compound was prepared from (5) (0.08 g, 0.25 mmol, 1 equiv) and (1) (0.055 g, 0.25 mmol, 1 equiv) following the general procedure 6. Compound (E2) (0.067 g, 51%) was obtained as an orange solid.

Characterization:

$^1$H NMR: (250 MHz, CDCl$_3$) δ 9.09 (s, 1H, NH), 7.86-7.30 (m, 13H), 7.27-7.15 (m, 5H), 5.84 (s, 1H, CH), 5.14 (s, 2H, CH$_2$), 3.62 (s, 2H, CH$_2$), 3.56-3.39 (m, 4H, CH$_2$), 2.45 (d, J=4.2 Hz, 4H, CH$_2$).

$^{13}$C NMR: (101 MHz, CDCl$_3$) δ 155.38, 140.66, 136.90, 129.03, 129.02, 128.61, 128.12, 127.98, 127.49, 67.20 (CH$_2$), 63.35 (CH$_2$), 52.78 (CH$_2$), 52.06 (CH), 43.99 (CH$_2$).

HRMS (ESI): m/z [M+H]$^+$ calcd for C$_{33}$H$_{33}$N$_4$O$_2$ 517.2598 found 517.2599.

IR (cm$^{-1}$): 3029, 2930, 0811, 1696, 1429, 1239, 1122, 731, 697.

Mp: 100° C.

R$_f$: 0.59 (CH$_2$Cl$_2$/MeOH 9:1)

Example 3: Synthesis of N1-(benzyloxycarbonyl)-N4-[[2-(3-pyridyl)-benzimidazol-5-yl]methyl]-piperazine (E3)

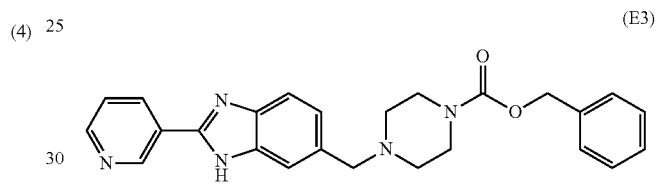

Procedure:

1. Synthesis of Compound (6) 5-methyl carboxylate-2-(3-pyridyl)-benzimidazole

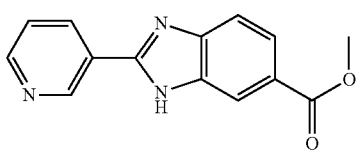

The title compound was prepared from 3-pyridine-carboxaldehyde (0.18 mL, 1.98 mmol, 1.1 equiv) following the general procedure 4. Compound (6) (0.38 g, 82%) was obtained as a yellow solid.

2. Synthesis of Compound (7) 5-hydroxymethyl-2-(3-pyridyl)-benzimidazole

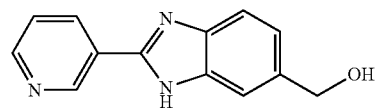

The title compound was prepared from (6) (0.12 g, 0.5 mmol, 1 equiv) following the general procedure 5. Compound (7) (0.11 g, quantitative) was obtained as a yellow solid.

3. Synthesis of Compound (E3)

The title compound was prepared from (7) (0.046 g, 0.22 mmol, 1 equiv) and (1) (0.048 g, 0.22 mmol, 1 equiv) following the general procedure 6. Compound (E3) (0.060 g, 69%) was obtained as a yellow solid.

Characterization:

$^1$H NMR: (400 MHz, CDCl$_3$) δ 12.68 (s, 1H, NH), 9.36 (s, 1H), 8.58 (d, J=3.8 Hz, 1H), 8.47 (d, J=8.0 Hz, 1H), 7.53 (s, 2H), 7.37-7.28 (m, 6H), 7.19 (d, J=8.2 Hz, 1H), 5.14 (s, 2H, CH$_2$), 3.61 (s, 2H, CH$_2$), 3.52 (s, 4H, CH$_2$), 2.44 (s, 4H, CH$_2$).

$^{13}$C NMR: (101 MHz, CDCl$_3$) δ 155.43, 150.27, 149.45, 147.37, 136.67, 134.69, 128.62, 128.18, 127.94, 126.83, 124.24, 67.37 (CH$_2$), 63.22 (CH$_2$), 52.75 (CH$_2$), 43.82 (CH$_2$).

HRMS (ESI): m/z [M+H]$^+$ calcd for C$_{25}$H$_{26}$N$_5$O$_2$ 428.2081 found 428.2079.

IR (cm$^{-1}$): 3035, 2928, 2810, 2164, 1696, 1429, 1121, 1001, 818, 733.

Mp: 90° C.

R$_f$: 0.49 (CH$_2$Cl$_2$/MeOH 9:1)

Example 4: Synthesis of N1-(benzyloxycarbonyl)-N4-[[2-(2-pyridyl)-benzimidazol-5-yl]methyl]-piperazine (E4)

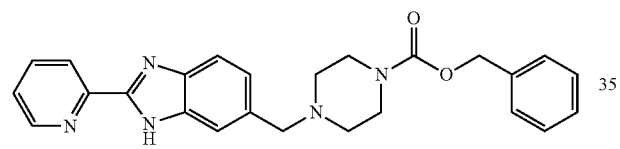

(E4)

Procedure:

1. Synthesis of Compound (8) 2-(2-pyridyl)-benzimidazole-5-carboxylic acid

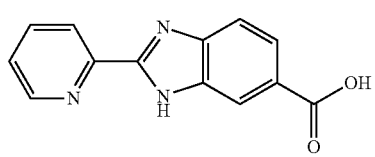

(8)

To a mixture of 3,4-diaminobenzoic acid (0.6 g, 3.94 mmol, 1 equiv) in EtOH (6 mL) and solution of cooper acetate monohydrate (0.86 g, 4.33 mmol, 1.1 equiv) in water (10 mL), 2-pyridine carboxaldehyde (0.42 mL, 4.33 mmol, 1.1 equiv) was added. The resulting mixture was stirred for 2 h at 100° C. Black precipitate was filtered off and dispersed in EtOH (4 mL). Then, Na$_2$S.xH$_2$O (1.7 g) was added and the mixture was stirred for 30 min at 100° C. The obtained solid was filtered off from hot solution and washed with hot water on the filter. The filtrate was acidified with HCl (pH~2) and then the resulted mixture was heating at 80° C. till the removing of H$_2$S. The cooled mixture was filtered off, concentrated and recrystallized from EtOH. The obtained dihydrochloride product was mixed with an equivalent quantity of KOH in ethanol. The solid was filtered off and the filtrate was concentrated to give (8) (0.447 g, 47%) as a brown solid.

2. Synthesis of Compound (9) 5-methyl carboxylate-2-(2-pyridyl)-benzimidazole

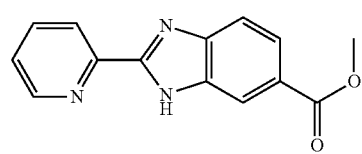

(9)

To the solution of (8) (0.15 g, 0.63 mmol, 1 equiv) in MeOH (1.1 mL), cooled at 0° C., SOCl$_2$ (0.07 mL, 0.98 mmol, 1.55 equiv) was slowly added. The reaction mixture was heated at 50° C. for 16 h. After cooling to room temperature the water was added and the mixture was concentrated to ¼$^{th}$ of its volume. The residue was adjusted to pH 6 with NaHCO$_{3sat}$, then extracted with EtOAc. The combined organic phases were dried over MgSO$_4$ and concentrated to give (9) (0.135 g, 85%) as a beige solid.

3. Synthesis of Compound (10) 5-hydroxymethyl-2-(2-pyridyl)-benzimidazole

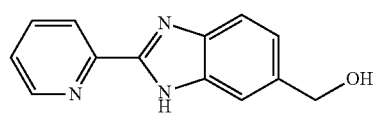

(10)

The title compound was prepared from (9) (0.08 g, 0.3 mmol, 1 equiv) following the general procedure 5. Compound (10) (0.07 g, quantitative) was obtained as a yellow solid.

4. Synthesis of Compound (E4)

The title compound was prepared from (10) (0.025 g, 0.11 mmol, 1 equiv) and (1) (0.024 g, 0.11 mmol, 1 equiv) following the general procedure 6. Compound (E4) (0.024 g, 51%) was obtained as a yellow solid.

Characterization:

$^1$H NMR: (400 MHz, CDCl$_3$) δ 10.87 (d, J=33.4 Hz, 1H, NH), 8.64 (d, J=4.7 Hz, 1H), 8.44 (d, J=7.9 Hz, 1H), 7.87 (td, J=7.8, 1.4 Hz, 1H), 7.78 (s, 1H), 7.58-7.29 (m, 7H), 7.27 (s, 1H), 5.14 (s, 2H, CH$_2$), 3.66 (s, 2H, CH$_2$), 3.58-3.43 (m, 4H, CH$_2$), 2.47 (s, 4H, CH$_2$).

$^{13}$C NMR: (101 MHz, CDCl$_3$) δ 155.39, 149.26, 148.44, 137.42, 136.91, 128.61, 128.11, 127.99, 124.69, 121.71, 67.21 (CH$_2$), 63.38 (CH$_2$), 52.86 (CH$_2$), 43.97 (CH$_2$).

HRMS (ESI): m/z [M+H]$^+$ calcd for C$_{25}$H$_{26}$N$_5$O$_2$ 428.2081 found 428.2082.

IR (cm$^{-1}$): 2930, 1693, 1596, 1445, 1285, 1236, 1121, 999, 965, 823, 795, 738, 696.

Mp: 94° C.

R$_f$: 0.53 (CH$_2$Cl$_2$/MeOH 9:1)

Example 5: Synthesis of N1-(benzyloxycarbonyl)-N4-[[2-[4-(trifluoromethyl)phenyl]-benzimidazol-5-yl]methyl]-piperazine (E5)

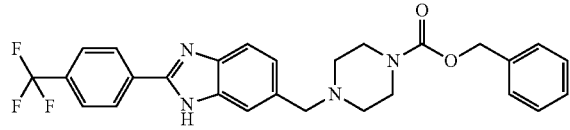

(E5)

Procedure:

1. Synthesis of Compound (11) 5-methyl carboxylate-2-[4-(trifluoromethyl)phenyl]-benzimidazole

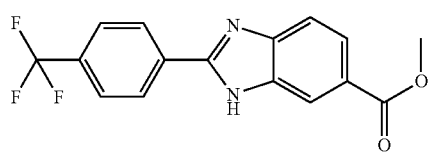

(11)

The title compound was prepared from 4-trifluoromethyl-benzaldehyde (0.41 mL, 3.00 mmol, 1 equiv) following the general procedure 4. Compound (11) (0.90 g, 93%) was obtained as a white solid.

2. Synthesis of Compound (12) 5-hydroxymethyl-2-[4-(trifluoromethyl)phenyl]-benzimidazole

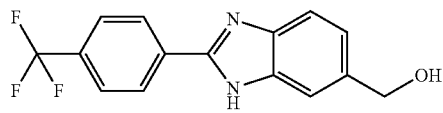

(12)

The title compound was prepared from (11) (0.40 g, 1.25 mmol, 1 equiv) following the general procedure 5. Compound (12) (0.35 g, 94%) was obtained as a white solid.

3. Synthesis of Compound (E5)

The title compound was prepared from (12) (0.20 g, 0.68 mmol, 1 equiv) and (1) (0.15 g, 0.68 mmol, 1 equiv) following the general procedure 6. Compound (E5) (0.29 g, 86%) was obtained as a white solid.

Characterization:

$^1$H NMR: (400 MHz, CDCl$_3$) δ 8.21 (d, J=8.1 Hz, 2H), 7.75 (s, 1H), 7.67 (d, J=8.3 Hz, 2H), 7.50-7.31 (m, 6H), 7.28-7.18 (m, 1H), 5.19 (s, 2H, CH$_2$), 3.63 (s, 2H, CH$_2$), 3.54 (s, 4H, CH$_2$), 2.45 (s, 4H, CH$_2$).

$^{13}$C NMR: (101 MHz, CDCl$_3$) δ 150.61, 133.42, 131.92, 128.67, 128.24, 127.89, 126.97, 126.13, 126.09, 125.29, 122.59, 67.52 (CH$_2$), 63.33 (CH$_2$), 52.74 (CH$_2$), 44.08 (CH$_2$).

$^{19}$F NMR: (376 MHz, CDCl$_3$) δ −62.83.

HRMS (ESI): m/z [M+H]$^+$ calcd for C$_{27}$H$_{26}$F$_3$N$_4$O$_2$ 495.2002 found 495.2001.

IR (cm$^{-1}$): 2938, 2810, 1674, 1620, 1434, 1322, 1238, 1166, 1117, 1065, 1016, 1001, 964, 850, 822, 787, 750, 695, 666.

Mp: 90° C.

R$_f$: 0.54 (CH$_2$Cl$_2$/MeOH 9:1)

Example 6: Synthesis of N1-(benzyloxycarbonyl)-N4-[[2-[3-(trifluoromethyl)phenyl]-benzimidazol-5-yl]methyl]-piperazine (E6)

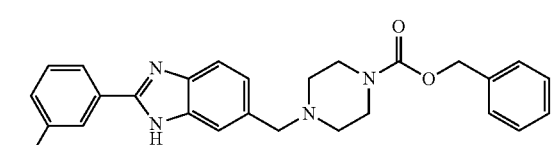

(E6)

Procedure:

1. Synthesis of Compound (13) 5-methyl carboxylate-2-[3-(trifluoromethyl)phenyl]-benzimidazole

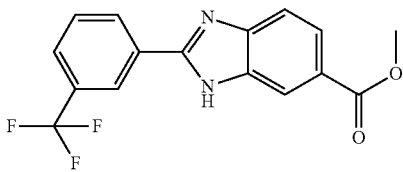

(13)

The title compound was prepared from 3-trifluoromethyl-benzaldehyde (0.24 mL, 1.8 mmol, 1 equiv) following the general procedure 4. Compound (13) (0.44 g, 76%) was obtained as a white solid.

2. Synthesis of Compound (14) 5-hydroxymethyl-2-[3-(trifluoromethyl)phenyl]-benzimidazole

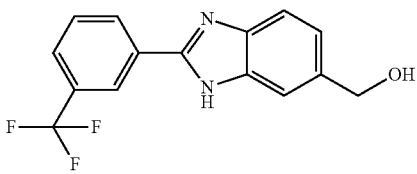

(14)

The title compound was prepared from (13) (0.31 g, 0.96 mmol, 1 equiv) following the general procedure 5. Compound (14) (0.27 g, 95%) was obtained as a white solid.

3. Synthesis of Compound (E6)

The title compound was prepared from (14) (0.20 g, 0.68 mmol, 1 equiv) and (1) (0.15 g, 0.68 mmol, 1 equiv) following the general procedure 6. Compound (E6) (0.32 g, 95%) was obtained as a white solid.

Characterization:

¹H NMR: (400 MHz, CDCl₃) δ 8.36 (s, 1H), 8.30 (d, J=7.8 Hz, 1H), 7.84-7.63 (m, 2H), 7.61-7.29 (m, 7H), 7.28-7.18 (m, 1H), 5.18 (s, 2H, CH₂), 3.65 (s, 2H, CH₂), 3.55 (s, 4H, CH₂), 2.46 (s, 4H, CH₂).

¹³C NMR: (101 MHz, CDCl₃) δ 150.65, 130.98, 129.87, 129.71, 128.65, 128.21, 127.93, 126.65, 125.25, 123.56, 67.44 (CH₂), 63.34 (CH₂), 52.79 (CH₂), 44.08 (CH₂).

¹⁹F NMR: (376 MHz, CDCl₃) δ −62.84.

HRMS (ESI): m/z [M+H]⁺ calcd for $C_{27}H_{26}F_3N_4O_2$ 495.2002 found 495.2002.

IR (cm⁻¹): 2902, 1698, 1670, 1434, 1417, 1327, 1280, 1237, 1168, 1120, 1072, 1001, 800, 764, 728, 695, 651.

Mp: 88° C.

R_f: 0.56 (CH₂Cl₂/MeOH 9:1)

Example 7: Synthesis of N1-(benzyloxycarbonyl)-N4-(2-phenyl-benzimidazole-5-carbonyl)-piperazine (E7)

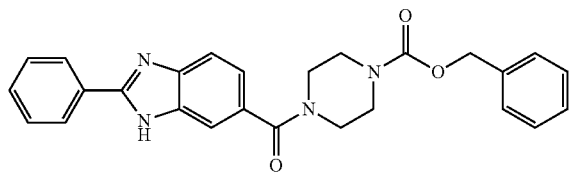

(E7)

Procedure:

1. Synthesis of Compound (15)
2-phenyl-benzimidazole-5-carboxylic acid

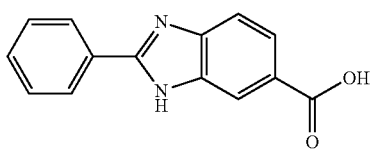

(15)

The title compound was prepared from benzaldehyde (0.2 mL, 1.97 mmol, 1 equiv) following the general procedure 3. Compound (15) (0.27 g, 62%) was obtained as a creamy solid.

2. Synthesis of Compound (E7)

The title compound was prepared from (15) (0.10 g, 0.4 mmol, 1 equiv) and (1) (0.10 g, 0.44 mmol, 1.1 equiv) following the general procedure 7. Compound (E7) (0.14 g, 90%) was obtained as a white solid.

Characterization:

¹H NMR: (250 MHz, DMSO) δ 13.13 (s, 1H, NH), 8.19 (dd, J=8.0, 1.6 Hz, 2H), 7.76-7.49 (m, 5H), 7.46-7.19 (m, 6H), 5.11 (s, 2H), 3.72-3.41 (m, 8H).

¹³C NMR: (101 MHz, DMSO) δ 129.01, 128.42, 127.87, 127.61, 126.59, 66.37 (O—CH₂), 43.79 (CH₂).

HRMS (ESI): m/z [M+H]⁺ calcd for $C_{26}H_{25}N_4O_3$: 441.1921, found 441.1917.

IR (cm⁻¹): 3065, 1687, 1611, 1427, 1228, 1011, 841, 695.

Mp: 146° C.

R_f: 0.5 (EtOAc)

Example 8: Synthesis of N1-(2-benzhydryl-benzimidazole-5-carbonyl)-N4-(benzyloxycarbonyl)-piperazine (E8)

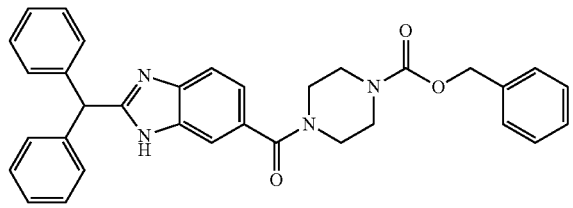

(E8)

Procedure:

1. Synthesis of Compound (16)
2-benzhydryl-benzimidazole-5-carboxylic acid

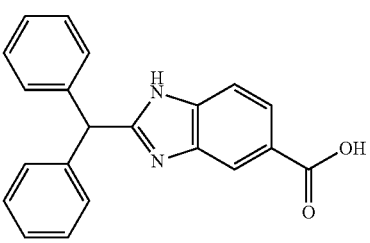

(16)

The title compound was prepared from diphenylacetaldehyde (0.18 mL, 1.00 mmol, 1 equiv) following the general procedure 3. Compound (16) (0.17 g, 52%) was obtained as a grey solid.

2. Synthesis of Compound (E8)

The title compound was prepared from (16) (0.06 g, 0.18 mmol, 1 equiv) and (1) (0.04 g, 0.20 mmol, 1.1 equiv) following the general procedure 7. Compound (E8) (0.072 g, 75%) was obtained as an amorphous creamy solid.

Characterization:

¹H NMR: (400 MHz, CDCl₃) δ 10.54 (s, 1H, NH), 7.52 (bs, 1H), 7.44-7.32 (m, 5H), 7.29-7.21 (m, 7H), 7.19-7.08 (m, 5H), 5.73 (s, 1H, CH), 5.15 (s, 2H, O—CH₂), 3.50 (bs, 8H, CH₂).

¹³C NMR: (101 MHz, CDCl₃) δ 171.59, 155.32, 140.46, 136.48, 129.05, 128.97, 128.76, 128.42, 128.20, 127.48, 67.70 (CH₂), 52.01 (CH), 44.07 (CH₂).

HRMS (ESI): m/z [M+H]⁺ calcd for $C_{33}H_{31}N_4O_3$ 531.2391 found 531.2399.

IR (cm⁻¹): 3029, 1698, 1611, 1494, 1448, 1359, 1286, 1227, 1108, 1007, 744, 697.

R_f: 0.65 (CH₂Cl₂/MeOH 9:1)

Example 9: Synthesis of N1-(benzyloxycarbonyl)-N4-[2-(3-pyridyl)-benzimidazole-5-carbonyl]-piperazine (E9)

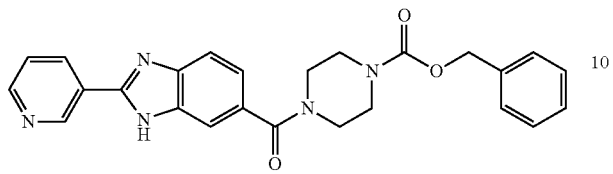
(E9)

Procedure:

1. Synthesis of Compound (17)
2-(3-pyridyl)-benzimidazole-5-carboxylic acid

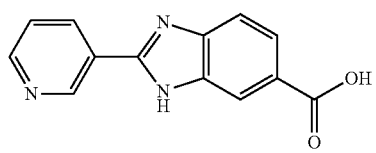
(17)

The title compound was prepared from 3-pyridine-carboxaldehyde (0.19 mL, 2.00 mmol, 1 equiv) following the general procedure 3. Compound (17) (0.46 g, 97%) was obtained as a beige solid.

2. Synthesis of Compound (E9)

The title compound was prepared from (17) (0.10 g, 0.42 mmol, 1 equiv) and (1) (0.10 g, 0.46 mmol, 1.1 equiv) following the general procedure 7. Compound (E9) (0.18 g, 96%) was obtained as a yellow solid.

Characterization:

$^1$H NMR: (400 MHz, DMSO) δ 13.32 (s, 1H, NH), 9.35 (d, J=1.9 Hz, 1H), 8.70 (dd, J=4.8, 1.5 Hz, 1H), 8.50 (dt, J=8.0, 1.8 Hz, 1H), 7.75 (s, 1H), 7.60 (dd, J=8.0, 4.8 Hz, 2H), 7.44-7.34 (m, 4H), 7.34-7.27 (m, 2H), 5.10 (s, 2H, O—CH$_2$), 3.78-3.39 (m, 8H, CH$_2$).

$^{13}$C NMR: (101 MHz, DMSO) δ 154.45, 150.83, 147.63, 136.76, 133.94, 128.43, 127.89, 127.60, 125.83, 124.08, 66.38 (CH$_2$), 44.63 (CH$_2$).

HRMS (ESI): m/z [M+H]$^+$ calcd for C$_{25}$H$_{24}$N$_5$O$_3$ 442.1874 found 442.1875.

IR (cm$^{-1}$): 1686, 1614, 1429, 1362, 1287, 1235, 1116, 1013, 961, 838, 741, 699.

Mp: 130° C.

R$_f$: 0.46 (CH$_2$Cl$_2$/MeOH 9:1)

Example 10: Synthesis of N1-(benzyloxycarbonyl)-N4-[2-(2-pyridyl)-benzimidazole-5-carbonyl]piperazine (E10)

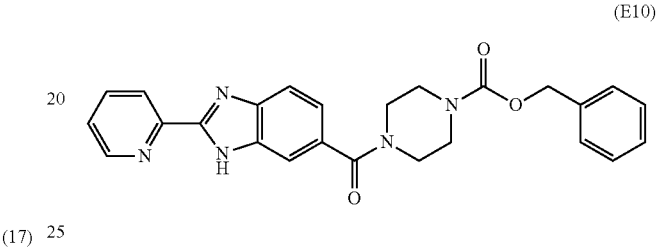
(E10)

Procedure:

The title compound was prepared from (8) (0.15 g, 0.63 mmol, 1 equiv) and (1) (0.15 g, 0.69 mmol, 1.1 equiv) following the general procedure 7. Compound (E10) (0.22 g, 78%) was obtained as a yellow solid.

Characterization:

$^1$H NMR: (400 MHz, CDCl$_3$) δ 12.12-11.82 (m, 1H, NH), 8.59 (d, J=4.5 Hz, 1H), 8.46 (dd, J=7.6, 4.2 Hz, 1H), 7.92-7.81 (m, 2H), 7.57-7.30 (m, 8H), 5.16 (s, 2H, O—CH$_2$), 3.99-3.22 (m, 8H, CH$_2$).

$^{13}$C NMR: (101 MHz, CDCl$_3$) δ 171.27, 171.10, 155.21, 152.69, 152.42, 149.13, 148.11, 145.58, 143.84, 137.55, 136.39, 135.43, 134.19, 130.59, 129.55, 128.59, 128.23, 128.02, 125.02, 123.51, 122.19, 122.10, 121.68, 119.98, 119.13, 111.92, 111.37, 67.52 (CH$_2$), 43.96 (CH$_2$).

HRMS (ESI): m/z [M+H]$^+$ calcd for C$_{25}$H$_{24}$N$_5$O$_3$ 442.1874 found 442.1873.

IR (cm$^{-1}$): 3062, 2321, 1697, 1615, 1421, 1226, 1106, 1010, 798, 743, 696.

Mp: 165° C.

R$_f$: 0.61 (CH$_2$Cl$_2$/MeOH 9:1)

Example 11: Synthesis of N1-[[2-[(4-methoxycarbonylphenyl)methoxy]phenyl]methyl]-N4-[(2-phenyl-benzimidazol-5-yl)methyl]-piperazine (E11)

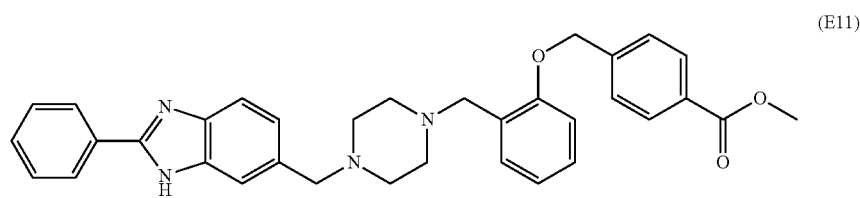 [SMILES: COC(=O)c1ccc(COc2ccccc2CN2CCN(Cc3ccc4nc(-c5ccccc5)[nH]c4c3)CC2)cc1]
(E11)

Procedure:

1. Synthesis of Compound (18) methyl 4-[(2-formylphenoxy)methyl]benzoate

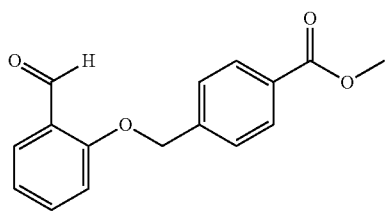
(18)

The title compound was prepared from methyl 4-(bromomethyl) benzoate (0.25 g, 1.09 mmol, 1 equiv) and salicylaldehyde (0.13 mL, 1.20 mmol, 1.1 equiv) following the general procedure 1. Compound (18) (0.30 g, quantitative) was obtained as a white solid.

2. Synthesis of Compound (E11)

The title compound was prepared from (E1) (0.07 g, 0.16 mmol, 1 equiv) and (18) (0.043 g, 0.16 mmol, 1 equiv) following the general procedure 2. Compound (E11) (0.071 g, 79%) was obtained as an amorphous creamy solid.

Characterization:

$^1$H NMR: (400 MHz, CDCl$_3$) δ 11.33 (s, 1H, NH), 8.15-8.06 (m, 2H), 8.03 (d, J=8.2 Hz, 2H), 7.66-7.32 (m, 8H), 7.21 (t, J=7.1 Hz, 1H), 7.15 (d, J=8.1 Hz, 1H), 6.94 (t, J=7.3 Hz, 1H), 6.86 (d, J=8.2 Hz, 1H), 5.08 (s, 2H, CH$_2$), 3.93 (s, 3H, CH$_3$), 3.71-3.53 (m, 4H, CH$_2$), 2.80-2.33 (m, 8H, CH$_2$).

$^{13}$C NMR: (101 MHz, CDCl$_3$) δ 167.23, 156.97, 152.38, 142.65, 131.57, 130.23, 130.15, 130.02, 129.69, 129.11, 128.68, 127.09, 126.92, 124.55, 121.13, 112.15, 70.69 (CH$_2$), 69.65 (CH$_2$), 63.25 (CH$_2$), 56.42 (CH$_2$), 52.91 (CH$_2$), 52.79 (CH$_2$), 52.41 (CH$_3$).

HRMS (ESI): m/z [M+H]$^+$ calcd for C$_{34}$H$_{35}$N$_4$O$_3$ 547.2704 found 547.2700.

IR (cm$^{-1}$): 3061, 2927, 2811, 1719, 1453, 1435, 1278, 1107, 756, 697.

R$_f$: 0.4 (CH$_2$Cl$_2$/MeOH 9:1)

Example 12: Synthesis of N1-[(2-benzhydryl-benzimidazol-5-yl)methyl]-N4-[[2-[(4-methoxycarbonylphenyl)methoxy]phenyl]methyl]-piperazine (E12)

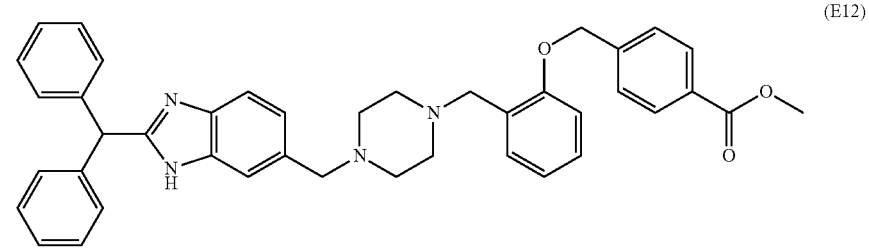 [SMILES: COC(=O)c1ccc(COc2ccccc2CN2CCN(Cc3ccc4nc(C(c5ccccc5)c5ccccc5)[nH]c4c3)CC2)cc1]
(E12)

Procedure:

The title compound was prepared from (E2) (0.018 g, 0.03 mmol, 1 equiv) and (18) (0.008 g, 0.03 mmol, 1 equiv) following the general procedure 2. Compound (E12) (0.013 g, 60%) was obtained as an amorphous creamy solid.

Characterization:

$^1$H NMR: (250 MHz, CDCl$_3$) δ 9.10 (d, J=20.7 Hz, 1H, NH), 8.07 (d, J=8.3 Hz, 2H), 7.66 (s, 1H), 7.54 (d, J=8.2 Hz, 2H), 7.45-7.13 (m, 14H), 7.03-6.83 (m, 2H), 5.83 (s, 1H, CH), 5.15 (s, 2H, CH$_2$), 3.94 (s, 3H, CH$_3$), 3.67 (s, 4H, CH$_2$), 2.56 (s, 8H, CH$_2$).

$^{13}$C NMR: (101 MHz, CDCl$_3$) δ 140.72, 129.96, 129.67, 129.02, 127.46, 127.02, 121.06, 112.10, 69.63 (CH$_2$), 63.35 (CH$_2$), 56.43 (CH$_2$), 53.11 (CH$_2$), 52.30 (CH$_3$), 52.07 (CH).

HRMS (ESI): m/z [M+H]$^+$ calcd for C$_{41}$H$_{41}$N$_4$O$_3$ 637.3173 found 637.3167.

IR (cm$^{-1}$): 3027, 2930, 2810, 1719, 1666, 1492, 1452, 1416, 1279, 1238, 1107, 1009, 753, 730, 698.

R$_f$: 0.26 (CH$_2$Cl$_2$/MeOH 9:1)

Example 13: Synthesis of N1-[[2-[(4-methoxycarbonylphenyl)methoxy]phenyl]methyl]-N4-[[2-(3-pyridyl)-benzimidazol-5-yl]methyl]-piperazine (E13)

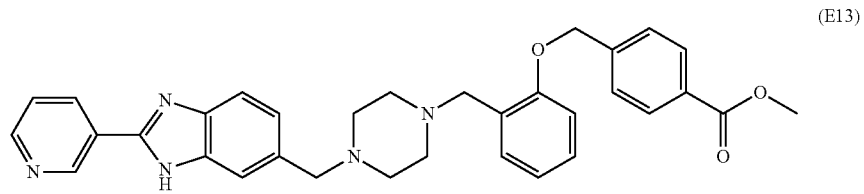 [SMILES: COC(=O)c1ccc(COc2ccccc2CN2CCN(Cc3ccc4nc(-c5cccnc5)[nH]c4c3)CC2)cc1]

Procedure:

The title compound was prepared from (E3) (0.059 g, 0.14 mmol, 1 equiv) and (18) (0.038 g, 0.14 mmol, 1 equiv) following the general procedure 2. Compound (E13) (0.029 g, 38%) was obtained as an amorphous creamy solid.

Characterization:

$^1$H NMR: (400 MHz, CDCl$_3$) δ 10.18 (s, 1H), 9.42 (s, 1H), 8.63 (s, 1H), 8.54 (d, J=7.5 Hz, 1H), 8.03 (dd, J=8.0, 1.9 Hz, 2H), 7.65-7.53 (m, 2H), 7.45 (dd, J=7.2, 0.8 Hz, 2H), 7.40 (s, 1H), 7.34 (d, J=7.2 Hz, 1H), 7.23 (t, J=7.7 Hz, 1H), 7.17 (d, J=8.1 Hz, 1H), 6.94 (t, J=7.3 Hz, 1H), 6.87 (d, J=8.2 Hz, 1H), 5.09 (s, 2H, O—CH$_2$), 3.92 (s, 3H, CH$_3$), 3.83-3.67 (m, 4H, CH$_2$), 2.75 (bs, 8H, CH$_2$).

$^{13}$C NMR: (101 MHz, CDCl$_3$) δ 167.06, 157.01, 142.24, 134.93 (CH), 131.97, 130.04, 129.84 (CH), 129.44 (CH), 127.09 (CH), 124.96 (CH), 121.29 (CH), 112.15 (CH), 69.69 (CH$_2$), 62.31 (CH$_2$), 55.40 (CH$_2$), 52.38 (CH$_3$), 51.61 (CH$_2$), 51.29 (CH$_2$).

HRMS (ESI): m/z [M+H]$^+$ calcd for C$_{33}$H$_{34}$N$_5$O$_3$ 548.2656 found 548.2653.

IR (cm$^{-1}$): 2922, 2850, 1718, 1451, 1280, 1107, 1020, 757, 709, 656.

R$_f$: 0.34 (CH$_2$Cl$_2$/MeOH 9:1)

Example 14: Synthesis of N1-[[2-[(4-methoxycarbonylphenyl)methoxy]phenyl]methyl]-N4-[[2-(2-pyridyl)-benzimidazol-5-yl]methyl]-piperazine (E14)

Procedure

The title compound was prepared from (E4) (0.03 g, 0.07 mmol, 1 equiv) and (18) (0.02 g, 0.07 mmol, 1 equiv) following the general procedure 2. Compound (E14) (0.030 g, 79%) was obtained as a creamy solid.

Characterization:

$^1$H NMR: (250 MHz, DMSO) δ 8.62 (d, J=4.5 Hz, 1H), 8.46 (d, J=7.9 Hz, 1H), 8.07 (d, J=8.2 Hz, 2H), 7.87 (t, J=7.7 Hz, 1H), 7.74-7.44 (m, 4H), 7.41-7.30 (m, 2H), 7.22 (d, J=8.2 Hz, 2H), 7.02-6.84 (m, 2H), 5.13 (s, 2H, CH$_2$), 3.94 (s, 3H, CH$_3$), 3.78 (s, 2H, CH$_2$), 3.72 (s, 2H, CH$_2$), 2.68 (s, 8H, CH$_2$).

$^{13}$C NMR: (101 MHz, CDCl$_3$) δ 166.97, 156.94, 151.12, 149.14, 148.41, 142.47, 137.46, 131.64, 129.99, 129.74, 128.78, 126.91, 124.66, 121.83, 121.13, 112.11, 69.63 (CH$_2$), 63.00 (CH$_2$), 55.87 (CH$_2$), 52.41 (CH$_2$), 52.27 (CH$_3$).

HRMS (ESI): m/z [M+H]$^+$ calcd for C$_{33}$H$_{34}$N$_5$O$_3$ 548.2656 found 548.2653.

IR (cm$^{-1}$): 2942, 2808, 1718, 1595, 1447, 1278, 1241, 1107, 1009, 795, 755, 697.

R$_f$: 0.24 (CH$_2$Cl$_2$/MeOH 9:1)

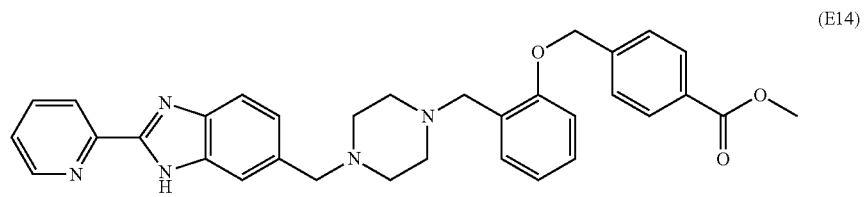 [SMILES: COC(=O)c1ccc(COc2ccccc2CN2CCN(Cc3ccc4nc(-c5ccccn5)[nH]c4c3)CC2)cc1]

Example 15: Synthesis of N1-[[2-[4-(trifluoromethyl)phenyl]-benzimidazol-5-yl]methyl]-N4-[[2-[(4-methoxycarbonylphenyl)methoxy]phenyl]methyl]-piperazine

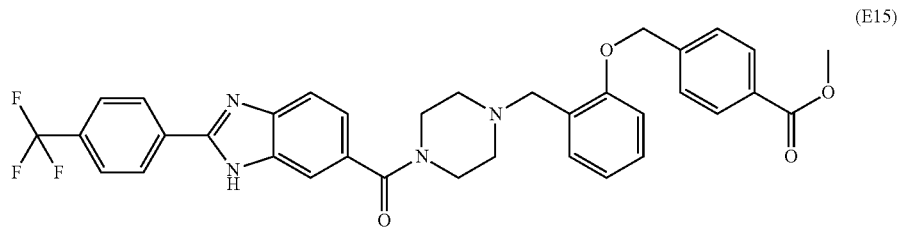 [SMILES: COC(=O)c1ccc(COc2ccccc2CN2CCN(C(=O)c3ccc4nc(-c5ccc(C(F)(F)F)cc5)[nH]c4c3)CC2)cc1]

(E15)

Procedure:

The title compound was prepared from (E5) (0.10 g, 0.2 mmol, 1 equiv) and (18) (0.054 g, 0.2 mmol, 1 equiv) following the general procedure 2. Compound (E15) (0.05 g, 40%) was obtained as a creamy solid.

Characterization:

$^1$H NMR: (400 MHz, CDCl$_3$) δ 8.16 (d, J=8.1 Hz, 2H), 8.02 (d, J=8.3 Hz, 2H), 7.89-7.31 (m, 7H), 7.25-7.13 (m, 2H), 6.96 (t, J=7.2 Hz, 1H), 6.87 (d, J=8.1 Hz, 1H), 5.06 (s, 2H, CH$_2$), 3.95 (s, 3H, CH$_3$), 3.65 (s, CH$_2$), 3.58 (s, 2H, CH$_2$), 2.67-2.36 (m, 8H, CH$_2$).

$^{13}$C NMR: (101 MHz, CDCl$_3$) δ 167.14, 156.83, 150.35, 142.45, 133.38, 131.64, 131.32, 129.79, 129.46, 128.52, 126.99, 126.86, 125.87, 125.83, 125.17, 122.47, 120.93, 111.95, 69.47 (CH$_2$), 63.04 (CH$_2$), 56.54 (CH$_2$), 53.07 (CH$_2$), 52.67 (CH$_2$), 52.24 (CH$_3$).

$^{19}$F NMR: (376 MHz, CDCl$_3$) δ −62.80.

HRMS (ESI): m/z [M+H]$^+$ calcd for C$_{35}$H$_{34}$F$_3$N$_4$O$_3$ 615.2578 found 615.2581.

IR (cm$^{-1}$): 2939, 2811, 1720, 1619, 1602, 1492, 1453, 1436, 1323, 1279, 1240, 1165, 1108, 1065, 1016, 965, 849, 754, 695.

R$_f$: 0.62 (CH$_2$Cl$_2$/MeOH 9:1)

Example 16: Synthesis of N1-[[2-[3-(trifluoromethyl)phenyl]-benzimidazol-5-yl]methyl]-N4-[[2-[(4-methoxycarbonylphenyl)methoxy]phenyl]methyl]-piperazine (E16)

Procedure:

The title compound was prepared from (E6) (0.060 g, 0.12 mmol, 1 equiv) and (18) (0.032 g, 0.12 mmol, 1 equiv) following the general procedure 2. Compound (E16) (0.023 g, 31%) was obtained as a white solid.

Characterization:

$^1$H NMR: (400 MHz, CDCl$_3$) δ 8.38 (s, 1H), 8.30 (d, J=7.7 Hz, 1H), 8.05 (d, J=8.3 Hz, 2H), 7.78-7.39 (m, 6H), 7.36 (d, J=7.4 Hz, 1H), 7.26-7.15 (m, 2H), 6.96 (t, J=7.4 Hz, 1H), 6.88 (d, J=8.1 Hz, 1H), 5.08 (s, 2H, CH$_2$), 3.96 (s, 3H, CH$_3$), 3.68 (s, 2H, CH$_2$), 3.62 (s, 2H, CH$_2$), 2.79-2.37 (m, 8H, CH$_2$).

$^{13}$C NMR: (101 MHz, CDCl$_3$) δ 156.99, 150.64, 142.55, 131.71, 131.38, 131.11, 129.96, 129.64, 129.61, 128.76, 127.25, 126.53, 123.58, 121.13, 112.07, 77.36, 69.66 (CH$_2$), 63.11 (CH$_2$), 56.39 (CH$_2$), 52.91 (CH$_2$), 52.69 (CH$_2$), 52.41 (CH$_3$).

$^{19}$F NMR: (376 MHz, CDCl$_3$) δ −62.75.

HRMS (ESI): m/z [M+H]$^+$ calcd for C$_{35}$H$_{34}$F$_3$N$_4$O$_3$ 615.2578 found 615.2575.

IR (cm$^{-1}$): 2938, 2809, 2360, 2343, 2324, 1718, 1457, 1327, 1279, 1241, 1167, 1120, 1108, 1072, 806, 756, 697.

Mp: 102° C.

R$_f$: 0.47 (CH$_2$Cl$_2$/MeOH 9:1)

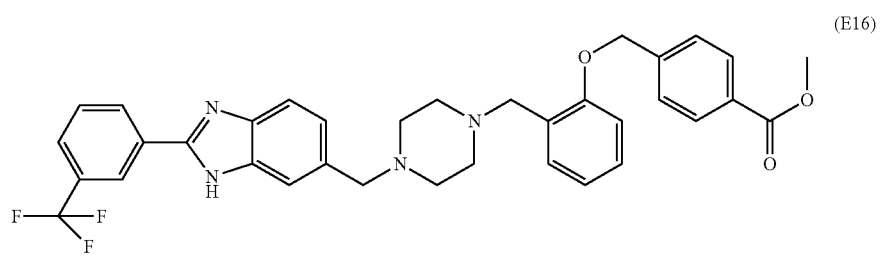 [SMILES: COC(=O)c1ccc(COc2ccccc2CN2CCN(Cc3ccc4nc(-c5cccc(C(F)(F)F)c5)[nH]c4c3)CC2)cc1]

(E16)

Example 17: Synthesis of N1-[[2-[(4-methoxycarbonylphenyl)methoxy]phenyl]methyl]-N4-(2-phenyl-benzimidazole-5-carbonyl)-piperazine (E17)

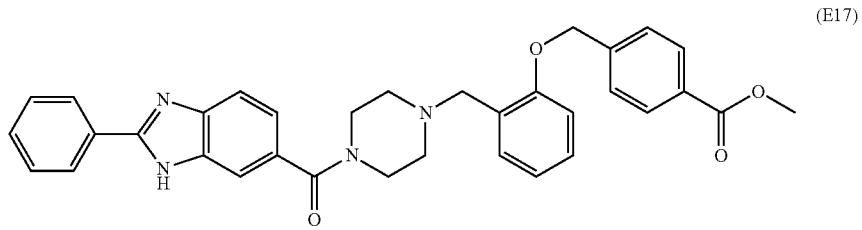 [SMILES: COC(=O)c1ccc(COc2ccccc2CN2CCN(C(=O)c3ccc4nc(-c5ccccc5)[nH]c4c3)CC2)cc1]
(E17)

Procedure:

The title compound was prepared from (E7) (0.046 g, 0.1 mmol, 1 equiv) and (18) (0.043 g, 0.1 mmol, 1 equiv) following the general procedure 2. Compound (E17) (0.034 g, 59%) was obtained as a white solid.

Characterization:

$^1$H NMR: (400 MHz, MeOD) δ 8.15-8.05 (m, 2H), 8.03 (d, J=8.4 Hz, 2H), 7.67 (s, 2H), 7.61-7.52 (m, 5H), 7.38-7.27 (m, 2H), 7.27-7.18 (m, 1H), 7.02 (d, J=7.8 Hz, 1H), 6.95 (dd, J=8.3, 7.4 Hz, 1H), 5.18 (s, 2H, —OCH$_2$), 3.89 (s, 3H CH$_3$), 3.74-3.51 (m, 6H, CH$_2$), 2.54 (bs, 4H, CH$_2$).

$^{13}$C NMR: (101 MHz, MeOD) δ 158.36, 144.40, 132.49, 131.83, 130.76, 130.72, 130.58, 130.25, 129.94, 128.28, 127.98, 126.65, 121.90, 113.38, 70.48 (CH$_2$), 57.26 (CH$_2$), 52.63 (CH$_3$).

HRMS (ESI): m/z [M+H]$^+$ calcd for C$_{34}$H$_{33}$N$_4$O$_4$ 561.2496 found 561.2496.

IR (cm$^{-1}$): 3224, 2926, 2796, 1720, 1618, 1442, 1233, 1104, 1018, 752, 695.

Mp: 255° C.

R$_f$: 0.5 (CH$_2$Cl$_2$/MeOH 9:1)

Example 18: Synthesis of N1-(2-benzhydryl-benzimidazole-5-carbonyl)-N4-[[2-[(4-methoxycarbonylphenyl)methoxy]phenyl]methyl]-piperazine (E18)

Procedure:

The title compound was prepared from (E8) (0.029 g, 0.05 mmol, 1 equiv) and (18) (0.014 g, 0.05 mmol, 1 equiv) following the general procedure 2. Compound (E18) (0.022 g, 63%) was obtained as a white solid.

Characterization:

$^1$H NMR: (250 MHz, CDCl$_3$) δ 9.98 (d, J=96.5 Hz, 1H, NH), 8.04 (d, J=8.0 Hz, 2H), 7.76-7.57 (m, 1H), 7.51 (d, J=8.1 Hz, 2H), 7.43 (bs, 1H), 7.34 (d, J=6.2 Hz, 2H), 7.28-7.10 (m, 11H), 7.05-6.83 (m, 2H), 5.77 (s, 1H, CH), 5.13 (s, 2H, O—CH$_2$), 3.90 (s, 3H, CH$_3$), 3.79-3.33 (m, 6H, CH$_2$), 2.50 (bs, 4H, CH$_2$).

$^{13}$C NMR: (101 MHz, CDCl$_3$) δ 171.14, 156.95, 140.53, 130.05, 129.83, 129.08, 127.53, 121.19, 112.22, 69.70 (CH$_2$), 56.54 (CH$_2$), 52.40 (CH$_3$), 52.09 (CH).

HRMS (ESI): m/z [M+H]$^+$ calcd for C$_{41}$H$_{39}$N$_4$O$_4$ 651.2966 found 651.2961.

IR (cm$^{-1}$): 2922, 1719, 1603, 1433, 1279, 1235, 1106, 1016, 1001, 818, 753, 698.

Mp: 196° C.

R$_f$: 0.77 (CH$_2$Cl$_2$/MeOH 9:1)

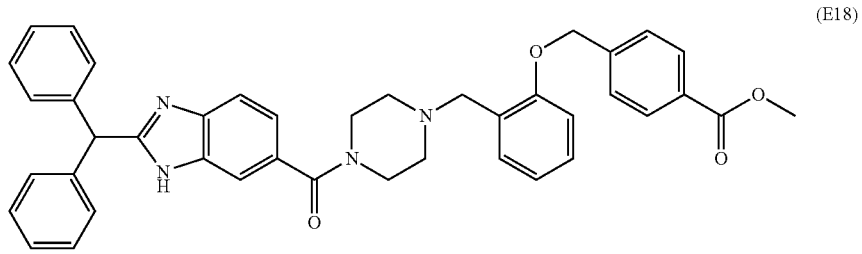 [SMILES: COC(=O)c1ccc(COc2ccccc2CN2CCN(C(=O)c3ccc4nc(C(c5ccccc5)c5ccccc5)[nH]c4c3)CC2)cc1]
(E18)

Example 19: Synthesis of N1-[[2-[(4-methoxycarbonylphenyl)methoxy]phenyl]methyl]-N4-[2-(3-pyridyl)-benzimidazole-5-carbonyl]-piperazine (E19)

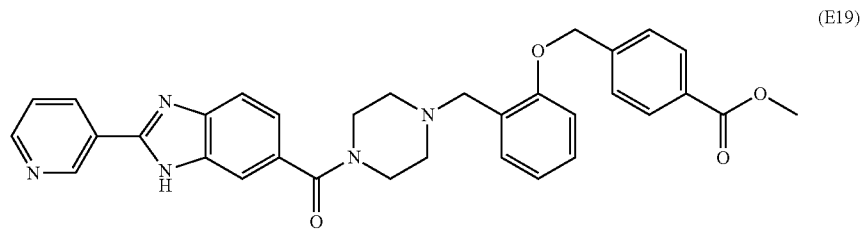 [SMILES: COC(=O)c1ccc(COc2ccccc2CN2CCN(C(=O)c3ccc4nc(-c5cccnc5)[nH]c4c3)CC2)cc1]

Procedure:
The title compound was prepared from (E9) (0.07 g, 0.16 mmol, 1 equiv) and (18) (0.043 g, 0.16 mmol, 1 equiv) following the general procedure 2. Compound (E19) (0.05 g, 55%) was obtained as a creamy solid.

Characterization:
$^1$H NMR: (400 MHz, CDCl$_3$) δ 9.35 (s, 1H), 8.61 (d, J=4.6 Hz, 1H), 8.42 (d, J=7.8 Hz, 1H), 8.06 (d, J=7.0 Hz, 2H), 7.50 (t, J=12.8 Hz, 4H), 7.34 (t, J=6.6 Hz, 2H), 7.27-7.21 (m, 1H), 7.19 (d, J=8.2 Hz, 1H), 6.98 (t, J=7.2 Hz, 1H), 6.91 (d, J=8.1 Hz, 1H), 5.15 (s, 2H, —OCH$_2$), 3.92 (s, 3H, CH$_3$), 3.86-3.38 (m, 6H, CH$_2$), 2.78-2.37 (m, 4H, CH$_2$).
$^{13}$C NMR: (101 MHz, CDCl$_3$) δ 171.55, 167.13, 156.95, 150.72, 148.00, 142.58, 134.81, 131.32, 130.07, 129.84, 128.90, 127.07, 126.38, 124.02, 121.23, 112.23, 69.69 (CH$_2$), 56.40 (CH$_2$), 53.63 (CH$_2$), 52.43 (CH$_3$).
HRMS (ESI): m/z [M+H]$^+$ calcd for C$_{33}$H$_{32}$N$_5$O$_4$ 562.2449 found 562.2445.
IR (cm$^{-1}$): 2949, 2321, 1981, 1717, 1602, 1435, 1281, 1237, 1108, 1020, 840, 755, 704.
R$_f$: 0.37 (CH$_2$Cl$_2$/MeOH 9:1)

Example 20: Synthesis of N1-[[2-[(4-methoxycarbonylphenyl)methoxy]phenyl]methyl]-N4-[2-(2-pyridyl)-benzimidazole-5-carbonyl]-piperazine (E20)

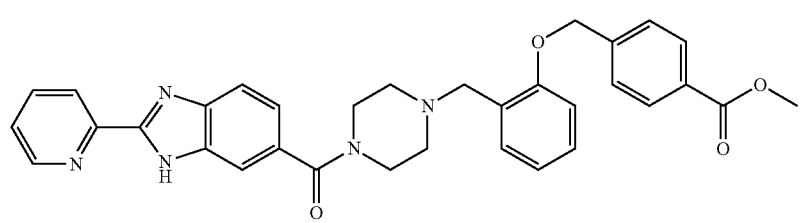

Procedure:
The title compound was prepared from (E10) (0.08 g, 0.18 mmol, 1 equiv) and (18) (0.049 g, 0.18 mmol, 1 equiv) following the general procedure 2. Compound (E20) (0.05 g, 50%) was obtained as a white solid.

Characterization:
$^1$H NMR: (400 MHz, CDCl$_3$) δ 11.27 (d, J=18.2 Hz, 1H, NH), 8.63 (d, J=4.5 Hz, 1H), 8.45 (d, J=7.9 Hz, 1H), 8.07 (d, J=8.3 Hz, 2H), 7.95-7.77 (m, 2H), 7.64-7.47 (m, 3H), 7.45-7.31 (m, 3H), 7.23 (dt, J=8.1, 1.7 Hz, 1H), 6.97 (t, J=7.4 Hz, 1H), 6.90 (d, J=8.0 Hz, 1H), 5.14 (s, 2H, CH$_2$), 3.93 (s, 3H, CH$_3$), 3.84-3.22 (m, 6H, CH$_2$), 2.56 (s, 4H, CH$_2$).
$^{13}$C NMR: (101 MHz, CDCl$_3$) δ 167.04, 156.93, 149.35, 148.15, 142.63, 137.62, 131.17, 130.05, 129.84, 128.65, 126.97, 126.28, 125.09, 122.08, 121.15, 112.21, 69.66 (CH$_2$), 56.56 (CH$_2$), 53.24 (CH$_2$), 52.36 (CH$_3$).
HRMS (ESI): m/z [M+H]$^+$ calcd for C$_{33}$H$_{32}$N$_5$O$_4$ 562.2449 found 562.2451.
IR (cm$^{-1}$): 2946, 1718, 1613, 1492, 1434, 1278, 1234, 1106, 1019, 997, 798, 753, 696.
Mp: 96° C.
R$_f$: 0.47 (CH$_2$Cl$_2$/MeOH 9:1)

Example 21: Synthesis of N1-[4-(trifluoromethyl)benzyl]-N4-[(2-phenyl-benzimidazol-5-yl)methyl]-piperazine (E21)

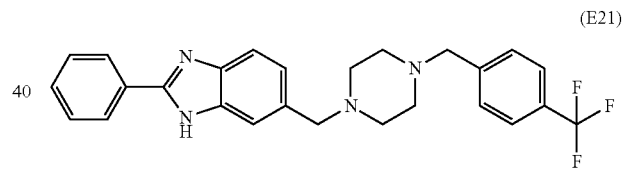

Procedure:
The title compound was prepared from (3) (0.02 g, 0.09 mmol, 1 equiv) and 1-[4-(trifluoromethyl)-benzyl]piperazine (0.02 mL, 0.09 mmol, 1 equiv) following the general procedure 6. Compound (E21) (0.04 g, quantitative) was obtained as a white solid.

Characterization:
$^1$H NMR: (400 MHz, CDCl$_3$) δ 11.75 (s, 1H, NH), 8.17-7.97 (m, 2H), 7.62-7.45 (m, 4H), 7.42 (d, J=8.0 Hz, 2H), 7.39-7.33 (m, 3H), 7.20 (dd, J=8.3, 1.3 Hz, 1H), 3.59 (s, 2H), 3.51 (s, 2H), 2.69-2.22 (m, 8H).

$^{13}$C NMR: (101 MHz, CDCl$_3$) δ 152.57, 142.70, 130.26 (CH), 130.14, 129.62, 129.39 (CH), 129.30, 129.20 (CH), 126.96 (CH), 125.79, 125.32 (CH), 125.29 (CH), 124.69 (CH), 123.09, 63.43 (CH$_2$), 62.57 (CH$_2$), 53.21 (CH$_2$), 53.12 (CH$_2$).

HRMS (ESI): m/z [M+H]$^+$ calcd for C$_{26}$H$_{26}$F$_3$N$_4$ 451.2104 found 451.2107.

IR (cm$^{-1}$): 2935, 2810, 1457, 1324, 1290, 1160, 1121, 1065, 1009, 808, 701.

Mp: 178° C.

R$_f$: 0.47 (CH$_2$Cl$_2$/MeOH 9:1)

Example 22: Synthesis of N1-[(2-benzhydryl-benzimidazol-5-yl)methyl]-N4-[4-(trifluoromethyl)benzyl]-piperazine (E22)

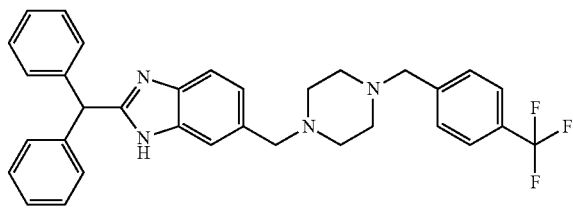

(E22)

Procedure:

The title compound was prepared from (5) (0.05 g, 0.16 mmol, 1 equiv) and 1-[4-(trifluoromethyl)-benzyl]piperazine (0.03 mL, 0.16 mmol, 1 equiv) following the general procedure 6. Compound (E22) (0.06 g, 71%) was obtained as a white solid.

Characterization:

$^1$H NMR: (400 MHz, CDCl$_3$) δ 9.13 (d, J=31.8 Hz, 1H, NH), 7.71-7.61 (m, 1H), 7.56 (d, J=8.2 Hz, 2H), 7.44 (d, J=8.0 Hz, 2H), 7.37-7.30 (m, 4H), 7.27-7.16 (m, 8H), 5.79 (s, 1H, CH), 3.61 (d, J=8.0 Hz, 2H, CH$_2$), 3.55 (s, 2H, CH$_2$), 2.48 (s, 8H, CH$_2$).

$^{13}$C NMR: (101 MHz, CDCl$_3$) δ 140.68, 129.33, 129.02, 129.01, 127.48, 125.27, 125.23, 119.27, 63.35 (CH$_2$), 62.56 (CH$_2$), 53.25 (CH$_2$), 53.13 (CH$_2$), 52.04 (CH).

HRMS (ESI): m/z [M+H]$^+$ calcd for C$_{33}$H$_{32}$F$_3$N$_4$ 541.2574 found 541.2575.

IR (cm$^{-1}$): 2945, 2817, 1065, 1120, 1161, 1289, 1161, 1120, 1065, 1016, 730, 711, 700.

Mp: 236° C.

R$_f$: 0.62 (CH$_2$Cl$_2$/MeOH 9:1)

Example 23: Synthesis of N1-[4-(trifluoromethyl)benzyl]-N4-[[2-(3-pyridyl)-benzimidazol-5-yl]methyl]-piperazine (E23)

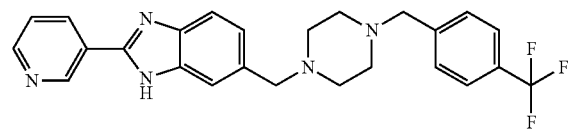

(E23)

Procedure:

The title compound was prepared from (7) (0.035 g, 0.16 mmol, 1 equiv) and 1-[4-(trifluoromethyl)-benzyl]piperazine (0.03 mL, 0.16 mmol, 1 equiv) following the general procedure 6. Compound (E23) (0.05 g, 70%) was obtained as a yellow solid.

Characterization:

$^1$H NMR: (400 MHz, CDCl$_3$) δ 12.47 (s, 1H, NH), 9.31 (s, 1H), 8.59 (d, J=3.6 Hz, 1H), 8.45 (d, J=8.0 Hz, 1H), 7.68-7.38 (m, 6H), 7.35 (dd, J=7.9, 4.8 Hz, 1H), 7.20 (d, J=8.2 Hz, 1H), 3.60 (s, 2H, CH$_2$), 3.52 (s, 2H, CH$_2$), 2.62-2.26 (m, 8H, CH$_2$).

$^{13}$C NMR: (101 MHz, CDCl$_3$) δ 150.29, 149.27, 147.21, 142.64, 134.88, 129.39, 127.00, 125.36, 125.32, 124.41, 63.37 (CH$_2$), 62.56 (CH$_2$), 53.17 (CH$_2$).

HRMS (ESI): m/z [M+H]$^+$ calcd for C$_{25}$H$_{25}$F$_3$N$_5$ 425.2056 found 425.2052.

IR (cm$^{-1}$): 2932, 2811, 1417, 1322, 1160, 1118, 1065, 811, 706.

Mp: 138° C.

R$_f$: 0.48 (CH$_2$Cl$_2$/MeOH 9:1)

Example 24: Synthesis of N1-[4-(trifluoromethyl)benzyl]-N4-[[2-(2-pyridyl)-benzimidazol-5-yl]methyl]-piperazine (E24)

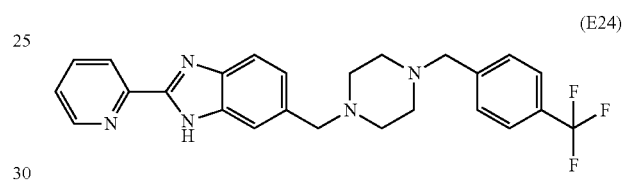

(E24)

Procedure:

The title compound was prepared from (10) (0.02 g, 0.09 mmol, 1 equiv) and 1-[4-(trifluoromethyl)-benzyl]piperazine (0.02 mL, 0.09 mmol, 1 equiv) following the general procedure 6. Compound (E24) (0.03 g, 80%) was obtained as an amorphous creamy solid.

Characterization:

$^1$H NMR: (400 MHz, CDCl$_3$) δ 10.80 (d, J=40.6 Hz, 1H, NH), 8.64 (d, J=3.9 Hz, 1H), 8.44 (d, J=6.8 Hz, 1H), 7.87 (t, J=7.7 Hz, 1H), 7.81-7.70 (m, 1H), 7.67-7.42 (m, 5H), 7.39-7.35 (m, 1H), 7.31-7.21 (m, 1H), 3.66 (d, J=9.6 Hz, 2H, CH$_2$), 3.56 (s, 2H, CH$_2$), 2.50 (s, 8H, CH$_2$).

$^{13}$C NMR: (101 MHz, CDCl$_3$) δ 149.26, 149.26, 148.47, 143.92, 142.70, 137.42, 134.06, 129.35, 125.67, 125.28, 124.64, 124.48, 121.67, 120.71, 119.77, 111.69, 110.98, 63.40 (CH$_2$), 62.58 (CH$_2$), 53.32 (CH$_2$), 53.28 (CH$_2$), 53.22 (CH$_2$), 53.07 (CH$_2$).

HRMS (ESI): m/z [M+H]$^+$ calcd for C$_{25}$H$_{25}$F$_3$N$_5$ 452.2057 found 452.2058.

IR (cm$^{-1}$): 2935, 2811, 1447, 1324, 1160, 1119, 1065, 1009, 795.

R$_f$: 0.54 (CH$_2$Cl$_2$/MeOH 9:1)

Example 25: Synthesis of N1-[4-(trifluoromethyl)benzyl]-N4-(2-phenyl-benzimidazole-5-carbonyl)-piperazine (E25)

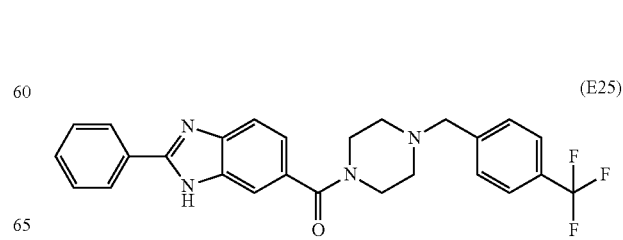

(E25)

Procedure:

The title compound was prepared from (15) (0.05 g, 0.21 mmol, 1 equiv) and 1-[4-(trifluoromethyl)-benzyl]piperazine (0.05 mL, 0.23 mmol, 1.1 equiv) following the general procedure 7. Compound (E25) (0.08 g, 86%) was obtained as a white solid.

Characterization:

$^1$H NMR: (250 MHz, CDCl$_3$) δ 12.82-12.11 (m, 1H, NH), 8.12 (dd, J=6.5, 3.0 Hz, 2H), 7.77-7.43 (m, 5H), 7.41-7.26 (m, 4H), 7.20 (d, J=8.0 Hz, 1H), 4.01-3.31 (m, 6H, CH$_2$), 2.45 (s, 4H, CH$_2$).

$^{13}$C NMR: (101 MHz, CDCl$_3$) δ 171.65, 142.01, 130.39, 129.90, 129.74, 129.57, 129.29, 128.97, 127.07, 125.46, 125.42, 122.96, 62.32 (CH$_2$), 53.39 (CH$_2$), 52.75 (CH$_2$), 48.42 (CH$_2$), 42.84 (CH$_2$).

HRMS (ESI): m/z [M+H]$^+$ calcd for C$_{26}$H$_{24}$F$_3$N$_4$O 465.1897 found 465.1895.

IR (cm$^{-1}$): 1616, 1576, 1443, 1420, 1321, 1313, 1224, 1164, 1155, 1103, 1064, 1017, 1001, 824, 780, 774, 694, 640.

Mp: 220° C.

R$_f$: 0.65 (CH$_2$Cl$_2$/MeOH 9:1)

Example 26: Synthesis of N1-(2-benzhydryl-benzimidazole-5-carbonyl)-N4-[4-(trifluoromethyl)benzyl]-piperazine (E26)

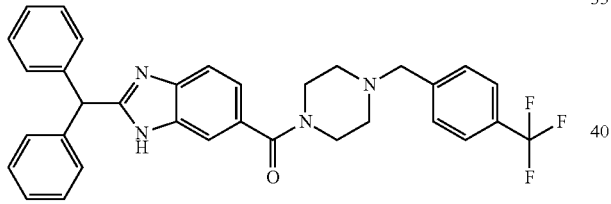

(E26)

Procedure:

The title compound was prepared from (16) (0.05 g, 0.15 mmol, 1 equiv) and 1-[4-(trifluoromethyl)-benzyl]piperazine (0.03 mL, 0.17 mmol, 1.1 equiv) following the general procedure 7. Compound (E26) (0.07 g, 79%) was obtained as a yellow solid.

Characterization:

$^1$H NMR: (400 MHz, CDCl$_3$) δ 10.86 (s, 1H, NH), 7.50 (dd, J=55.5, 7.2 Hz, 6H), 7.33-6.72 (m, 11H), 5.67 (s, 1H, CH), 4.01-3.14 (m, 6H, CH$_2$), 2.41 (s, 4H, CH$_2$).

$^{13}$C NMR: (101 MHz, CDCl$_3$) δ 171.35, 157.54, 142.11, 140.55, 129.92, 129.59, 129.36 (CH), 129.06 (CH), 128.91 (CH), 127.38 (CH), 125.72, 125.50 (CH), 125.46 (CH), 123.01, 62.43 (CH$_2$), 53.03 (CH$_2$), 51.96 (CH).

HRMS (ESI): m/z [M+H]$^+$ calcd for C$_{33}$H$_{30}$N$_4$O 555.2366 found 555.2366.

IR (cm$^{-1}$): 2934, 2815, 1607, 1419, 1323, 1161, 1119, 1065, 1018, 1001, 841, 824, 743, 699, 641.

Mp: 148° C.

R$_f$: 0.45 (CH$_2$Cl$_2$/MeOH 9:1)

Example 27: Synthesis of N1-[4-(trifluoromethyl)benzyl]-N4-[2-(3-pyridyl)-benzimidazole-5-carbonyl]-piperazine (E27)

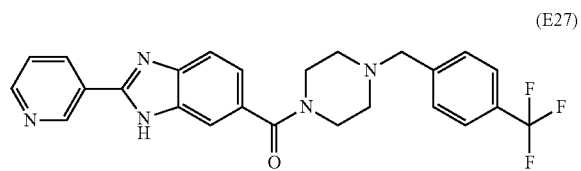 [SMILES: O=C(c1ccc2nc(-c3cccnc3)[nH]c2c1)N1CCN(Cc2ccc(C(F)(F)F)cc2)CC1]

(E27)

Procedure:

The title compound was prepared from (17) (0.05 g, 0.21 mmol, 1 equiv) and 1-[4-(trifluoromethyl)-benzyl]piperazine (0.05 mL, 0.23 mmol, 1.1 equiv) following the general procedure 7. Compound (E27) (0.096 g, 99%) was obtained as an amorphous creamy solid.

Characterization:

$^1$H NMR: (400 MHz, CDCl$_3$) δ 13.06 (s, 1H, NH), 9.33 (bs, 1H), 8.60 (d, J=4.7 Hz, 1H), 8.41 (d, J=8.0 Hz, 1H), 7.65-7.40 (m, 5H), 7.35-7.25 (m, 2H), 7.18 (d, J=8.0 Hz, 1H), 3.82 (bs, 2H, CH$_2$), 3.62-3.42 (m, 4H, CH$_2$), 2.59-2.28 (m, 4H, CH$_2$).

$^{13}$C NMR: (101 MHz, CDCl$_3$) δ 171.57, 151.27, 150.64, 147.90, 141.93, 141.13, 134.67, 130.20, 129.88, 129.56, 129.27, 129.16, 126.33, 125.62, 125.44, 125.40, 123.95, 122.92, 62.25 (CH$_2$), 53.34 (CH$_2$), 52.68 (CH$_2$), 50.57 (CH$_2$), 44.41 (CH$_2$).

HRMS (ESI): m/z [M+H]$^+$ calcd for C$_{25}$H$_{23}$F$_3$N$_5$O 466.1849 found 466.1849.

IR (cm$^{-1}$): 3659, 2971, 2284, 2165, 2050, 1981, 1605, 1495, 1439, 1324, 1118, 1065, 843, 707.

R$_f$: 0.39 (CH$_2$Cl$_2$/MeOH 9:1)

Example 28: Synthesis of N1-[4-(trifluoromethyl)benzyl]-N4-[2-(2-pyridyl)-benzimidazole-5-carbonyl]-piperazine (E28)

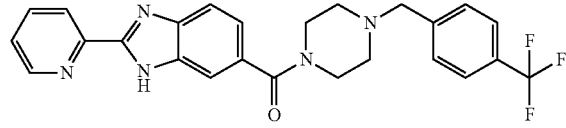

(E28)

Procedure:

The title compound was prepared from (8) (0.05 g, 0.21 mmol, 1 equiv) and 1-[4-(trifluoromethyl)-benzyl]piperazine (0.05 mL, 0.23 mmol, 1.1 equiv) following the general procedure 7. Compound (E28) (0.07 g, 76%) was obtained as a creamy solid.

Characterization:

$^1$H NMR: (250 MHz, CDCl$_3$) δ 11.75-11.15 (m, 1H, NH), 8.65 (d, J=4.8 Hz, 1H), 8.47 (d, J=7.9 Hz, 1H), 8.05-7.73 (m, 2H), 7.62-7.47 (m, 5H), 7.44-7.34 (m, 2H), 3.94-3.40 (m, 6H, CH$_2$), 2.49 (bs, 4H, CH$_2$).

$^{13}$C NMR: (101 MHz, CDCl$_3$) δ 170.93, 149.28, 148.08, 142.06, 137.60, 129.84, 129.52, 129.30, 125.65, 125.43, 125.39, 125.08, 123.74, 122.94, 122.05, 119.98, 119.18, 111.76, 111.18, 62.42 (CH$_2$), 53.55 (CH$_2$).

HRMS (ESI): m/z [M+H]+ calcd for $C_{25}H_{23}F_3N_5O$ 466.1849 found 466.1847.
IR (cm$^{-1}$): 1614, 1437, 1323, 1161, 1118, 1106, 1065, 1019, 997, 822, 796, 727, 698, 642, 621.
$R_f$: 0.27 (CH$_2$Cl$_2$/MeOH 9:1)

Example 29: Synthesis of N1-[3-(trifluoromethoxy)benzyl]-N4-[(2-phenyl-benzimidazol-5-yl)methyl]-piperazine (E29)

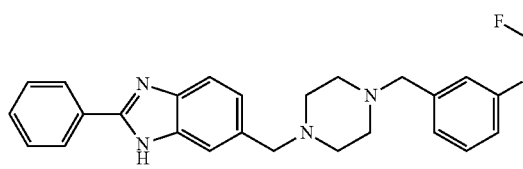
(E29)

Procedure:
The title compound was prepared from (3) (0.05 g, 0.22 mmol, 1 equiv) and 1-[3-(trifluoromethoxy)-benzyl]piperazine (0.05 mL, 0.22 mmol, 1 equiv) following the general procedure 6. Compound (E29) (0.09 g, 88%) was obtained as a yellow solid.
Characterization:
$^1$H NMR: (400 MHz, CDCl$_3$) δ 8.24-8.06 (m, 2H), 7.59 (bs, 2H), 7.52-7.38 (m, 3H), 7.31 (t, J=7.8 Hz, 1H), 7.21 (dd, J=12.9, 5.5 Hz, 3H), 7.10 (d, J=7.8 Hz, 1H), 3.69 (s, 2H, CH$_2$), 3.49 (s, 2H, CH$_2$), 2.79-2.26 (m, 8H, CH$_2$).
$^{13}$C NMR: (101 MHz, CDCl$_3$) δ 152.44, 149.49, 140.73, 130.24, 130.03, 129.64, 129.14, 127.38, 126.88, 124.72, 121.45, 119.62, 63.17 (CH$_2$), 62.20 (CH$_2$), 52.91 (CH$_2$), 52.56 (CH$_2$).
HRMS (ESI): m/z [M+H]+ calcd for $C_{26}H_{26}F_3N_4O$ 467.2053 found 467.2049.
IR (cm$^{-1}$): 2811, 1456, 1254, 1213, 1154, 1010, 778, 700, 633.
Mp: 80° C.
$R_f$: 0.36 (CH$_2$Cl$_2$/MeOH 9:1)

Example 30: Synthesis of N1-[(2-benzhydryl-benzimidazol-5-yl)methyl]-N4-[3-(trifluoromethoxy)benzyl]-piperazine (E30)

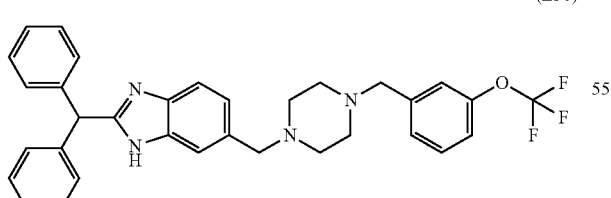
(E30)

Procedure:
The title compound was prepared from (5) (0.05 g, 0.16 mmol, 1 equiv) and 1-[3-(trifluoromethoxy)-benzyl]piperazine (0.035 mL, 0.16 mmol, 1 equiv) following the general procedure 6. Compound (E30) (0.06 g, 65%) was obtained as a white solid.

Characterization:
$^1$H NMR: (400 MHz, CDCl$_3$) δ 9.63-9.26 (m, 1H, NH), 7.66-7.57 (m, 1H), 7.43-7.16 (m, 15H), 7.10 (d, J=8.0 Hz, 1H), 5.77 (s, 1H, CH), 3.61 (s, 2H, CH$_2$), 3.51 (s, 2H, CH$_2$), 2.48 (s, 8H, CH$_2$).
$^{13}$C NMR: (101 MHz, CDCl$_3$) δ 155.44, 149.45, 141.00, 140.69, 129.56, 129.01, 128.97, 127.97, 127.43, 127.38, 127.31, 121.88, 121.48, 119.48, 119.33, 63.33 (CH$_2$), 62.38 (CH$_2$), 53.10 (CH$_2$), 51.98 (CH$_2$).
HRMS (ESI): m/z [M+H]+ calcd for $C_{33}H_{32}F_3N_4O$ 557.2523 found 557.2516.
IR (cm$^{-1}$): 2810, 1450, 1256, 1214, 1155, 1010, 868, 795, 699, 634.
Mp: 86° C.
$R_f$: 0.49 (CH$_2$Cl$_2$/MeOH 9:1)

Example 31: Synthesis of N1-[3-(trifluoromethoxy)benzyl]-N4-[[2-(3-pyridyl)-benzimidazol-5-yl]methyl]-piperazine (E31)

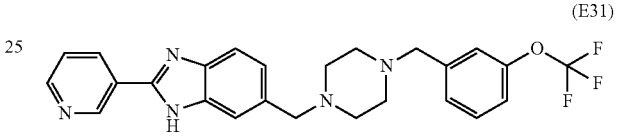
(E31)

Procedure:
The title compound was prepared from (7) (0.04 g, 0.18 mmol, 1 equiv) and 1-[3-(trifluoromethoxy)-benzyl]piperazine (0.04 mL, 0.18 mmol, 1 equiv) following the general procedure 6. Compound (E31) (0.055 g, 66%) was obtained as a yellow solid.
Characterization:
$^1$H NMR: (400 MHz, CDCl$_3$) δ 12.95 (s, 1H, NH), 9.33 (d, J=1.6 Hz, 1H), 8.57 (dd, J=4.8, 1.4 Hz, 1H), 8.46 (d, J=8.0 Hz, 1H), 7.67-7.28 (m, 4H), 7.26-7.15 (m, 3H), 7.09 (d, J=8.1 Hz, 1H), 3.59 (s, 2H, CH$_2$), 3.48 (s, 2H, CH$_2$), 2.74-2.18 (m, 8H, CH$_2$).
$^{13}$C NMR: (101 MHz, CDCl$_3$) δ 150.10, 149.46, 149.25, 147.15, 140.93, 134.82, 129.58, 127.34, 126.99, 124.33, 121.87, 121.43, 119.52, 119.32, 63.29 (CH$_2$), 62.32 (CH$_2$), 53.11 (CH$_2$), 53.00 (CH$_2$).
HRMS (ESI): m/z [M+H]+ calcd for $C_{25}H_{25}F_3N_5O$ 468.2006 found 468.2001.
IR (cm$^{-1}$): 2810, 1445, 1255, 1213, 1155, 1010, 814, 795, 703, 632.
Mp; 110° C.
$R_f$: 0.4 (CH$_2$Cl$_2$/MeOH 9:1)

Example 32: Synthesis of N1-[3-(trifluoromethoxy)benzyl]-N4-[[2-(2-pyridyl)-benzimidazol-5-yl]methyl]-piperazine (E32)

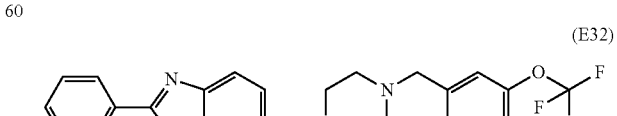
(E32)

Procedure:

The title compound was prepared from (10) (0.05 g, 0.22 mmol, 1 equiv) and 1-[3-(trifluoromethoxy)-benzyl]piperazine (0.05 mL, 0.22 mmol, 1 equiv) following the general procedure 6. Compound (E32) (0.07 g, 68%) was obtained as a yellow solid.

Characterization:

$^1$H NMR: (250 MHz, CDCl$_3$) δ 10.75 (d, J=22.6 Hz, 1H, NH), 8.65 (d, J=4.6 Hz, 1H), 8.45 (d, J=7.9 Hz, 1H), 7.88 (td, J=7.8, 1.5 Hz, 1H), 7.79 (s, 1H), 7.53-7.40 (m, 1H), 7.38 (dd, J=5.3, 1.9 Hz, 1H), 7.32 (d, J=7.8 Hz, 1H), 7.29-7.17 (m, 3H), 7.11 (d, J=7.8 Hz, 1H), 3.68 (s, 2H, CH$_2$), 3.55 (s, 2H, CH$_2$), 2.53 (s, 8H, CH$_2$).

$^{13}$C NMR: (101 MHz, CDCl$_3$) δ 149.48, 149.28, 148.46, 141.04, 137.39, 129.57, 127.40, 124.65, 121.66, 121.50, 119.50, 63.42 (CH$_2$), 62.42 (CH$_2$), 53.17 (CH$_2$).

HRMS (ESI): m/z [M+H]$^+$ calcd for C$_{25}$H$_{25}$F$_3$N$_5$O 468.2006 found 468.2001.

IR (cm$^{-1}$): 1593, 1446, 1255, 1213, 1154, 1009, 794, 743, 700, 633, 621.

Mp: 65° C.

R$_f$: 0.26 (CH$_2$Cl$_2$/MeOH 9:1)

Example 33: Synthesis of N1-[3-(trifluoromethoxy) benzyl]-N4-(2-phenyl-benzimidazole-5-carbonyl)-piperazine (E33)

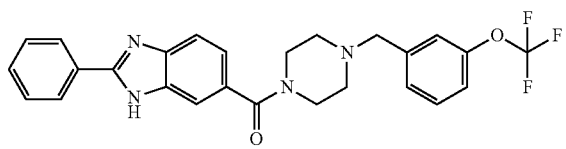

(E33)

Procedure:

The title compound was prepared from (15) (0.05 g, 0.21 mmol, 1 equiv) and 1-[3-(trifluoromethoxy)-benzyl]piperazine (0.05 mL, 0.23 mmol, 1.1 equiv) following the general procedure 7. Compound (E33) (0.054 g, 53%) was obtained as an amorphous creamy solid.

Characterization:

$^1$H NMR: (400 MHz, CDCl$_3$) δ 12.08 (s, 1H, NH), 8.10 (dd, J=6.6, 2.9 Hz, 2H), 7.53 (bs, 2H), 7.43-7.37 (m, 3H), 7.34 (d, J=7.9 Hz, 1H), 7.27-7.17 (m, 3H), 7.13 (d, J=7.4 Hz, 1H), 4.10-3.33 (m, 6H, CH$_2$), 2.66-2.22 (m, 4H, CH$_2$).

$^{13}$C NMR: (101 MHz, CDCl$_3$) δ 171.59, 153.96, 149.58, 140.42, 130.44, 129.80, 129.71, 129.40, 129.01, 127.32, 127.04, 121.38, 119.84, 62.21 (CH$_2$).

HRMS (ESI): m/z [M+H]$^+$ calcd for C$_{26}$H$_{24}$F$_3$N$_4$O$_2$ 481.1846 found 481.1840.

IR (cm$^{-1}$): 1617, 1488, 1443, 1313, 1258, 1212, 1158, 1016, 1002, 956, 895, 844, 780, 752, 693, 633.

R$_f$: 0.44 (CH$_2$Cl$_2$/MeOH 9:1)

Example 34: Synthesis of N1-(2-benzhydryl-benzimidazole-5-carbonyl)-N4-[3-(trifluoromethoxy) benzyl]-piperazine (E34)

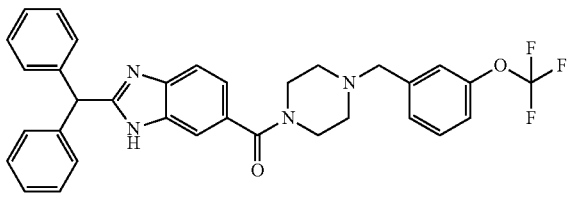

(E34)

Procedure:

The title compound was prepared from (16) (0.02 g, 0.06 mmol, 1 equiv) and 1-[3-(trifluoromethoxy)-benzyl]piperazine (0.015 mL, 0.07 mmol, 1.1 equiv) following the general procedure 7. Compound (E34) (0.034 g, 98%) was obtained as a yellow solid.

Characterization:

$^1$H NMR: (250 MHz, CDCl$_3$) δ 10.20 (d, J=67.9 Hz, 1H, NH), 7.83-7.30 (m, 6H), 7.26-6.91 (m, 11H), 5.78 (s, 1H, CH), 3.84-3.43 (m, 6H, CH$_2$), 2.57-2.37 (m, 4H, CH$_2$).

$^{13}$C NMR: (101 MHz, CDCl$_3$) δ 171.14, 160.89, 149.56, 140.46, 129.82, 129.78, 129.01, 128.96, 127.44, 127.32, 127.24, 121.39, 119.81, 119.33, 62.27 (CH$_2$), 53.47 (CH$_2$), 52.41 (CH$_2$), 52.00 (CH), 45.78 (CH$_2$), 40.10 (CH$_2$).

HRMS (ESI): m/z [M+H]$^+$ calcd for C$_{33}$H$_{30}$F$_3$N$_4$O$_2$ 571.2315 found 571.2312.

IR (cm$^{-1}$): 2922, 1611, 1489, 1443, 1302, 1255, 1213, 1150, 1002, 746, 699, 633, 614.

Mp: 76° C.

R$_f$: 0.65 (CH$_2$Cl$_2$/MeOH 9:1)

Example 35: Synthesis of N1-[3-(trifluoromethoxy) benzyl]-N4-[2-(3-pyridyl)-benzimidazole-5-carbonyl]-piperazine (E35)

(E35)

Procedure:

The title compound was prepared from (17) (0.05 g, 0.21 mmol, 1 equiv) and 1-[3-(trifluoromethoxy)-benzyl]piperazine (0.05 mL, 0.23 mmol, 1.1 equiv) following the general procedure 7. Compound (E35) (0.095 g, 94%) was obtained as a white solid.

Characterization:

$^1$H NMR: (250 MHz, CDCl$_3$) δ 13.27 (s, 1H, NH), 9.37 (d, J=1.6 Hz, 1H), 8.60 (dd, J=4.7, 1.1 Hz, 1H), 8.40 (d, J=8.0 Hz, 1H), 7.71 (bs, 1H), 7.46-6.93 (m, 7H), 3.95-3.43 (m, 6H, CH$_2$), 2.50 (bs, 4H, CH$_2$).

$^{13}$C NMR: (101 MHz, CDCl$_3$) δ 171.56, 150.64, 149.54, 149.52, 147.99, 140.32, 134.63, 129.78, 127.27, 126.36, 123.88, 121.85, 121.32, 119.81, 119.30, 62.12 (CH$_2$), 53.53 (CH$_2$), 53.26 (CH$_2$), 48.23 (CH$_2$), 42.68 (CH$_2$).

HRMS (ESI): m/z [M+H]+ calcd for $C_{25}H_{23}F_3N_5O_2$ 482.1798 found 482.1792.
IR (cm$^{-1}$): 1602, 1439, 1255, 1212, 1149, 1024, 1002, 810, 703, 633.
M 104° C.
R$_f$: 0.49 (CH$_2$Cl$_2$/MeOH 9:1)

Example 36: Synthesis of N1-[3-(trifluoromethoxy)benzyl]-N4-[2-(2-pyridyl)-benzimidazole-5-carbonyl]-piperazine (E36)

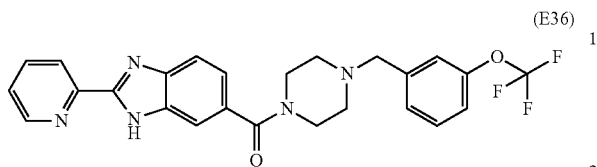

Procedure:
The title compound was prepared from (8) (0.05 g, 0.21 mmol, 1 equiv) and 1-[3-(trifluoromethoxy)-benzyl]piperazine (0.05 mL, 0.23 mmol, 1.1 equiv) following the general procedure 7. Compound (E36) (0.08 g, 80%) was obtained as a white solid.
Characterization:
$^1$H NMR: (400 MHz, CDCl$_3$) δ 11.07 (d, J=21.8 Hz, 1H, NH), 8.66 (d, J=4.4 Hz, 1H), 8.46 (d, J=6.9 Hz, 1H), 8.04-7.79 (m, 2H), 7.70-7.48 (m, 1H), 7.47-7.32 (m, 3H), 7.25 (s, 2H), 7.13 (d, J=7.9 Hz, 1H), 4.26-3.17 (m, 6H, CH$_2$), 2.50 (bs, 4H, CH$_2$).
$^{13}$C NMR: (101 MHz, CDCl$_3$) δ 170.90, 170.77, 152.25, 149.57, 149.37, 148.04, 140.48, 137.54, 129.77, 127.33, 125.09, 123.80, 121.98, 121.41, 120.05, 119.80, 119.24, 111.69, 111.10, 100.13, 62.33 (CH$_2$), 53.24 (CH$_2$).
HRMS (ESI): m/z [M+H]+ calcd for $C_{25}H_{23}F_3N_5O_2$ 482.1798 found 482.1792.
IR (cm$^{-1}$): 1619, 1449, 1263, 1212, 1259, 691.
Mp: 100° C.
R$_f$: 0.43 (CH$_2$Cl$_2$/MeOH 9:1)

Example 37: Synthesis of N1-[4-(trifluoromethoxy)benzyl]-N4-[(2-phenyl-benzimidazol-5-yl)methyl]-piperazine (E37)

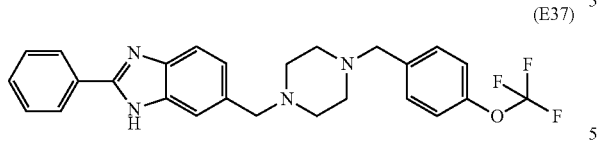

Procedure:
The title compound was prepared from (3) (0.05 g, 0.22 mmol, 1 equiv) and 1-[4-(trifluoromethoxy)-benzyl]piperazine (0.05 mL, 0.22 mmol, 1 equiv) following the general procedure 6. Compound (E37) (0.10 g, 98%) was obtained as an amorphous creamy solid.
Characterization:
$^1$H NMR: (400 MHz, CDCl$_3$) δ 8.23-8.11 (m, 2H), 7.54 (bs, 2H), 7.39-7.28 (m, 5H), 7.18 (d, J=8.8 Hz, 1H), 7.13 (d, J=8.2 Hz, 2H), 3.60 (s, 2H, CH$_2$), 3.45 (s, 2H, CH$_2$), 2.60-2.29 (m, 8H, CH$_2$).
$^{13}$C NMR: (101 MHz, CDCl$_3$) δ 152.63, 148.31, 136.98, 136.33, 131.88, 130.40, 130.32, 130.17, 130.02, 129.01, 127.03, 124.47, 121.84, 120.95, 120.79, 119.28, 63.25 (CH$_2$), 62.09 (CH$_2$), 52.89 (CH$_2$), 52.82 (CH$_2$).
HRMS (ESI): m/z [M+H]+ calcd for $C_{26}H_{26}F_3N_4O$ 467.2053 found 467.2053.
IR (cm$^{-1}$): 2811, 1508, 1457, 1255, 1220, 1154, 1009, 810, 779, 698.
R$_f$: 0.5 (CH$_2$Cl$_2$/MeOH 9:1)

Example 38: Synthesis of N1-[(2-benzhydryl-benzimidazol-5-yl)methyl]-piperazine-N4-[4-(trifluoromethoxy)benzyl]-piperazine (E38)

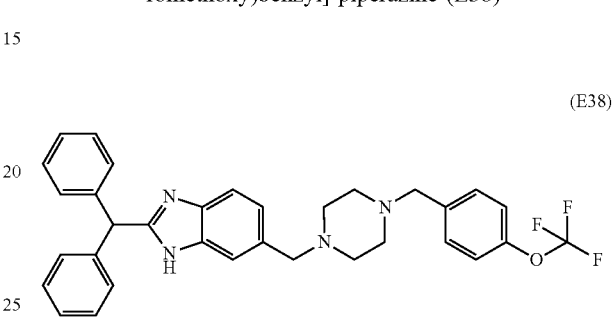

Procedure:
The title compound was prepared from (5) (0.05 g, 0.16 mmol, 1 equiv) and 1-[4-(trifluoromethoxy)-benzyl]piperazine (0.034 mL, 0.16 mmol, 1 equiv) following the general procedure 6. Compound (E38) (0.056 g, 64%) was obtained as an amorphous creamy solid.
Characterization:
$^1$H NMR: (400 MHz, CDCl$_3$) δ 9.42 (s, 1H, NH), 7.69-7.27 (m, 10H), 7.24-7.10 (m, 7H), 5.80 (s, 1H, CH), 3.65 (s, 2H, CH$_2$), 3.51 (s, 2H, CH$_2$), 2.50 (s, 8H, CH$_2$).
$^{13}$C NMR: (101 MHz, CDCl$_3$) δ 155.55, 148.40, 140.65, 136.89, 130.50, 129.52, 129.01, 127.98, 127.46, 120.85, 119.33, 63.09 (CH$_2$), 62.10 (CH$_2$), 52.79 (CH$_2$), 51.96 (CH$_2$) HRMS (ESI): m/z [M+H]+ calcd for $C_{33}H_{32}F_3N_4O$ 557.2523 found 557.2514.
IR (cm$^{-1}$): 2811, 1507, 1495, 1454, 1256, 1220, 1155, 1009, 805, 734, 698.
R$_f$: 0.48 (CH$_2$Cl$_2$/MeOH 9:1)

Example 39: Synthesis of N1-[4-(trifluoromethoxy)benzyl]-N4-[[2-(3-pyridyl)-benzimidazol-5-yl]methyl]-piperazine (E39)

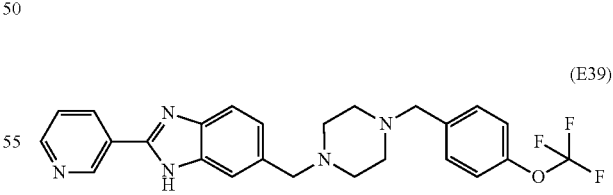

Procedure:
The title compound was prepared from (7) (0.04 g, 0.18 mmol, 1 equiv) and 1-[4-(trifluoromethoxy)-benzyl]piperazine (0.04 mL, 0.18 mmol, 1 equiv) following the general procedure 6. Compound (E39) (0.065 g, 78%) was obtained as a yellow solid.
Characterization:
$^1$H NMR: (400 MHz, CDCl$_3$) δ 12.50 (s, 1H, NH), 9.32 (d, J=1.7 Hz, 1H), 8.60 (dd, J=4.8, 1.5 Hz, 1H), 8.50-8.39

(m, 1H), 7.70 (s, 1H), 7.52-7.29 (m, 4H), 7.21 (dd, J=8.3, 1.2 Hz, 1H), 7.15 (d, J=7.9 Hz, 2H), 3.61 (s, 2H, CH$_2$), 3.48 (s, 2H, CH$_2$), 2.70-2.22 (m, 8H, CH$_2$).

$^{13}$C NMR: (101 MHz, CDCl$_3$) δ 150.27, 149.24, 148.37, 147.20, 137.09, 134.75, 130.41, 126.92, 124.31, 121.89, 120.85, 63.30 (CH$_2$), 62.20 (CH$_2$), 53.12 (CH$_2$).

HRMS (ESI): m/z [M+H]$^+$ calcd for C$_{25}$H$_{25}$F$_3$N$_5$O 468.2006 found 468.2001.

IR (cm$^{-1}$): 2811, 1508, 1255, 1219, 1155, 1009, 810, 706.

Mp: 88° C.

R$_f$: 0.43 (CH$_2$Cl$_2$/EtOH 8:2)

Example 40: Synthesis of N1-[4-(trifluoromethoxy)benzyl]-N4-[[2-(2-pyridyl)-benzimidazol-5-yl]methyl]piperazine (E40)

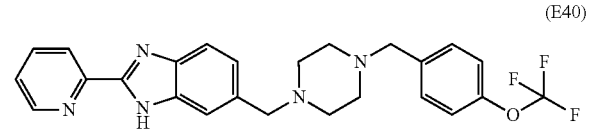 [SMILES: FC(F)(F)Oc1ccc(CN2CCN(Cc3ccc4nc(-c5ccccn5)[nH]c4c3)CC2)cc1]

(E40)

Procedure:

The title compound was prepared from (10) (0.05 g, 0.22 mmol, 1 equiv) and 1-[4-(trifluoromethoxy)-benzyl]piperazine (0.046 mL, 0.22 mmol, 1 equiv) following the general procedure 6. Compound (E40) (0.066 g, 63%) was obtained as a yellow solid.

Characterization:

$^1$H NMR: (400 MHz, CDCl$_3$) δ 11.02 (d, J=48.3 Hz, 1H, NH), 8.64 (d, J=4.4 Hz, 1H), 8.46 (d, J=7.9 Hz, 1H), 7.88 (td, J=7.8, 1.3 Hz, 1H), 7.78 (bs, 1H), 7.46-7.30 (m, 4H), 7.27 (s, 1H), 7.16 (d, J=8.0 Hz, 2H), 3.67 (s, 2H, CH$_2$), 3.51 (s, 2H, CH$_2$), 2.51 (bs, 8H, CH$_2$).

$^{13}$C NMR: (101 MHz, CDCl$_3$) δ 151.12, 149.21, 148.50, 148.35, 137.43, 137.14, 130.45, 124.65, 121.75, 120.83, 119.33, 63.38 (CH$_2$), 62.25 (CH$_2$), 53.15 (CH$_2$).

HRMS (ESI): m/z [M+H]$^+$ calcd for C$_{25}$H$_{25}$F$_3$N$_5$O 468.2006 found 468.1999.

IR (cm$^{-1}$): 1507, 1447, 1255, 1220, 1156, 1009, 795, 743, 699, 620.

Mp: 64° C.

R$_f$: 0.27 (CH$_2$Cl$_2$/MeOH 9:1)

Example 41: Synthesis of N1-[4-(trifluoromethoxy)benzyl]-N4-(2-phenyl-benzimidazole-5-carbonyl)-piperazine (E41)

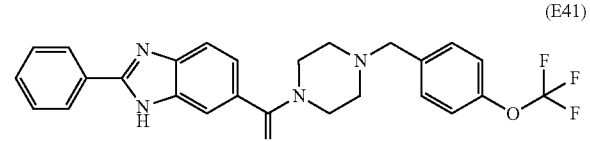

(E41)

Procedure:

The title compound was prepared from (15) (0.05 g, 0.21 mmol, 1 equiv) and 1-[4-(trifluoromethoxy)-benzyl]piperazine (0.048 mL, 0.23 mmol, 1.1 equiv) following the general procedure 7. Compound (E41) (0.084 g, 84%) was obtained as an amorphous creamy solid.

Characterization:

$^1$H NMR: (400 MHz, CDCl$_3$) δ 12.49 (s, 1H, NH), 8.17-7.97 (m, 2H), 7.84-7.29 (m, 7H), 7.18 (d, J=7.9 Hz, 3H), 3.82 (bs, 2H, CH$_2$), 3.51 (s, 4H, CH$_2$), 2.60-2.10 (m, 4H, CH$_2$).

$^{13}$C NMR: (101 MHz, CDCl$_3$) δ 171.62, 148.55, 136.56, 130.39, 129.72, 129.28, 128.98, 127.06, 121.01, 62.05.

HRMS (ESI): m/z [M+H]$^+$ calcd for C$_{26}$H$_{24}$F$_3$N$_4$O$_2$ 481.1846 found 481.1840.

IR (cm$^{-1}$): 1602, 1436, 1277, 1253, 1220, 1158, 1004, 841, 778, 769, 691, 674.

R$_f$: 0.57 (CH$_2$Cl$_2$/MeOH 9:1)

Example 42: Synthesis of N1-(2-benzhydryl-benzimidazole-5-carbonyl)-N4-[4-(trifluoromethoxy)benzyl]-piperazine (E42)

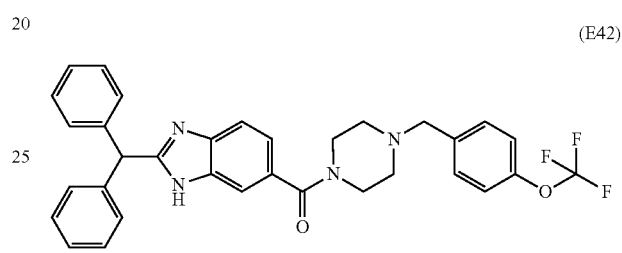

(E42)

Procedure:

The title compound was prepared from (16) (0.02 g, 0.06 mmol, 1 equiv) and 1-[4-(trifluoromethoxy)-benzyl]piperazine (0.015 mL, 0.07 mmol, 1.1 equiv) following the general procedure 7. Compound (E42) (0.028 g, 81%) was obtained as a white solid.

Characterization:

$^1$H NMR: (400 MHz, CDCl$_3$) δ 10.32 (bs, 1H, NH), 7.77-7.32 (m, 4H), 7.31-7.23 (m, 6H), 7.21-7.03 (m, 7H), 5.74 (s, 1H, CH), 3.95-3.29 (m, 6H, CH$_2$), 2.59-2.19 (m, 4H, CH$_2$).

$^{13}$C NMR: (101 MHz, CDCl$_3$) δ 171.17, 148.53, 140.45, 136.57, 130.40, 129.00, 128.94, 127.42, 121.00, 62.12 (CH$_2$), 51.97 (CH).

HRMS (ESI): m/z [M+H]$^+$ calcd for C$_{33}$H$_{30}$F$_3$N$_4$O$_2$ 571.2315 found 571.2313.

IR (cm$^{-1}$): 1606, 1435, 1256, 1220, 1151, 1001, 699.

Mp: 120° C.

R$_f$: 0.49 (CH$_2$Cl$_2$/MeOH 9:1)

Example 43: Synthesis of N1-[4-(trifluoromethoxy)benzyl]-N4-[2-(3-pyridyl)-benzimidazole-5-carbonyl]-piperazine (E43)

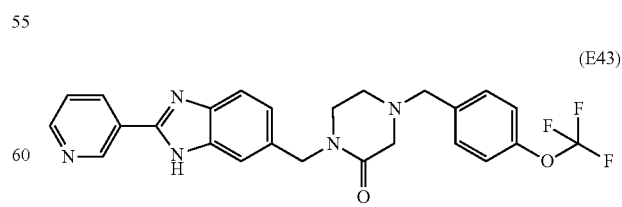

(E43)

Procedure:

The title compound was prepared from (17) (0.05 g, 0.21 mmol, 1 equiv) and 1-[4-(trifluoromethoxy)-benzyl]piperazine (0.048 mL, 0.23 mmol, 1.1 equiv) following the general procedure 7. Compound (E43) (0.085 g, 85%) was obtained as an amorphous creamy solid.

Characterization:

$^1$H NMR: (400 MHz, CDCl$_3$) δ 13.10 (s, 1H, NH), 9.36 (d, J=1.6 Hz, 1H), 8.62 (dd, J=4.8, 1.4 Hz, 1H), 8.48-8.35 (m, 1H), 7.86-7.27 (m, 5H), 7.19 (d, J=7.9 Hz, 3H), 3.81 (bs, 2H, CH$_2$), 3.51 (s, 4H, CH$_2$), 2.47 (bs, 4H, CH$_2$)

$^{13}$C NMR: (101 MHz, CDCl$_3$) δ 171.57, 151.32, 150.72, 148.58, 148.00, 136.46, 134.68, 130.39, 129.56, 126.36, 123.91, 121.88, 121.02, 119.32, 62.01 (CH$_2$).

HRMS (ESI): m/z [M+H]$^+$ calcd for C$_{25}$H$_{23}$F$_3$N$_5$O$_2$ 482.1798 found 482.1794.

IR (cm$^{-1}$): 1604, 1438, 1255, 1220, 1157, 816, 706.

R$_f$: 0.5 (CH$_2$Cl$_2$/MeOH 9:1)

Example 44: Synthesis of N1-[4-(trifluoromethoxy)benzyl]-N4-[2-(2-pyridyl)-benzimidazole-5-carbonyl]piperazine (E44)

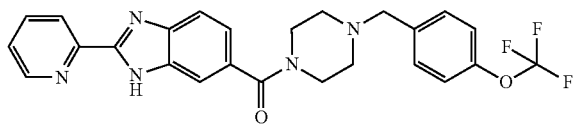
(E44)

Procedure:

The title compound was prepared from (8) (0.05 g, 0.21 mmol, 1 equiv) and 1-[4-(trifluoromethoxy)-benzyl]piperazine (0.05 mL, 0.23 mmol, 1.1 equiv) following the general procedure 7. Compound (E44) (0.079 g, 79%) was obtained as a white solid.

Characterization:

$^1$H NMR: (400 MHz, CDCl$_3$) δ 11.25 (bs, 1H, NH), 8.65 (d, J=4.2 Hz, 1H), 8.46 (d, J=7.8 Hz, 1H), 8.02-7.77 (m, 2H), 7.65-7.45 (m, 1H), 7.45-7.29 (m, 4H), 7.18 (d, J=7.8 Hz, 2H), 4.06-3.35 (m, 6H, CH$_2$), 2.49 (bs, 4H, CH$_2$).

$^{13}$C NMR: (101 MHz, CDCl$_3$) δ 149.34, 148.53, 148.07, 137.56, 136.60, 130.41, 125.08, 123.77, 121.95, 120.99, 119.21, 111.72, 62.16 (CH$_2$), 53.29 (CH$_2$).

HRMS (ESI): m/z [M+H]$^+$ calcd for C$_{25}$H$_{23}$F$_3$N$_5$O$_2$ 482.1798 found 482.1793.

IR (cm$^{-1}$): 1637, 1589, 1568, 1438, 1270, 1215, 1191, 1148, 1003, 835, 818, 796, 745, 694.

Mp: 190° C.

R$_f$: 0.5 (CH$_2$C2/MeOH 9:1)

Example 45: Synthesis of N1-[(2-phenyl-benzimidazol-5-yl)methyl]-N4-(p-tolylcarbamoyl)-piperazine (E45)

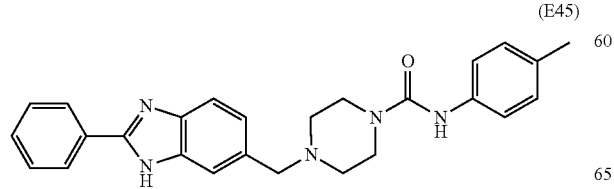
(E45)

Procedure:

1. Synthesis of Compound (19) N-tert-butoxycarbonyl-piperazine

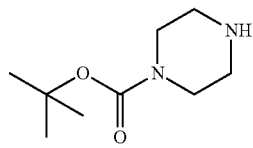
(33)

To a solution of 1,4-piperazine (2.25 g, 26.1 mmol, 1.5 equiv) in CH$_2$Cl$_2$ (50 mL) a solution of Boc$_2$O (3.80 g, 17.4 mmol, 1 equiv) in CH$_2$Cl$_2$ (25 mL) was slowly added. The reaction mixture was stirred at room temperature for 21 h, then concentrated. To the residue, water was added and the precipitated product was filtered off. The filtrate was extracted with CH$_2$Cl$_2$ (3×) and the combined organic phases were dried over MgSO$_4$ and concentrated to give (19) (1.82 g, 56%) as a white solid.

2. Synthesis of Compound (20) N1-tert-butoxycarbonyl-N4-(p-tolylcarbamoyl)-piperazine

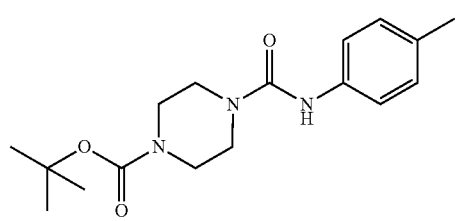
(20)

To a solution of (19) (0.4 g, 2.15 mmol, 1 equiv) in CH$_2$Cl$_2$ (12 mL) p-tolyl isocyanate (0.3 mL, 2.37 mmol, 1.1 equiv) was added. The reaction mixture was stirred under N$_2$, at room temperature for 2 h and then CH$_2$Cl$_2$ was added. The organic phase was washed with water and brine, then dried over MgSO$_4$ and concentrated. The crude product was purified by column chromatography (CH$_2$Cl$_2$/MeOH 96:4) to obtain the desired product (20) (0.675 g, 98%) as a creamy solid.

3. Synthesis of Compound (21) N1-(p-tolylcarbamoyl)piperazine

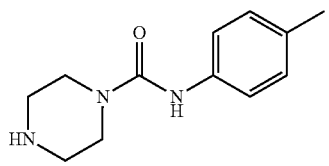
(21)

The title compound was prepared from (20) (0.65 g, 2.0 mmol, 1 equiv) and TFA (2.5 mL, 32 mmol, 16 equiv) following the general procedure 8, stirring reaction mixture for 1 h30 min in CH$_2$Cl$_2$ (10 mL). Compound (21) (0.45 g, quantitative) was obtained as a brown solid.

4. Synthesis of Compound (E45)

The title compound was prepared from (3) (0.04 g, 0.18 mmol, 1 equiv) and (21) (0.04 g, 0.18 mmol, 1 equiv) following the general procedure 6. Compound (E45) (0.060 g, 79%) was obtained as a white solid.

Characterization:

¹H NMR: (400 MHz, MeOD) δ 8.11 (dd, J=8.0, 1.4 Hz, 2H), 7.66-7.47 (m, 5H), 7.30 (d, J=8.3 Hz, 1H), 7.22 (d, J=8.4 Hz, 2H), 7.07 (d, J=8.3 Hz, 2H), 3.70 (s, 2H, CH$_2$), 3.60-3.47 (m, 4H, CH$_2$), 2.66-2.43 (m, 4H, CH$_2$), 2.28 (s, 3H, CH$_3$).

¹³C NMR: (101 MHz, MeOD) δ 158.12, 153.81, 138.12, 133.84, 131.40, 130.99, 130.16, 130.04, 127.79, 122.50, 64.17 (CH$_2$), 53.92 (CH$_2$), 44.93 (CH$_2$), 20.81 (CH$_3$).

HRMS (ESI): m/z [M+H]$^+$ calcd for C$_{26}$H$_{28}$N$_5$O 426.2288 found 426.2286.

IR (cm$^{-1}$): 1625, 1607, 1470, 1437, 1406, 991, 808, 801, 772, 703, 687.

Mp: 211° C.

R$_f$: 0.37 (CH$_2$Cl$_2$/MeOH 9:1)

Example 46: Synthesis of N1-[(2-benzhydryl-benzimidazol-5-yl)methyl]-N4-(p-tolylcarbamoyl)-piperazine (E46)

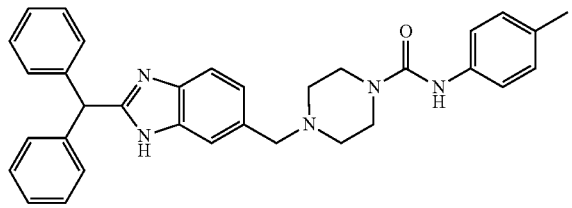

(E46)

Procedure:

The title compound was prepared from (5) (0.04 g, 0.13 mmol, 1 equiv) and (21) (0.03 g, 0.13 mmol, 1 equiv) following the general procedure 6. Compound (E46) (0.028 g, 43%) was obtained as an amorphous creamy solid.

Characterization:

¹H NMR: (250 MHz, CDCl$_3$) δ 7.53-7.33 (m, 2H), 7.23-7.03 (m, 13H), 6.97-6.87 (m, 2H), 5.66 (s, 1H, CH), 3.53 (s, 2H, CH$_2$), 3.45-3.27 (m, 4H, CH$_2$), 2.47-2.23 (m, 4H, CH$_2$), 2.14 (s, 3H, CH$_3$).

¹³C NMR: (63 MHz, MeOD) δ 158.09, 141.96, 138.10, 133.86, 130.45, 130.05, 130.02, 129.72, 129.64, 128.88, 128.24, 125.42, 122.49, 64.11 (CH$_2$), 53.81 (CH$_2$), 52.89 (CH), 44.79 (CH$_2$), 20.80 (CH$_3$).

HRMS (ESI): m/z [M+H]$^+$ calcd for C$_{33}$H$_{44}$N$_5$O 516.2758 found 516.2755.

IR (cm$^{-1}$): 1633, 1515, 1448, 1413, 1243, 1001, 803, 744, 698, 644, 611.

R$_f$ 0.53 (CH$_2$Cl$_2$/MeOH 9:1)

Example 47: Synthesis of N1-[[2-(3-pyridyl)-benzimidazol-5-yl]methyl]-N4-(p-tolylcarbamoyl)-piperazine (E47)

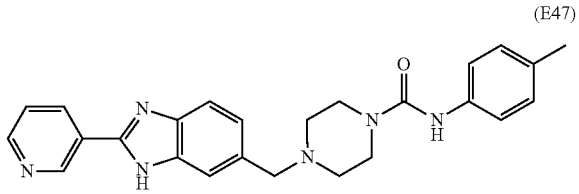 [SMILES: Cc1ccc(NC(=O)N2CCN(Cc3ccc4nc(-c5cccnc5)[nH]c4c3)CC2)cc1]

(E47)

Procedure:

The title compound was prepared from (7) (0.04 g, 0.18 mmol, 1 equiv) and (21) (0.04 g, 0.18 mmol, 1 equiv) following the general procedure 6. Compound (E47) (0.028 g, 36%) was obtained as a yellowish solid.

Characterization:

¹H NMR: (400 MHz, MeOD) δ 9.29 (d, J=1.6 Hz, 1H), 8.69 (dd, J=4.9, 1.4 Hz, 1H), 8.57-8.49 (m, 1H), 7.73-7.58 (m, 3H), 7.37 (d, J=8.2 Hz, 1H), 7.22 (d, J=8.4 Hz, 2H), 7.08 (d, J=8.2 Hz, 2H), 3.79 (s, 2H, CH$_2$), 3.62-3.52 (m, 4H, CH$_2$), 2.68-2.53 (m, 4H, CH$_2$), 2.29 (s, 3H, CH$_3$).

¹³C NMR: (101 MHz, MeOD) δ 151.42, 148.38, 138.10, 136.00, 133.89, 130.06, 125.68, 122.50, 63.96 (CH$_2$), 53.85 (CH$_2$), 44.80 (CH$_2$), 20.80 (CH$_3$).

HRMS (ESI): m/z [M+H]$^+$ calcd for C$_{25}$H$_{27}$N$_6$O 427.2241 found 427.2240.

IR (cm$^{-1}$): 2921, 1634, 1597, 1515, 1448, 1416, 1243, 1117, 1000, 810, 747, 704, 611.

Mp: 174° C.

R$_f$: 0.36 (CH$_2$Cl$_2$/MeOH 9:1)

Example 48: Synthesis of N1-[[2-(2-pyridyl)-benzimidazol-5-yl]methyl]-N4-(p-tolylcarbamoyl)-piperazine (E48)

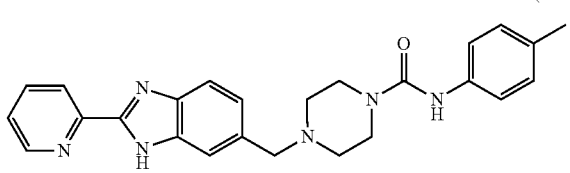

(E48)

Procedure:

The title compound was prepared from (10) (0.04 g, 0.18 mmol, 1 equiv) and (21) (0.04 g, 0.18 mmol, 1 equiv) following the general procedure 6. Compound (E48) (0.033 g, 43%) was obtained as a beige solid.

Characterization:

¹H NMR: (400 MHz, MeOD) δ 8.74 (d, J=3.6 Hz, 1H), 8.30 (d, J=7.9 Hz, 1H), 7.97 (t, J=7.6 Hz, 1H), 7.77-7.60 (m, 2H), 7.51-7.44 (m, 1H), 7.34 (d, J=8.0 Hz, 1H), 7.22 (d, J=8.4 Hz, 2H), 7.08 (d, J=8.2 Hz, 2H), 3.72 (s, 2H, CH$_2$), 3.60-3.50 (m, 4H, CH$_2$), 2.61-2.46 (m, 4H, CH$_2$), 2.28 (s, 3H, CH$_3$).

¹³C NMR: (101 MHz, MeOD) δ 158.12, 138.13, 133.83, 130.04, 125.95, 122.49, 64.14 (CH$_2$), 54.80 (CH$_2$), 53.93 (CH$_2$), 44.93 (CH$_2$), 20.80 (CH$_3$).

HRMS (ESI): m/z [M+H]+ calcd for C25H27N6O 427.2241 found 427.2239.

IR (cm−1): 1633, 1516, 1435, 1112, 1000, 189, 744, 697, 614.

Mp: 224° C.

Rf: 0.40 (CH2Cl2/MeOH 9:1)

Example 49: Synthesis of N1-[(2-phenyl-benzimidazol-5-yl)methyl]-N4-[[4-(trifluoromethyl)phenyl]carbamoyl]-piperazine (E49)

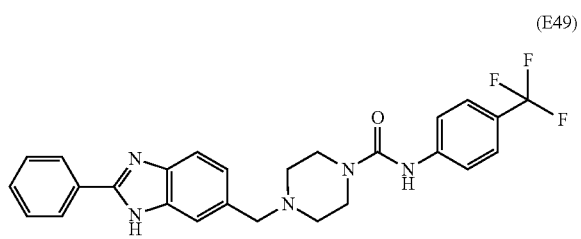 [SMILES: O=C(Nc1ccc(C(F)(F)F)cc1)N1CCN(Cc2ccc3nc(-c4ccccc4)[nH]c3c2)CC1]

(E49)

Procedure:

1. Synthesis of Compound (22) N1-tert-butoxycarbonyl-N4-[[4-(trifluoromethyl)phenyl]carbamoyl]-piperazine

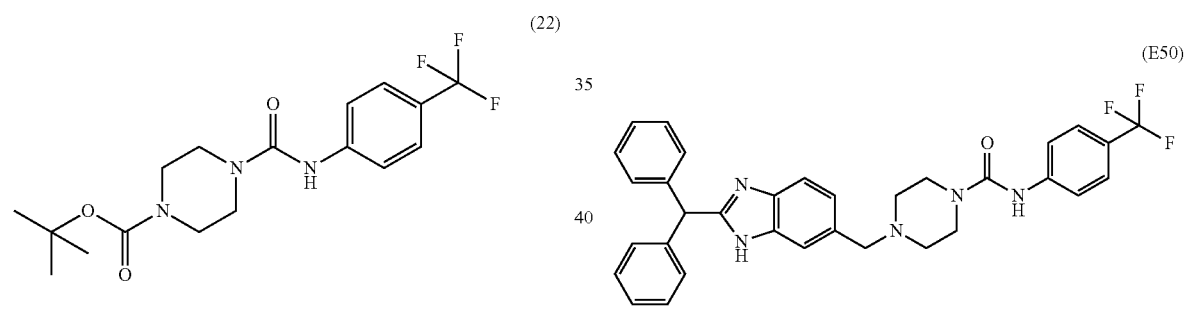

(22)

The title compound was prepared from (19) (0.40 g, 2.15 mmol, 1 equiv) and 4-(trifluoro methyl)-phenyl isocyanate (0.34 mL, 2.37 mmol, 1.1 eq). Compound (22) (0.778 g, 97%) was obtained as a white solid.

2. Synthesis of Compound (23) N-[[4-(trifluoromethyl)phenyl]carbamoyl]-piperazine

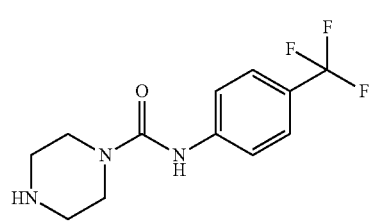

(23)

The title compound was prepared from (22) (0.770 g, 1.9 mmol, 1 equiv) and TFA (2.3 mL, 30 mmol, 16 equiv) following the general procedure 8, stirring reaction mixture for 2 h in CH2Cl2 (9.5 mL). Compound (23) (0.439 g, 85%) was obtained as a white solid.

3. Synthesis of Compound (E49)

The title compound was prepared from (3) (0.04 g, 0.18 mmol, 1 equiv) and (23) (0.049 g, 0.18 mmol, 1 equiv) following the general procedure 6. Compound (E49) (0.033 g, 38%) was obtained as a white solid.

Characterization:

1H NMR: (400 MHz, MeOD) δ 8.15-8.07 (m, 2H), 7.65-7.49 (m, 9H), 7.29 (dd, J=8.3, 1.0 Hz, 1H), 3.69 (s, 2H, CH2), 3.61-3.52 (m, 4H, CH2), 2.62-2.49 (m, 4H, CH2).

13C NMR: (101 MHz, MeOD) δ 157.17, 153.80, 144.86, 131.38, 130.97, 130.14, 127.79, 127.25, 126.71, 126.68, 125.75, 125.34, 125.01, 124.56, 120.93, 64.11 (CH2), 53.87 (CH2), 45.02 (CH2).

HRMS (ESI): m/z [M+H]+ calcd for C26H25F3N5O 480.2006 found 480.2003.

IR (cm−1): 1644, 1602, 1525, 1417, 1322, 1246, 1158, 1109, 1066, 1001, 834, 692, 612.

Mp: 174° C.

Rf: 0.45 (CH2Cl2/MeOH 9:1)

Example 50: Synthesis of N1-[(2-benzhydryl-benzimidazol-5-yl)methyl]-N4-[[4-(trifluoromethyl)phenyl]carbamoyl]-piperazine (E50)

(E50)

Procedure:

The title compound was prepared from (5) (0.04 g, 0.13 mmol, 1 equiv) and (23) (0.036 g, 0.13 mmol, 1 equiv) following the general procedure 6. Compound (E50) (0.039 g, 53%) was obtained as a beige solid.

Characterization:

1H NMR: (400 MHz, MeOD) δ 7.59-7.48 (m, 6H), 7.40-7.29 (m, 4H), 7.29-7.21 (m, 7H), 5.81 (s, 1H, CH), 3.65 (s, 2H, CH2), 3.58-3.48 (m, 4H, CH2), 2.55-2.42 (m, 4H, CH2).

13C NMR: (101 MHz, MeOD) δ 157.73, 157.13, 144.85, 141.94, 132.58, 130.46, 130.00, 129.94, 129.70, 129.61, 128.85, 128.21, 127.25, 126.72, 126.69, 125.35, 125.03, 120.93, 64.08 (CH2), 53.78 (CH2), 52.88 (CH), 44.95 (CH2).

HRMS (ESI): m/z [M+H]+ calcd for C33H31F3N5O 570.2475 found 570.2472.

IR (cm−1): 1645, 1445, 1416, 1322, 1245, 1161, 1110, 1067, 1001, 698.

Mp: 172° C.

Rf: 0.41 (CH2Cl2/MeOH 9:1)

Example 51: Synthesis of N1-[[2-(3-pyridyl)-benzimidazol-5-yl]methyl]-N4-[[4-(trifluoromethyl)phenyl]carbamoyl]-piperazine (E51)

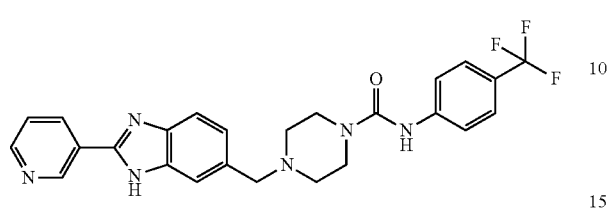

(E51)

Procedure:

The title compound was prepared from (7) (0.04 g, 0.18 mmol, 1 equiv) and (23) (0.049 g, 0.18 mmol, 1 equiv) following the general procedure 6. Compound (E51) (0.041 g, 48%) was obtained as an amorphous creamy solid.

Characterization:

$^1$H NMR: (400 MHz, MeOD) δ 9.28 (s, 1H), 8.67 (d, J=3.8 Hz, 1H), 8.54-8.37 (m, 1H), 7.62 (dd, J=7.5, 4.9 Hz, 3H), 7.55 (q, J=8.9 Hz, 4H), 7.34 (d, J=8.1 Hz, 1H), 3.72 (s, 2H, CH$_2$), 3.65-3.48 (m, 4H, CH$_2$), 2.64-2.21 (m, 4H, CH$_2$).

$^{13}$C NMR: (101 MHz, MeOD) δ 157.17, 151.35, 150.61, 148.34, 144.84, 135.94, 127.85, 127.25, 126.72, 126.69, 125.64, 125.36, 125.04, 124.56, 120.93, 64.02 (CH$_2$), 53.88 (CH$_2$), 45.03 (CH$_2$).

HRMS (ESI): m/z [M+H]$^+$ calcd for C$_{25}$H$_{24}$F$_3$N$_6$O 481.1958 found 481.1954.

IR (cm$^{-1}$): 1644, 1601, 1525, 1418, 1321, 1245, 1159, 1108, 1065, 1001, 818, 705.

R$_f$ 0.22 (CH$_2$Cl$_2$/MeOH 9:1)

Example 52: Synthesis of N1-[[2-(2-pyridyl)-benzimidazol-5-yl]methyl]-N4-[[4-(trifluoromethyl)phenyl]carbamoyl]-piperazine (E52)

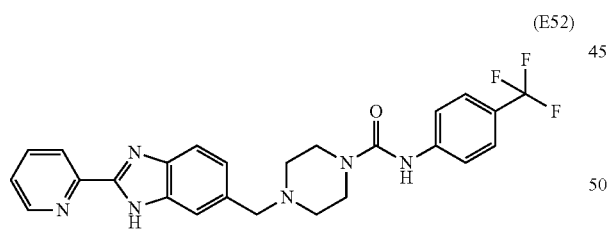

(E52)

Procedure:

The title compound was prepared from (10) (0.04 g, 0.18 mmol, 1 equiv) and (23) (0.049 g, 0.18 mmol, 1 equiv) following the general procedure 6. Compound (E52) (0.034 g, 40%) was obtained as an orange solid.

Characterization:

$^1$H NMR: (400 MHz, MeOD) δ 8.73 (d, J=3.3 Hz, 1H), 8.30 (d, J=7.9 Hz, 1H), 7.97 (t, J=7.7 Hz, 1H), 7.76-7.61 (m, 2H), 7.56 (dd, J=14.6, 8.8 Hz, 4H), 7.51-7.41 (m, 1H), 7.34 (d, J=8.1 Hz, 1H), 3.73 (s, 2H, CH$_2$), 3.64-3.54 (m, 4H, CH$_2$), 2.63-2.47 (m, 4H, CH$_2$).

$^{13}$C NMR: (101 MHz, MeOD) δ 157.20, 152.89, 150.90, 149.40, 144.87, 138.52, 127.26, 126.74, 126.70, 125.95, 122.51, 120.95, 64.10 (CH$_2$), 53.89 (CH$_2$), 45.03 (CH$_2$).

HRMS (ESI): m/z [M+H]$^+$ calcd for C$_{25}$H$_{24}$F$_3$N$_6$O 481.1958 found 481.1954.

IR (cm$^{-1}$): 1646, 1445, 1244, 1160, 1109, 1066, 998, 793, 630, 620.

Mp: 136° C.

R$_f$: 0.39 (CH$_2$Cl$_2$/MeOH 9:1)

Example 53: Synthesis of N1-[2-(4-chlorophenoxy)acetyl]-N4-[(2-phenyl-benzimidazol-5-yl)methyl]-piperazine (E53)

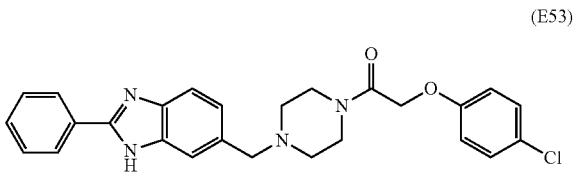 [SMILES: O=C(COc1ccc(Cl)cc1)N1CCN(Cc2ccc3nc(-c4ccccc4)[nH]c3c2)CC1]

(E53)

Procedure:

1. Synthesis of Compound (24) N1-tert-butoxycarbonyl-N4-[2-(4-chlorophenoxy) acetyl]-piperazine

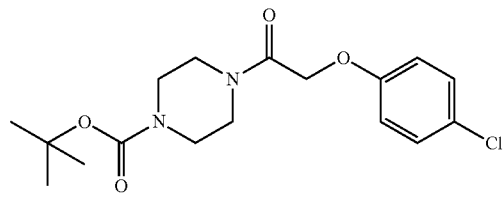

(24)

To a mixture of (19) (0.40 g, 2.15 mmol, 1 equiv) and Et$_3$N (0.45 mL, 3.23 mmol, 1.5 equiv) in CH$_2$Cl$_2$ (11 mL), 4-chlorophenoxyacetyl chloride (0.37 mL, 2.37 mmol, 1.1 equiv) was added. The reaction mixture was stirred overnight under N$_2$ atmosphere, then CH$_2$Cl$_2$ was added. The organic layer was washed with water and brine, then dried over MgSO$_4$ and concentrated under vacuum. Purification by column chromatography on silica gel (CH$_2$Cl$_2$/MeOH 97:3) gave (24) (0.74 g, 98%) as a brown solid.

2. Synthesis of Compound (25) N1-[2-(4-chlorophenoxy)acetyl]-piperazine

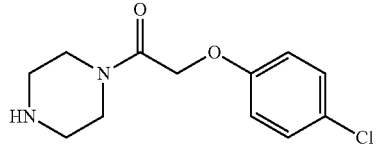

(25)

The title compound was prepared from (24) (0.72 g, 2.0 mmol) and TFA (0.6 mL) following the general procedure 8, stirring reaction mixture overnight in CH$_2$Cl$_2$ (10 mL). Compound (25) (0.50 g, 97%) was obtained as creamy oil.

3. Synthesis of Compound (E53)

The title compound was prepared from (3) (0.04 g, 0.18 mmol, 1 equiv) and (25) (0.046 g, 0.18 mmol, 1 equiv) following the general procedure 6. Compound (E53) (0.069 g, 84%) was obtained as a white solid.

Characterization:

$^1$H NMR: (400 MHz, CDCl$_3$) δ 8.15 (dd, J=6.5, 3.1 Hz, 2H), 7.60-7.42 (m, 2H), 7.42-7.32 (m, 3H), 7.25-7.11 (m, 3H), 6.87-6.75 (m, 2H), 4.67 (s, 2H, —OCH$_2$), 3.67-3.43 (m, 6H, CH$_2$), 2.52-2.31 (m, 4H, CH$_2$).

$^{13}$C NMR: (101 MHz, CDCl$_3$) δ 166.30, 156.49, 152.61, 132.14, 130.17, 130.08, 129.57, 129.08, 126.89, 126.72, 124.17, 116.03, 67.64 (OCH$_2$), 63.11 (CH$_2$), 53.09 (CH$_2$), 52.53 (CH$_2$), 45.40 (CH$_2$), 42.36 (CH$_2$).

HRMS (ESI): m/z [M+H]$^+$ calcd for C$_{26}$H$_{26}$ClN$_4$O$_2$ 461.1739 found 461.1737.

IR (cm$^{-1}$): 1644, 1448, 1221, 1000, 821, 779, 728, 695, 641.

M 104° C.

R$_f$: 0.55 (CH$_2$Cl$_2$/MeOH 9:1)

Example 54: Synthesis of N1-[(2-benzhydryl-benzimidazol-5-yl)methyl]-N4-[2-(4-chlorophenoxy)acetyl]-piperazine (E54)

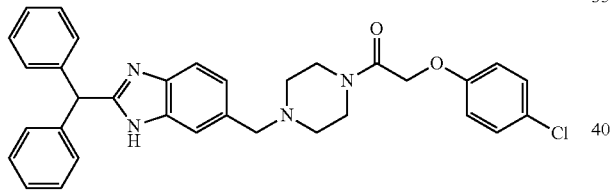

(E54)

Procedure:

The title compound was prepared from (5) (0.04 g, 0.13 mmol, 1 equiv) and (25) (0.03 g, 0.13 mmol, 1 equiv) following the general procedure 6. Compound (E54) (0.027 g, 38%) was obtained as a beige solid.

Characterization:

$^1$H NMR: (400 MHz, CDCl$_3$) δ 7.64-7.33 (m, 7H), 7.28-7.16 (m, 8H), 6.93-6.83 (m, 2H), 5.85 (s, 1H, CH), 4.66 (s, 2H, —OCH$_2$), 3.69-3.51 (m, 6H, CH$_2$), 2.46 (s, 4H, CH$_2$).

$^{13}$C NMR: (101 MHz, CDCl$_3$) δ 166.14, 156.59, 140.60, 129.63, 129.05, 129.01, 127.53, 126.73, 116.10, 67.93 (CH$_2$), 63.11 (CH$_2$), 53.08 (CH$_2$), 52.64 (CH$_2$), 52.04 (CH), 45.37 (CH$_2$), 42.22 (CH$_2$).

HRMS (ESI): m/z [M+H]$^+$ calcd for C$_{33}$H$_{32}$ClN$_4$O$_2$ 551.2208 found 551.2200.

IR (cm$^{-1}$): 1673, 1650, 1490, 1454, 1421, 1284, 1245, 999, 820, 743, 695, 640, 611.

Mp: 194° C.

R$_f$: 0.41 (CH$_2$Cl$_2$/MeOH 9:1)

Example 55: Synthesis of N1-[2-(4-chlorophenoxy)acetyl]-N4-[[2-(3-pyridyl)-benzimidazol-5-yl]methyl]-piperazine (E55)

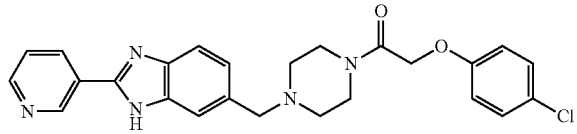

(E55)

Procedure:

The title compound was prepared from (7) (0.04 g, 0.18 mmol, 1 equiv) and (25) (0.046 g, 0.18 mmol, 1 equiv) following the general procedure 6. Compound (E55) (0.034 g, 41%) was obtained as an amorphous creamy solid.

Characterization:

$^1$H NMR: (400 MHz, CDCl$_3$) δ 12.03 (s, 1H, NH), 9.35 (s, 1H), 8.65 (d, J=4.1 Hz, 1H), 8.49 (d, J=8.0 Hz, 1H), 7.56 (s, 2H), 7.41 (dd, J=7.9, 4.8 Hz, 1H), 7.24-7.16 (m, 3H), 6.87-6.78 (m, 2H), 4.68 (s, 2H, CH$_2$), 3.69-3.52 (m, 6H, CH$_2$), 2.63-1.91 (m, 4H, CH$_2$).

$^{13}$C NMR: (101 MHz, CDCl$_3$) δ 166.35, 156.50, 150.52, 149.46, 147.47, 134.63, 129.61, 126.78, 124.20, 116.04, 67.70 (CH$_2$), 63.08 (CH$_2$), 53.15 (CH$_2$), 52.57 (CH$_2$), 45.40 (CH$_2$), 42.35 (CH$_2$).

HRMS (ESI): m/z [M+H]$^+$ calcd for C$_{25}$H$_{25}$ClN$_5$O$_2$ 462.1691 found 462.1690.

IR (cm$^{-1}$): 1644, 1490, 1441, 1222, 1000, 821, 728, 707, 640.

R$_f$ 0.34 (CH$_2$Cl$_2$/MeOH 9:1)

Example 56: Synthesis of N1-[2-(4-chlorophenoxy)acetyl]-N4-[[2-(2-pyridyl)-benzimidazol-5-yl]methyl]-piperazine (E56)

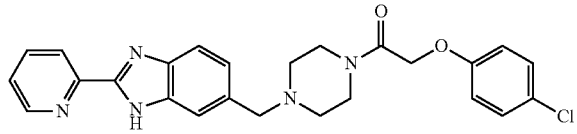

(E56)

Procedure:

The title compound was prepared from (10) (0.04 g, 0.18 mmol, 1 equiv) and (25) (0.046 g, 0.18 mmol, 1 equiv) following the general procedure 6. Compound (E56) (0.038 g, 46%) was obtained as a beige solid.

Characterization:

$^1$H NMR: (400 MHz, CDCl$_3$) δ 10.73 (bs, 1H, NH), 8.66 (d, J=4.6 Hz, 1H), 8.45 (d, J=7.9 Hz, 1H), 7.89 (td, J=7.9, 1.7 Hz, 1H), 7.82-7.76 (m, 1H), 7.49-7.43 (m, 1H), 7.42-7.37 (m, 1H), 7.27-7.20 (m, 2H), 6.89 (dd, J=8.9, 1.3 Hz, 2H), 4.68 (d, J=2.0 Hz, 2H, —OCH$_2$), 3.71-3.54 (m, 6H, CH$_2$), 2.48 (s, 4H, CH$_2$).

$^{13}$C NMR: (101 MHz, CDCl$_3$) δ 166.16, 156.63, 149.32, 148.38, 137.41, 129.62, 124.75, 124.22, 121.67, 120.56, 119.98, 116.12, 111.14, 68.00 (CH$_2$), 63.16 (CH$_2$), 53.08 (CH$_2$), 52.73 (CH$_2$), 45.53 (CH$_2$), 42.34 (CH$_2$).

HRMS (ESI): m/z [M+H]$^+$ calcd for C$_{25}$H$_{25}$ClN$_5$O$_2$ 462.1691 found 462.1690.

IR (cm$^{-1}$): 1651, 1595, 1490, 1445, 1221, 1171, 1146, 1093, 1075, 1040, 998, 823, 795, 695, 640, 612.

Mp: 138° C.

R$_f$: 0.43 (CH$_2$Cl$_2$/MeOH 9:1)

Example 57: Synthesis of N1-[2-[[4-(diethoxyphosphorylmethyl)phenyl]methoxy]phenyl]]-N4-[[2-[3-(trifluoromethyl)phenyl]-benzimidazol-5-yl]methyl]-piperazine

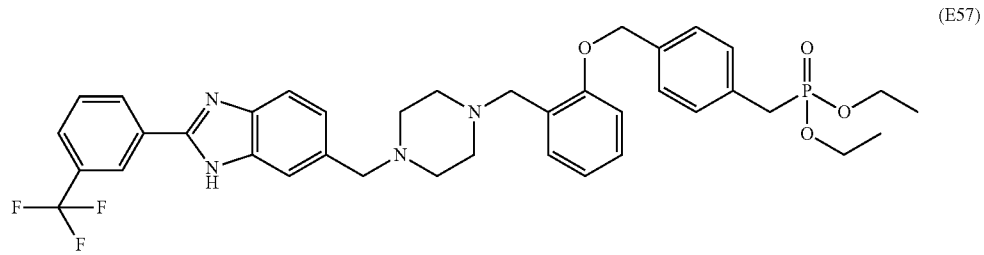 [SMILES: CCOP(=O)(Cc1ccc(COc2ccccc2CN2CCN(Cc3ccc4nc(-c5cccc(C(F)(F)F)c5)[nH]c4c3)CC2)cc1)OCC]
(E57)

Procedure:

1. Synthesis of Compound (26) diethyl 4-(bromomethyl)benzylphosphonate

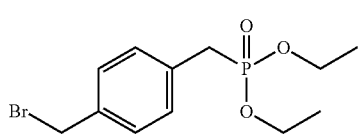
(26)

The title compound was prepared from α,α-dibromo-p-xylene (0.40 g, 1.5 mmol, 2 equiv) and triethyl phosphite (0.13 mL, 0.75 mmol, 1 equiv) following the general procedure 9. Compound (26) (0.21 g, 88%) was obtained as a colorless oil.

2. Synthesis of Compound (27) 2-[[4-(diethoxyphosphorylmethyl)phenyl]methoxy]benzaldehyde

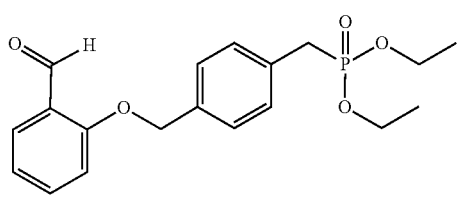
(27)

The title compound was prepared from (26) (0.13 g, 0.40 mmol, 1 equiv) and salicylaldehyde (0.05 mL, 0.44 mmol, 1.1 equiv) following the general procedure 1. Compound (27) (0.14 g, 94%) was obtained as a colorless oil.

3. Synthesis of Compound (E57)

The title compound was prepared from (E6) (0.06 g, 0.12 mmol, 1 equiv) and (27) (0.043 g, 0.12 mmol, 1 equiv) following the general procedure 2. Compound (E57) (0.027 g, 31%) was obtained as an amorphous white solid.

Characterization:

$^1$H NMR: (400 MHz, CDCl$_3$) δ 8.55 (s, 1H), 8.46 (d, J=7.4 Hz, 1H), 7.70-7.36 (m, 6H), 7.33 (s, 3H), 7.25-6.88 (m, 4H), 4.98 (s, 2H, CH$_2$), 4.13-3.93 (m, 4H, CH$_2$), 3.70 (s, 4H, CH$_2$), 3.23 (d, J=21.7 Hz, 2H, CH$_2$), 2.62 (bs, 8H, CH$_2$), 1.26 (t, J=7.0 Hz, 6H, CH$_3$).

$^{13}$C NMR: (101 MHz, CDCl$_3$) δ 157.22, 150.86, 135.79, 131.42, 131.05, 130.96, 130.09, 129.94, 129.88, 129.26, 127.94, 123.64, 120.97, 111.90, 69.95 (CH$_2$), 62.54 (CH$_2$), 62.47 (CH$_2$), 62.39 (CH$_2$), 55.61 (CH$_2$), 52.07 (CH$_2$), 51.74 (CH$_2$), 34.10 (CH$_2$), 32.72 (CH$_2$), 16.39 (CH$_3$), 16.33 (CH$_3$).

$^{19}$F NMR: (376 MHz, CDCl$_3$) δ -62.62. $^{31}$P NMR: (162 MHz, CDCl$_3$) δ 26.18.

HRMS (ESI): m/z [M+H]$^+$ calcd for C$_{38}$H$_{43}$F$_3$N$_4$O$_4$P 707.2969 found 707.2962.

IR (cm$^{-1}$): 2931, 1814, 1455, 1328, 1225, 1165, 1124, 1165, 1124, 1071, 1050, 1021, 964, 849, 810, 754, 720, 700.

R$_f$: 0.41 (CH$_2$Cl$_2$/MeOH 9:1)

Example 58: Synthesis of N1-[2-[[4-(diethoxyphosphorylmethyl)phenyl]methoxy]phenyl]]-N4-[[2-[4-(trifluoromethyl)phenyl]-benzimidazol-5-yl]methyl]-piperazine (E58)

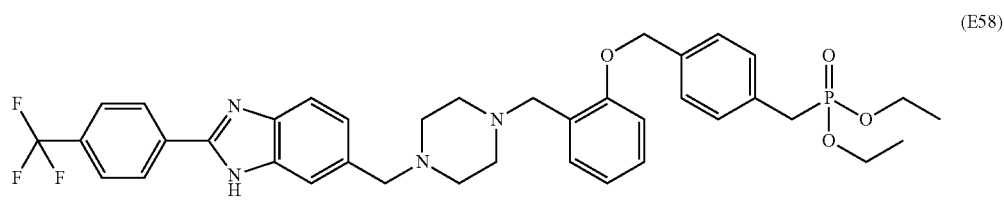 [SMILES: CCOP(=O)(Cc1ccc(COc2ccccc2CN2CCN(Cc3ccc4nc(-c5ccc(C(F)(F)F)cc5)[nH]c4c3)CC2)cc1)OCC]
(E58)

Procedure:

The title compound was prepared from (E5) (0.10 g, 0.20 mmol, 1 equiv) and (27) (0.072 g, 0.20 mmol, 1 equiv) following the general procedure 2. Compound (E58) (0.040 g, 28%) was obtained as an amorphous creamy solid.

Characterization:

$^1$H NMR: (400 MHz, CDCl$_3$) δ 8.32 (s, 2H), 7.81-7.54 (m, 3H), 7.51-7.07 (m, 8H), 7.02-6.84 (m, 2H), 4.99 (s, 2H, CH$_2$), 4.18-3.90 (m, 4H, CH$_2$), 3.61 (s, 4H, CH$_2$), 3.23 (d, J=21.5 Hz, 2H, CH$_2$), 2.49 (s, 8H, CH$_2$), 1.35-1.17 (m, 6H, CH$_3$).

$^{13}$C NMR: (101 MHz, CDCl$_3$) δ 157.07, 150.64, 136.13, 136.10, 133.84, 131.31, 130.77, 130.68, 129.89, 129.82, 128.36, 127.75, 127.05, 125.70, 125.66, 125.29, 122.59, 120.81, 111.92, 69.80 (CH$_2$), 62.89 (CH$_2$), 62.49 (CH$_2$), 56.21 (CH$_2$), 52.97 (CH$_2$), 52.72 (CH$_2$), 33.40 (d, J=138.6 Hz, P—CH$_2$), 16.41 (CH$_3$), 16.36 (CH$_3$).

$^{19}$F NMR: (376 MHz, CDCl$_3$) δ −62.73. $^{31}$P NMR: (162 MHz, CDCl$_3$) 26.31.

HRMS (ESI): m/z [M+H]$^+$ calcd for C$_{38}$H$_{43}$F$_3$N$_4$O$_4$P 707.2969 found 707.2959.

IR (cm$^{-1}$): 2933, 2810, 1620, 1491, 1453, 1323, 1292, 1224, 1063, 1120, 1065, 1051, 1017, 963, 851, 830, 788, 752, 731, 695.

R$_f$: 0.41 (CH$_2$Cl$_2$/MeOH 9:1)

Example 59: Synthesis of N1-[2-[[3-(diethoxyphosphorylmethyl)phenyl]methoxy]phenyl]]-N4-[[2-[3-(trifluoromethyl)phenyl]-benzimidazol-5-yl]methyl]-piperazine (E59)

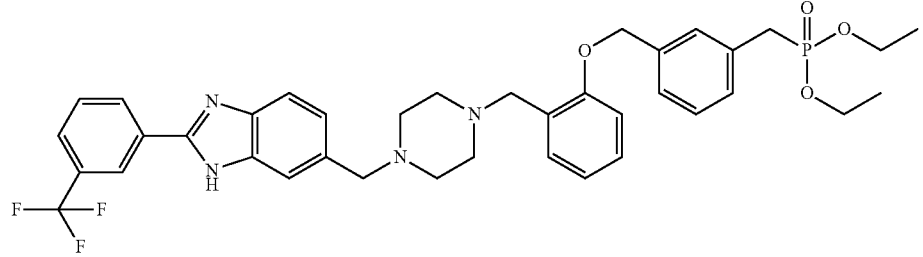

(E59)

Procedure.

1. Synthesis of Compound (28) diethyl 3-(bromomethyl)benzylphosphonate

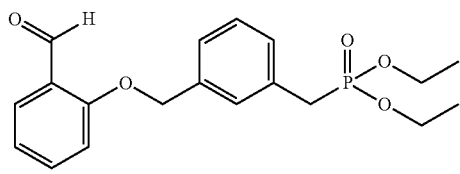

(28)

The title compound was prepared from α,α-dibromo-m-xylene (0.40 g, 1.5 mmol, 2 equiv) and triethyl phosphite (0.13 mL, 0.75 mmol, 1 equiv) following the general procedure 9.

Compound (28) (0.23 g, 94%) was obtained as a colorless oil.

2. Synthesis of Compound (29) 2-[[3-(diethoxy-phosphorylmethyl)phenyl]methoxy]benzaldehyde (29)

The title compound was prepared from (28) (0.18 g, 0.56 mmol, 1 eq) and salicylaldehyde (0.07 mL, 0.62 mmol, 1.1 equiv) following the general procedure 1. Compound (29) (0.19 g, 93%) was obtained as a colorless oil.

3. Synthesis of Compound (E59)

The title compound was prepared from (E6) (0.06 g, 0.12 mmol, 1 equiv) and (29) (0.043 g, 0.12 mmol, 1 equiv) following the general procedure 2. Compound (E59) (0.028 g, 33%) was obtained as an amorphous creamy solid.

Characterization:

$^1$H NMR: (400 MHz, CDCl$_3$) δ 8.53 (s, 1H), 8.44 (d, J=7.8 Hz, 1H), 7.70-7.63 (m, 1H), 7.63-7.48 (m, 3H), 7.44-7.32 (m, 2H), 7.29-7.20 (m, 4H), 7.13 (d, J=8.3 Hz, 1H), 7.03-6.84 (m, 2H), 5.01 (s, 2H, CH$_2$), 4.11-3.96 (m, 4H, CH$_2$), 3.76 (s, 2H CH$_2$), 3.68 (s, 2H CH$_2$), 3.23 (d, J=21.5 Hz, 2H, CH$_2$), 2.66 (bs, 8H, CH$_2$), 1.24 (t, J=7.1 Hz, 6H, CH$_3$).

$^{13}$C NMR: (101 MHz, CDCl$_3$) δ 157.05, 150.82, 137.44, 137.41, 132.00, 131.82, 131.72, 131.28, 131.08, 130.04, 129.31, 129.23, 129.17, 129.02, 128.79, 128.75, 128.70, 128.63, 126.13, 125.99, 125.34, 124.06, 123.59, 122.63, 120.95, 111.95, 69.82 (CH$_2$), 62.56 (CH$_2$), 62.49 (CH$_2$), 62.37 (CH$_2$), 55.26 (CH$_2$), 52.04 (CH$_2$), 51.96 (CH$_2$), 34.45 (CH$_2$), 33.08 (CH$_2$), 16.37 (CH$_3$), 16.31 (CH$_3$).

$^{19}$F NMR: (376 MHz, CDCl$_3$) δ −62.65. $^{31}$P NMR: (162 MHz, CDCl$_3$) δ 26.13.

HRMS (ESI): m/z [M+H]$^+$ calcd for C$_{38}$H$_{43}$F$_3$N$_4$O$_4$P 707.2969 found 707.2960.

IR (cm$^{-1}$): 2930, 2810, 1601, 1492, 1455, 1404, 1328, 1287, 1229, 1165, 1124, 1071, 1050, 1024, 965, 847, 807, 754, 697, 652.

R$_f$: 0.32 (CH$_2$Cl$_2$/MeOH 9:1)

Example 60: Synthesis of N1-[2-[[3-(diethoxyphosphorylmethyl)phenyl]methoxy]phenyl]]-N4-[[2-[4-(trifluoromethyl)phenyl]-benzimidazol-5-yl]methyl]-piperazine (E60)

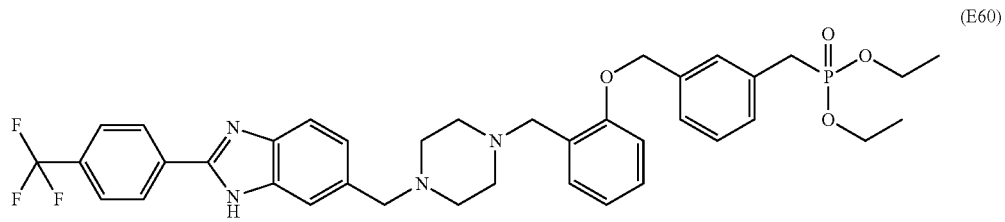 [SMILES: CCOP(=O)(Cc1cccc(COc2ccccc2CN2CCN(Cc3ccc4nc(-c5ccc(C(F)(F)F)cc5)[nH]c4c3)CC2)c1)OCC]

(E60)

Procedure:

The title compound was prepared from (E5) (0.10 g, 0.20 mmol, 1 equiv) and (29) (0.072 g, 0.20 mmol, 1 equiv) following the general procedure 2. Compound (E60) (0.035 g, 25%) was obtained as an amorphous creamy solid.

Characterization:

$^1$H NMR: (400 MHz, CDCl$_3$) δ 8.31 (d, J=5.8 Hz, 2H), 7.79-7.35 (m, 6H), 7.33-7.07 (m, 4H), 7.00-6.92 (m, 1H), 6.88 (d, J=8.0 Hz, 1H), 5.00 (s, 2H, CH$_2$), 4.14-3.95 (m, 4H, CH$_2$), 3.66 (s, 2H, CH$_2$), 3.62 (s, 2H, CH$_2$), 3.23 (d, J=21.4 Hz, 2H, P—CH$_2$), 2.55 (bs, 8H, CH$_2$), 1.25 (t, J=7.0 Hz, 6H, CH$_3$).

$^{13}$C NMR: (101 MHz, CDCl$_3$) δ 157.07, 150.66, 137.82, 137.79, 133.90, 131.81, 131.71, 131.12, 129.24, 129.18, 128.89, 128.68, 128.56, 127.08, 126.06, 125.83, 125.79, 125.43, 122.73, 120.96, 112.04, 69.86 (CH$_2$), 62.71 (CH$_2$), 62.64 (CH$_2$), 56.08 (CH$_2$), 53.08 (CH$_2$), 52.94 (CH$_2$), 33.89 (d, J=138.1 Hz, (P—CH$_2$), 16.54 (CH$_3$), 16.49 (CH$_3$).

$^{19}$F NMR: (376 MHz, CDCl$_3$) δ −62.74.

$^{31}$P NMR: (162 MHz, CDCl$_3$) δ 26.21.

HRMS (ESI): m/z [M+H]$^+$ calcd for C$_{38}$H$_{43}$F$_3$N$_4$O$_4$P 707.2969 found 707.2961.

IR (cm$^{-1}$): 2934, 2810, 1620, 1600, 1492, 1453, 1323, 1228, 1163, 1120, 1065, 1051, 1016, 964, 908, 850, 813, 788, 752, 729, 695.

R$_f$: 0.37 (CH$_2$Cl$_2$/MeOH 9:1)

Example 61: Synthesis of (E61) 6-[[4-[2-[[3-(diethoxyphosphorylmethyl)phenyl]-methoxy]phenoxy]-1-piperidyl]methyl]-2-phenyl-1H-benzimidazole

Procedure:

1) Synthesis of Compound (30) phenol, 2-[(tetrahydro-2H-pyran-2yl)oxy]

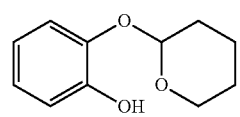

(30)

Catechol (2 g, 1 eq., 18.2 mmol) and dihydropyran (1.66 mL, 1 eq., 18.2 mmol) were introduced to a solution of pyridinium p-toluenesulfonate (46 mg, 1 mol %, 0.182 mmol) in DCM (35 mL). The solution was then stirred at room temperature for 3 hours, and the solvent were removed in vacuo. The resulted mixture was then dissolved in EtOAc, washed twice with NaHCO$_3$, once with brine, dried over MgSO$_4$. Compound (30) (3.30 g, 94%) was obtained as a light yellow oil.

2) Synthesis of Compound (31) 2-[2-[(3-diethoxyphosphorylphenyl)-methoxy]phenoxy]tetrahydropyran

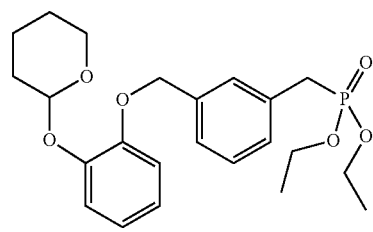

(31)

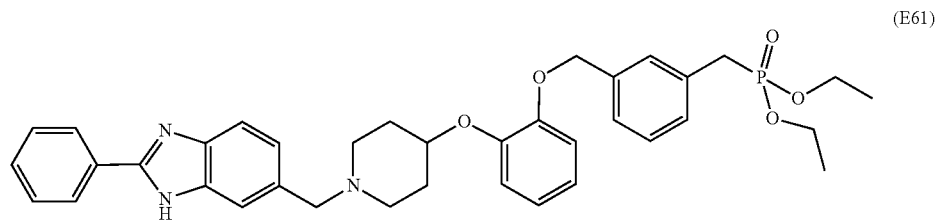 [SMILES: CCOP(=O)(Cc1cccc(COc2ccccc2OC2CCN(Cc3ccc4nc(-c5ccccc5)[nH]c4c3)CC2)c1)OCC]

(E61)

Compound (30) (665 mg, 1.1 eq., 3.43 mmol) was dissolved in N,N-dimethylformamide (10 mL) in a 10-20 mL microwave vial. To this solution was added potassium carbonate (868 mg., 2 eq., 6.28 mmol), compound (28) (1 g, 1 eq., 3.14 mmol) and few crystals of sodium iodide (catalytic amount). The solution was then stirred for 20 min. at 80° C. under microwave irradiation. After evaporation of all volatiles, the residue was purified by silica gel chromatography. Compound (31) was obtained as a colorless oil (974 mg, 72%).

3) Synthesis of Compound (32) 2-[2-[(3-diethoxy-phosphorylphenyl)methoxy]-phenoxy]tetrahydropyran

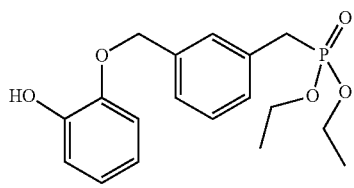

(32)

To a solution of compound (31) (1.60 g, 1 eq., 3.6 mmol) in ethanol (37 mL) was added pyridium p-toluenesulfonate (45 mg, 5 mol %, 0.18 mmol). The solution was then stirred at 55° C. during 3 hours, followed by the evaporation of all volatiles. The residue was then purified by flash chromatography, eluting Petroleum Ether/ethyl acetate 65:35 to 1:1. Compound (32) was obtained as a light brown oil (1.28 g, quantitative yield).

4) Synthesis of Compound (33) 1-(tert-butoxycarbonyl)-4-hydroxypiperidine

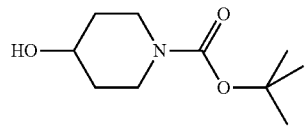

(33)

tert-butyl 4-oxopiperidine-1-carboxylate (5 g, 1 eq., 25.1 mmol) was dissolved in methanol (50 mL) under inert atmosphere. This solution was cooled down at 0° C., and sodium borohydride was subsequently added portionwise (950 mg, 1 eq., 25.1 mmol). The solution was allowed to reach room temperature and was stirred for 20 h. The solution was carefully quenched at 0° C. with 2N sodium hydroxide (20 mL), followed by evaporation of all volatiles. The mixture was then dissolved in ethyl acetate (40 mL) and water (20 mL), the aqueous phase was extracted three times with ethyl acetate (3×40 mL), the organic phase was washed with H$_2$O (20 mL), brine (20 mL), dried over MgSO$_4$ and concentrated under reduced pressure. The resulting mixture was purified by silica gel column chromatography (Petroleum Ether/EtOAc 8:2) to afforded compound (33) as a white solid (4.8 g, 95%).

5) Synthesis of Compound (34) 1-(tert-butoxycarbonyl)-4-(p-toluensulfonyloxy)-piperidine

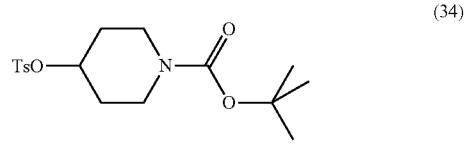 [SMILES: Cc1ccc(S(=O)(=O)OC2CCN(C(=O)OC(C)(C)C)CC2)cc1]

(34)

To a solution of compound (33) (5 g, 1 eq., 24.8 mmol) in dichloromethane (50 mL) was added triethylamine (13.9 mL, 4 eq., 99.4 mmol) and p-toluenesulfonyl chloride (9.47 g, 2 eq., 49.7 mmol). The solution was stirred for 20 h at room temperature followed by the concentration of this solution in vacuo. The residue was then dissolved in dichloromethane (20 mL) and water (20 mL), extracted with DCM (20 mL), washed with 1N HCl (40 mL), extracted twice with DCM (2×40 mL), dried over MgSO$_4$ and evaporated. The resulting mixture was then purified by silica gel column chromatography (Petroleum ether/EtOAc 8:2) and compound (34) was obtained as a white crystalline solid (8.7 g, quantitative yield).

6) Synthesis of Compound (35) tert-butyl 4-[2-[(3-diethoxyphosphorylphenyl)-methoxy]phenoxy]piperidine-1-carboxylate

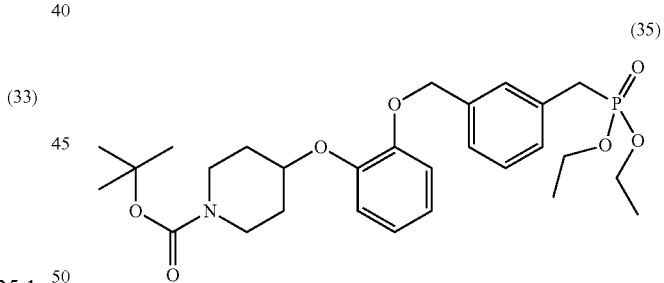

(35)

In a 2-5 mL microwave vial, compound (32) (100 mg, 1 eq., 0.29 mmol) was dissolved in dimethylacetamide (DMA, 2.5 mL). To this mixture was added potassium carbonate (81 mg, 2 eq., 0.57 mmol) and compound (34) (152 mg, 1.5 eq., 0.43 mmol), before being stirred at 140° C. during 30 min under microwave irradiation. The resulting residue was dissolved in ethyl acetate (10 mL) and water (5 mL), and the aqueous phase was extracted thrice with ethyl acetate (3×10 mL). The organic phase was then washed 5 times with water (5×5 mL), once with brine (5 mL) and dried over magnesium sulfate. The residue was concentrated under reduced pressure and purified by silica gel column chromatography, eluting dichloromethane/methanol 99:1, to afford compound (35) as colorless oil (100 mg, 71%).

7) Synthesis of Compound (36) 4-[2-[(3-diethoxy-phosphorylphenyl)methoxy]-phenoxy]piperidine

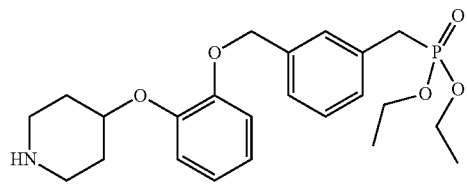
(36)

Following general procedure 11, trifluoroacetic acid (1.5 mL, 100 eq., 19.7 mmol) was added to a solution of compound (35) (105 mg, 1 eq., 0.197 mmol) in dichloromethane (3 mL). Pure compound (36) was obtained after flash column chromatography (DCM/MeOH 95:5), affording desired product as an orange solid (58 mg, 68%).

8) Synthesis of Compound (E61)

The title compound (E61) was obtained following the general procedure 12 from compound (3) (22 mg, 1 eq., 0.099 mmol), $SOCl_2$ (210 µL, 29 eq., 2.87 mmol), compound (36) (43 mg, 1 eq., 0.099 mmol), and diisopropylethylamine (90 µL, 5.3 eq., 0.53 mmol) in acetonitrile (3 mL). After purification by silica gel column chromatography, eluting dichloromethane/methanol 95:5, the clean compound (E61) was obtained as an amorphous creamy solid. (24 mg, 38%)

Characterization:

$^1$H NMR: (400 MHz, MeOD) δ 8.09 (d, J=7.2 Hz, 2H, $H^{Ar}$), 7.57 (m, 5H, $H^{Ar}$), 7.33 (m, 5H, $H^{Ar}$), 7.03 (m, 2H, $H^{Ar}$), 6.91 (m, 2H, $H^{Ar}$), 5.06 (s, 2H, $CH_2$—O), 4.43 (s, 1H, $H^4$ pip), 3.98 (ddq, J=8.0, 7.0, 1.0 Hz, 4H, $CH_2$—O—P), 3.84 (s, 2H, $CH_2$—N), 3.23 (d, J=21.7 Hz, 2H, $CH_2$—P), 2.99 (bs, 2H, $H^2$, $H^6$ pip), 2.62 (bs, 2H, $H^2$, $H^6$ pip), 1.97 (m, 4H, $H^3$, $H^5$ pip), 1.20 (td, J=7.0, 1.0 Hz, 6H, $CH_3$).

$^{13}$C NMR: (101 MHz, MeOD) δ 152.28 ($C^{quat}$), 150.16 ($C^{quat}$), 147.08 ($C^{quat}$), 137.88 (d, J=3.3 Hz, $C^{quat}$) 131.61 (d, J=9.4 Hz, $C^{quat}$) 130.13 ($C^{Ar}$) 129.47 ($C^{quat}$) 129.13 (d, J=6.6 Hz, $C^{Ar}$) 128.78 ($C^{Ar}$), 128.73 (d, J=7.0 Hz, $C^{Ar}$), 128.32 (d, J=3.4 Hz, $C^{Ar}$) 126.44 ($C^{Ar}$) 125.92 (d, J=3.7 Hz, $C^{Ar}$) 122.36 ($C^{Ar}$) 121.44 ($C^{Ar}$), 118.51 ($C^{Ar}$), 115.19 ($C^{Ar}$), 70.54 ($CH_2$—O), 62.35 (d, J=6.9 Hz, $CH_2$—O—P), 62.21 ($CH_2$—N), 49.29 ($C^2$, $C^6$ pip), 32.32 (d, J=137.7 Hz, $CH_2$—P), 29.41 (C3, $C^5$ pip), 15.25 (d, J=6.0 Hz, $CH_3$).

$^{31}$P NMR: (162 MHz, MeOD) δ 27.36.

HRMS-ESI (m/z) [M+H]$^+$ calculated for $C_{37}H_{43}N_3O_5P$ 640.2941, found 640.2938.

Example 62: Synthesis of (E62) 6-[[4-[2-[[3-(diethoxyphosphorylmethyl)phenyl]-methoxy]phenoxy]-1-piperidyl]methyl]-2-[4-(trifluoromethyl)phenyl]-1H-benzimidazole

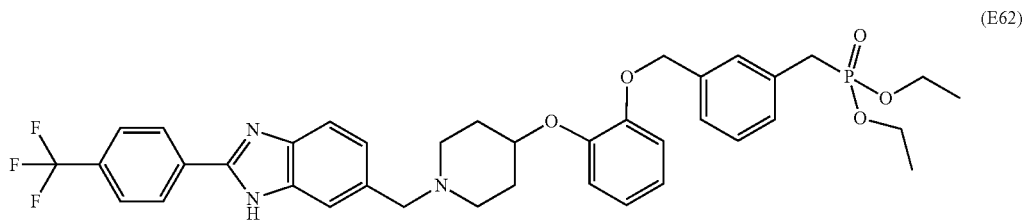 [SMILES: CCOP(=O)(Cc1cccc(COc2ccccc2OC2CCN(Cc3ccc4nc(-c5ccc(C(F)(F)F)cc5)[nH]c4c3)CC2)c1)OCC]
(E62)

Procedure:

The title compound (E62) was obtained following the general procedure 12 from compound (12) (34 mg, 1 eq., 0.115 mmol), $SOCl_2$ (243 µL, 29 eq., 3.35 mmol), compound (36) (50 mg, 1 eq., 0.115 mmol) and diisopropylethylamine (100 µL, 5.3 eq., 0.59 mmol) in acetonitrile (3 mL). After purification by silica gel column chromatography, eluting dichloromethane/methanol 95:5, the title compound (E62) was obtained as an amorphous creamy solid. (19 mg, 22%)

Characterization:

$^1$H NMR: (400 MHz, MeOD) δ 8.45 (bs, 1H, $H^{Ar}$), 8.36 (d, J=7.8 Hz, 1H, $H^{Ar}$), 7.83 (n, 1H, $H^{Ar}$), 7.78 (m, 1H, $H^{Ar}$), 7.63 (m, 2H, $H^{Ar}$), 7.42 (bs, 1H, $H^{Ar}$), 7.32 (m, 4H, $H^{Ar}$), 7.02 (m, 2H, $H^{Ar}$), 6.91 (m, 2H, $H^{Ar}$), 5.06 (s, 2H, $CH_2$—O), 4.42 (d, J=7.4 Hz, 1H, $H^4$ pip), 3.99 (m, 4H, $CH_2$—O—P), 3.80 (s, 2H, $CH_2$—N), 3.25 (d, J=21.7 Hz, 2H, $CH_2$—P), 2.94 (bs, 2H, $H^2$, $H^6$ pip), 2.55 (bs, 2H, $H^2$, $H^6$ pip), 1.96 (m, 4H, $H^3$, $H^5$ pip), 1.22 (t, J=7.1 Hz, 6H, $CH_3$).

$^{13}$C NMR: (101 MHz, MeOD) δ 150.87 ($C^{quat}$), 150.11 ($C^{quat}$), 147.19 ($C^{quat}$), 137.94 (d, J=3.0 Hz, $C^{quat}$) 131.58 (d, J=9.5 Hz, $C^{quat}$) 131.39 ($C^{quat}$), 131.06 ($C^{quat}$), 130.63 ($C^{quat}$) 129.83 ($C^{Ar}$) 129.82 ($C^{Ar}$) 129.77 ($C^{Ar}$), 129.09 (d, J=6.8 Hz, $C^{Ar}$), 128.71 (d, J=6.9 Hz, $C^{Ar}$), 128.30 (d, J=2.8 Hz, $C^{Ar}$) 126.40 ($C^{Ar}$) 125.89 (d, J=3.7 Hz, $C^{Ar}$), 125.36 ($C^{Ar}$) 123.06 ($C^{Ar}$) 122.23 ($C^{Ar}$), 121.45 ($C^{Ar}$) 118.38 ($C^{Ar}$), 115.28 ($C^{Ar}$), 70.56 ($CH_2$—O), 62.38 ($CH_2$—N), 62.34 (d, J=6.9 Hz, $CH_2$—O—P), 49.43 ($C^2$, $C^6$ pip), 32.28 (d, J=138.1 Hz, $CH_2$—P), 29.75 (C3, $C^5$ pip), 15.26 (d, J=6.0 Hz, $CH_3$).

$^{31}$P NMR: (162 MHz, MeOD) δ 27.36.

$^{19}$F NMR: (376 MHz, MeOD) δ −64.31.

HRMS-ESI (m/z) [M+H]$^+$ calculated for $C_{39}H_{42}F_3N_3O_5P$ 708.2811, found 708.2808.

Example 63: Synthesis of (E63) 6-[[4-[2-[[3-(di-ethoxyphosphorylmethyl)phenyl]-methoxy]phenoxy]-1-piperidyl]methyl]-2-[3-(trifluoromethyl)phenyl]-1H-benzimidazole

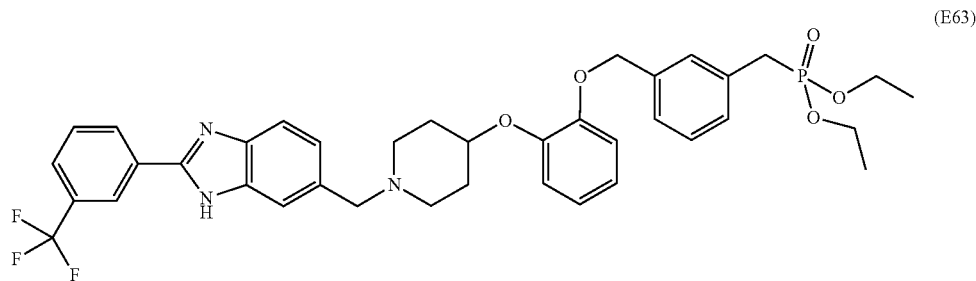 [SMILES: CCOP(=O)(Cc1cccc(COc2ccccc2OC2CCN(Cc3ccc4nc(-c5cccc(C(F)(F)F)c5)[nH]c4c3)CC2)c1)OCC]
(E63)

Procedure:

The title compound (E63) was obtained following the general procedure 12 from compound (14) (34 mg, 1 eq., 0.115 mmol), SOCl$_2$ (243 µL, 29 eq., 3.35 mmol), compound (36) (50 mg, 1 eq., 0.115 mmol), and diisopropylethylamine (100 µL, 5.3 eq., 0.59 mmol) in acetonitrile (3 mL). After purification by silica gel column chromatography, eluting dichloromethane/methanol 95:5, the clean compound (E63) was obtained as an amorphous creamy solid (20 mg, 24%).

Characterization:

$^1$H NMR: (400 MHz, MeOD) δ 8.40 (bs, 1H, H$^{Ar}$), 8.31 (d, J=7.9 Hz, 1H, H$^{Ar}$), 7.67 (n, 4H, H$^{Ar}$), 7.28 (m, 5H, H$^{Ar}$), 6.90 (m, 4H, H$^{Ar}$), 5.01 (s, 2H, CH$_2$—O), 4.36 (s, 1H, H$^4$ pip), 3.94 (ddq, J=8.0, 7.1, 1.0 Hz, 4H, CH$_2$—O—P), 3.71 (s, 2H, CH$_2$—N), 3.19 (d, J=21.7 Hz, 2H, CH$_2$—P), 2.86 (s, 2H, H$^2$, H$^6$ pip), 2.44 (d, J=8.7 Hz, 2H, H$^2$, H$^6$ pip), 1.91 (dd, J=12.9, 8.4 Hz, 4H, H$^3$, H$^5$ pip), 1.16 (dt, J=7.1, 1.0 Hz, 6H, CH$_3$).

$^{13}$C NMR: (101 MHz, MeOD) δ 150.79 (C$^{quat}$), 150.07 (C$^{quat}$), 147.25 (C$^{quat}$), 137.94 (d, J=3.2 Hz, C$^{quat}$) 131.57 (d, J=9.4 Hz, C$^{quat}$) 131.38 (C$^{quat}$), 131.06 (C$^{quat}$), 130.65 (C$^{quat}$) 129.81 (C$^{Ar}$) 129.79 (C$^{Ar}$), 129.07 (d, J=6.7 Hz, C$^{Ar}$), 128.70 (d, J=6.7 Hz, C$^{Ar}$) 128.29 (d, J=3.1 Hz, C$^{Ar}$) 126.37 (C$^{Ar}$), 125.88 (d, J=3.6 Hz, C$^{Ar}$) 123.08 (C$^{Ar}$), 122.15 (C$^{Ar}$) 121.45 (C$^{Ar}$) 118.31 (C$^{Ar}$), 115.31 (C$^{Ar}$), 70.57 (CH$_2$—O), 62.53 (CH$_2$—N), 62.34 (d, J=7.0 Hz, CH$_2$—O—P), 49.56 (C$^2$, C$^6$ pip), 32.29 (d, J=137.6 Hz, CH$_2$—P), 29.89 (C3, C$^5$ pip), 15.29, 15.26 (d, J=6.0 Hz, CH$_3$).

$^{31}$P NMR: (162 MHz, MeOD) δ 27.36.

$^{19}$F NMR: (376 MHz, MeOD) δ −64.31.

HRMS-ESI (m/z) [M+H]$^+$ calculated for C$_{39}$H$_{42}$F$_3$N$_3$O$_5$P 708.2811, found 708.2807.

Example 64: Synthesis of (E64) 6-[[4-[2-[[3-(di-ethoxyphosphorylmethyl)phenyl]-methoxy]phenoxy]-1-piperidyl]methyl]-2-[4-(trifluoromethoxy)phenyl]-1H-benzimidazole

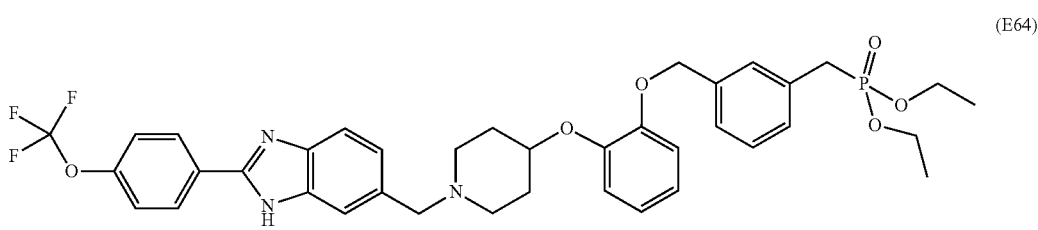 [SMILES: CCOP(=O)(Cc1cccc(COc2ccccc2OC2CCN(Cc3ccc4nc(-c5ccc(OC(F)(F)F)cc5)[nH]c4c3)CC2)c1)OCC]
(E64)

Procedure:

1. Synthesis of Compound (37) methyl 2-[4-(trifluoromethoxy)phenyl]-3H-benzimidazole-5-carboxylate

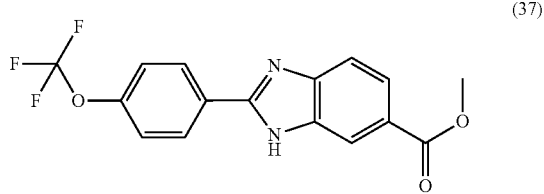 [SMILES: COC(=O)c1ccc2nc(-c3ccc(OC(F)(F)F)cc3)[nH]c2c1]

The title compound was prepared from 4-trifluoromethoxybenzaldehyde (0.75 mL, 1 eq., 5.3 mmol), in presence of 40% NaHSO₃ (5.4 mL), methyl 3,4-diaminobenzoate (881 mg, 1 eq., 5.3 mmol) and ethanol (3 mL) following the general procedure 4. Compound (37) (1.38 g, 78%) was obtained as a light yellow solid.

2. Synthesis of Compound (38) [2-[4-(trifluoromethoxy)phenyl]-3H-benzimidazol-5-yl]methanol

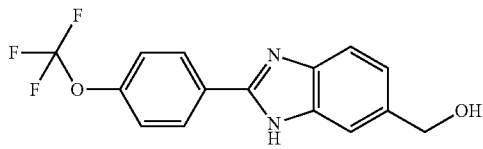

Compound (38) was prepared following general procedure 5, starting from compound (37) (1.38 g, 1 eq., 4.11 mmol), LiAlH₄ (312 mg, 2 eq., 8.22 mmol) in tetrahydrofuran (21 mL).

The product was isolated under the form of a white solid (1.21 g, 95%).

3. Synthesis of Compound (E64)

The title compound (E64) was obtained following the general procedure 12 from benzimidazole (38) (37 mg, 1 eq., 0.12 mmol), SOCl₂ (246 µL, 29 eq., 3.34 mmol), compound (36) (50 mg, 1 eq., 0.12 mmol), and diisopropylethylamine (104 µL, 5.3 eq., 0.64 mmol) in AcN (3 mL). After purification by silica gel column chromatography, eluting dichloromethane/methanol 95:5 of the resulting solution, the title compound (E64) was obtained as an amorphous creamy solid (19 mg, 31%).

Characterization:

$^1$H NMR: (400 MHz, MeOD) δ 8.20 (d, J=8.8 Hz, 2H, H$^{Ar}$), 7.63 (s, 2H, H$^{Ar}$), 7.39 (m, 7H, H$^{Ar}$), 7.03 (m, 2H, H$^{Ar}$), 6.92 (m, 2H, H$^{Ar}$), 5.07 (s, 2H, CH₂—O), 4.44 (s, 1H, H⁴ pip), 3.99 (dqd, J=7.8, 6.8, 3.0 Hz, 4H, CH₂—O—P), 3.83 (s, 2H, CH₂—N), 3.25 (d, J=21.6 Hz, 2H, CH₂—P), 2.98 (bs, 2H, H², H⁶ pip), 2.60 (bs, 2H, H², H⁶ pip), 2.06-1.84 (m, 4H, H³, H⁵ pip), 1.22 (t, J=6.8 Hz, 6H, CH₃).

$^{13}$C NMR: (101 MHz, MeOD) δ 151.43 (C$^{quat}$), 151.25 (C$^{quat}$), 150.14 (C$^{quat}$), 147.14 (C$^{quat}$) 137.91 (d, J=3.3 Hz, C$^{quat}$) 131.60 (d, J=9.1 Hz, C$^{quat}$) 129.10 (d, J=6.4 Hz, C$^{Ar}$) 128.72 (d, J=6.5 Hz, C$^{Ar}$), 128.60 (C$^{Ar}$), 128.32 (C$^{Ar}$), 128.30 (d, J=2.7 Hz, C$^{Ar}$), 125.90 (d, J=3.7 Hz, C$^{Ar}$), 122.31 (C$^{Ar}$), 121.45 (C$^{Ar}$), 121.20 (C$^{Ar}$), 118.46 (C$^{Ar}$), 115.24 (C$^{Ar}$), 70.55 (CH₂—O), 62.35 (d, J=6.9 Hz, CH₂—O—P), 62.32 (CH₂—N), 49.34 (C², C⁶ pip), 32.32 (d, J=137.2 Hz, CH₂—P), 29.57 (C³, C⁵ pip), 15.25 (d, J=6.1 Hz, CH₃).

$^{31}$P NMR: (162 MHz, MeOD) δ 27.36.

$^{19}$F NMR: (376 MHz, MeOD) δ −57.38.

HRMS-ESI (m/z) [M+H]⁺ calculated for C₃₉H₄₂F₃N₃O₆P 724.2760, found 724.2755.

Example 65: Synthesis of (E65) 6-[[4-[2-[[3-(diethoxyphosphorylmethyl)phenyl]-methoxy]phenoxy]-1-piperidyl]methyl]-2-[3-(trifluoromethoxy)phenyl]-1H-benzimidazole

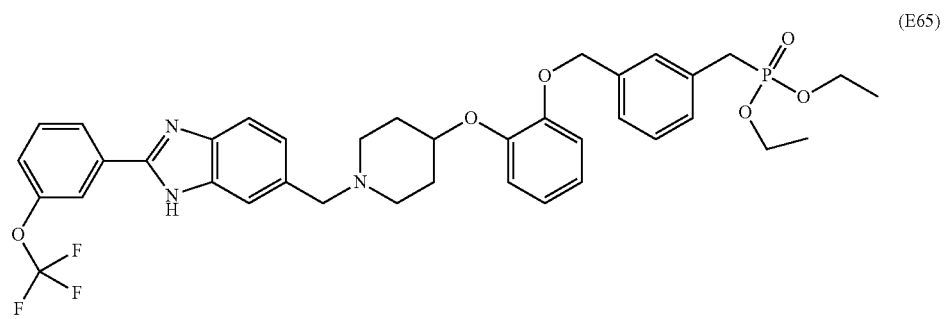 [SMILES: CCOP(=O)(Cc1cccc(COc2ccccc2OC2CCN(Cc3ccc4nc(-c5cccc(OC(F)(F)F)c5)[nH]c4c3)CC2)c1)OCC]

Procedure:

1. Synthesis of Compound (39) methyl 2-[3-(trifluoromethoxy)phenyl]-3H-benzimidazole-5-carboxylate

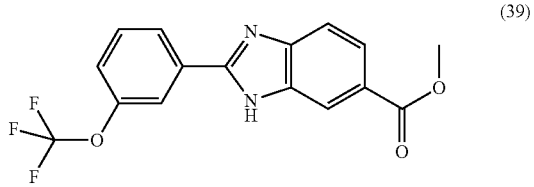 [SMILES: COC(=O)c1ccc2nc(-c3cccc(OC(F)(F)F)c3)[nH]c2c1]
(39)

The title compound was prepared from 3-trifluoromethoxybenzaldehyde (0.75 mL, 1 eq., 5.3 mmol), in presence of 40% NaHSO$_3$ (5.4 mL), methyl 3,4-diaminobenzoate (881 mg, 1 eq., 5.3 mmol) and ethanol (3 mL) following the general procedure 4. Compound (37) (1.61 g, 91%) was obtained as a white solid.

2. Synthesis of Compound (40) [2-[3-(trifluoromethoxy)phenyl]-3H-benzimidazol-5-yl]methanol

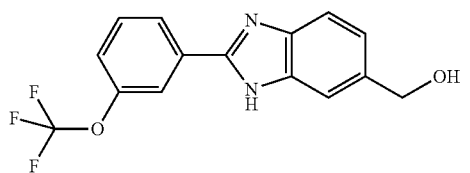
(40)

Compound (40) was prepared following general procedure 5, starting from compound (39) (1.61 g, 1 eq., 4.80 mmol), LiAlH$_4$ (364 mg, 2 eq., 9.59 mmol) in THF (24 mL). The title compound was obtained under the form of a white solid (1.41 g, 95%).

3. Synthesis of Compound (E65)

The title compound (E65) was obtained following the general procedure 12 from compound (40) (27 mg, 1 eq., 0.088 mmol), SOCl$_2$ (186 µL, 29 eq., 2.56 mmol), compound (36) (38 mg, 1 eq., 0.088 mmol), and diisopropylethylamine (79 µL, 5.3 eq., 0.47 mmol) in acetonitrile (2 mL). After purification by silica gel column chromatography, eluting dichloromethane/methanol 95:5 of the resulting solution, the title compound (E65) was obtained as an amorphous creamy solid (22 mg, 35%).

Characterization:

$^1$H NMR: (400 MHz, MeOD) δ 8.06 (ddd, J=7.90, 1.6, 1.0 Hz, 1H, H$^{Ar}$), 8.01 (s, 1H, H$^{Ar}$) 7.61 (q, J=8.2 Hz, 3H, H$^{Ar}$), 7.33 (m, 6H, H$^{Ar}$), 6.98 (m, 2H, H$^{Ar}$), 6.88 (m, 2H, H$^{Ar}$), 5.01 (s, 2H, CH$_2$—O), 4.39 (s, 1H, H$^4$ pip), 3.94 (dqd, J=8.2, 7.0, 1.1 Hz, 4H, CH$_2$—O—P), 3.80 (s, 2H, CH$_2$—N), 3.20 (d, J=21.7 Hz, 2H, CH$_2$—P), 2.95 (s, 2H, H$^2$, H$^6$ pip), 2.57 (s, 2H, H$^2$, H$^6$ pip), 1.91 (s, 4H, H$^3$, H$^5$ pip), 1.21-1.10 (dt, J=7.0, 0.4 Hz, 6H, CH$_3$).

$^{13}$C NMR: (101 MHz, MeOD) δ 150.93 (C$^{quat}$), 150.15 (C$^{quat}$), 149.73 (C$^{quat}$), 147.09 (C$^{quat}$) 137.88 (d, J=3.2 Hz, C$^{quat}$) 131.73 (C$^{Ar}$), 131.61 (d, J=9.3 Hz, C$^{quat}$) 130.71 (C$^{Quat}$) 129.10 (d, J=6.5 Hz, C$^{Ar}$), 128.72 (d, J=6.7 Hz, C$^{Ar}$), 128.31 (d, J=3.2 Hz, C$^{Ar}$), 125.90 (d, J=3.6 Hz, C$^{Ar}$), 125.01 (C$^{Ar}$) 122.34 (C$^{Ar}$) 121.44 (C$^{Ar}$) 118.93 (C$^{Ar}$) 118.48 (C$^{Ar}$) 115.20 (C$^{Ar}$) 73.12 (C$^4$ pip), 70.53 (CH$_2$—O), 62.34 (d, J=6.9 Hz, CH$_2$—O—P), 62.17 (CH$_2$—N), 49.24 (C$^2$, C$^6$ pip), 32.33 (d, J=137.5 Hz, CH$_2$—P), 29.45 (C3, C$^5$ pip), 15.25 (d, J=6.0 Hz, CH$_3$).

$^{31}$P NMR: (162 MHz, MeOD) δ 27.36

$^{19}$F NMR: (376 MHz, MeOD) δ −59.38

HRMS-ESI (m/z) [M+H]$^+$ calculated for C$_{39}$H$_{42}$F$_3$N$_3$O$_6$P 724.2760, found 724.2757.

Example 66: Synthesis of (E66) 6-[[4-[[2-[[3-(diethoxyphosphorylmethyl)phenyl]-methoxy]phenyl]methyl]-1-piperidyl]methyl]-2-phenyl-1H-benzimidazole

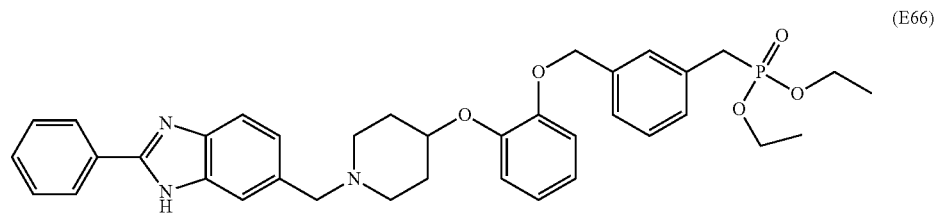 [SMILES: CCOP(=O)(Cc1cccc(COc2ccccc2OC2CCN(Cc3ccc4nc(-c5ccccc5)[nH]c4c3)CC2)c1)OCC]
(E66)

Procedure:

1. Synthesis of Compound (41): 2-benzyloxybromobenzene

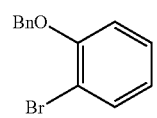
(41)

To a solution of 2-bromophenol (1.34 mL, 1 eq., 11.6 mmol) in dimethylformamide (20 mL), benzyl chloride (1.46 mL, 1.1 eq., 12.7 mmol) and potassium carbonate (3.19 g, 2 eq., 23.1 mmol) were added. The resulting mixture was stirred for 12 h at 70° C. After evaporation of all volatiles, the residue was dissolved in a mixture of ethyl acetate (80 mL) and water (40 mL). The aqueous phase was extracted three times with ethyl acetate (3×80 mL), the organic phase was washed three times with water (3×40 mL), three times with brine (3×40 mL), dried over magnesium sulfate and concentrated under reduced pressure. After a filtration on silica gel, eluting petroleum ether/ethyl acetate 8:2 of the resulting mixture, the compound (41) was obtained as a colorless oil (3.1 g, quantitative yield).

2. Synthesis of Compound (42) tert-butyl 4-[(2-benzyloxyphenyl)-hydroxymethyl]piperidine-1-carboxylate

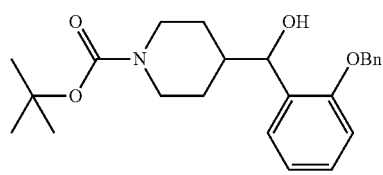

(42)

Under argon atmosphere, compound (41) (3.36 g, 1.1 eq., 12.7 mmol) was dissolved in tetrahydrofuran (THF) (19 mL) and cooled down at −78° C. After 10 minutes stirring, n-BuLi (2.5 M in hexane, 5.03 mL, 1.1 eq. 12.7 mmol) was added dropwise to the solution and stirred for 30 min. at −78° C. A solution of 1-(tert-Butoxycarbonyl)-4-piperidinecarboxaldehyde (2.47 g, 1 eq., 11.6 mmol) in THE (19 mL) was then introduced by cannulation slowly into the flask. After 10 min at −78° C., the solution was then allowed to stir at room temperature for 3 hours and quenched with a slow addition of water (20 mL). The aqueous phase was subsequently extracted three times with ethyl acetate (3×80 mL), dried over MgSO₄ and reduced in vacuo. The resulting product was then loaded onto a silica gel column and purified eluting Petroleum ether/Ethyl Acetate 8:2.

Compound (42) was obtained as colorless crystals (2.94 g, 65%).

3. Synthesis of Compound (43) tert-butyl 4-[(2-hydroxyphenyl)methyl]piperidine-1-carboxylate

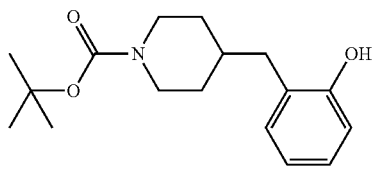

(43)

In an autoclave, compound (42) (1 g, 1 eq., 2.55 mmol) was dissolved in ethyl acetate (43 mL). The solution and the atmosphere in the apparatus were degassed with argon before the introduction of 10% Pd/C (500 mg). The solution and the atmosphere were again saturated with argon, then the autoclave was sealed and filled with H₂ until a pressure of 7 bars. The reaction was stirred for 24 h at room temperature, filtrated onto Celite®, and the filtrate was evaporated, giving the title compound (43) as colorless crystals (587 mg, 79%).

4. Synthesis of Compound (44) tert-butyl 4-[[2-[[3-(diethoxyphosphorylmethyl)-phenyl]methoxy]phenyl]methyl]piperidine-1-carboxylate

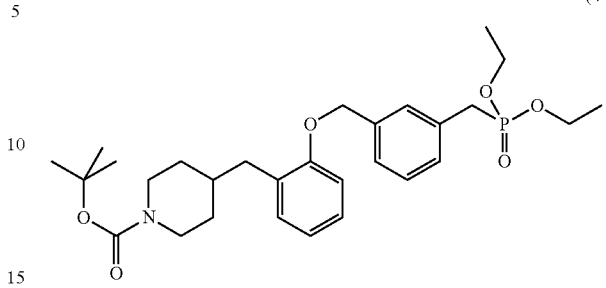

(44)

In a 2-5 mL microwave vial, compound (32) (331 mg, 1.5 eq., 1.03 mmol) was dissolved in dimethylacetamide (5 mL). To this mixture were sequentially added potassium carbonate (190 mg, 2 eq., 1.37 mol), compound (43) (200 mg, 1 eq., 0.69 mmol) and a catalytic amount of sodium iodide (few crystals). The reaction mixture was stirred for 30 min at 140° C. under microwave irradiation, and the obtained solution was dissolved in water (10 mL) and ethyl acetate (50 mL). The aqueous phase was then extracted three times with ethyl acetate (3×30 mL), and the organic phase washed five times with water (5×10 mL), once with brine (10 mL), dried over MgSO₄ and evaporated. The residue was consequently purified by column chromatography (DCM/MeOH 99:1) to afford the title compound (44) compound as a colorless oil (330 mg, 91%).

5. Synthesis of Compound (45) 4-[[2-[[3-(diethoxyphosphorylmethyl)-phenyl]methoxy]phenyl]methyl]piperidine

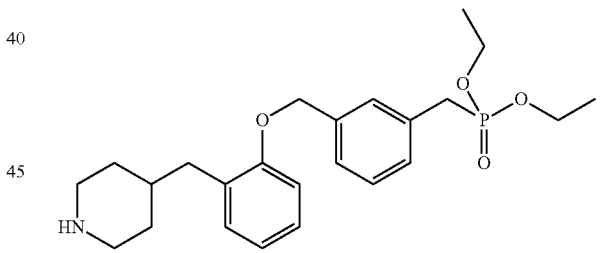

(45)

Following the general procedure 11, trifluoroacetic acid (4.5 mL, 100 eq., 58.3 mmol) was added to a solution of compound (44) (310 mg, 1 eq., 0.58 mmol) in dichloromethane (DCM) (9 mL). The title compound (45) was obtained after flash column chromatography (DCM/methanol 95:5), as a colorless oil (235 mg, 94%).

6. Synthesis of Compound (E66)

The title compound (E66) was obtained following the general procedure 12 from compound (3) (26 mg, 1 eq., 0.12 mmol), SOCl₂ (246 µL, 29 eq., 3.37 mmol), compound (45) (50 mg, 1 eq., 0.12 mmol), and diisopropylethylamine (105 µL, 5.3 eq., 0.61 mmol) in acetonitrile (3 mL). After purification by silica gel column chromatography, eluting dichloromethane/methanol 95:5, the title compound (E66) was obtained as an amorphous creamy solid (20 mg, 24%).

Characterization:

¹H NMR: (400 MHz, MeOD) δ 8.10 (dd, J=8.1, 2.7 Hz, 2H, $H^{Ar}$), 7.67 (s, 1H, $H^{Ar}$), 7.62 (d, J=8.6 Hz, 1H, $H^{Ar}$), 7.54

(m, 3H, H$^{Ar}$), 7.42 (s, 1H, H$^{Ar}$), 7.32 (m, 3H, H$^{Ar}$), 7.24 (m, 1H, H$^{Ar}$), 7.15 (dt, J=8.1, 1.6 Hz, 1H), 7.10 (dd, J=7.4, 1.6 Hz, 1H, H$^{Ar}$), 6.98 (d, J=7.8 Hz, 1H, H$^{Ar}$), 6.86 (td, J=7.4, 0.8 Hz, 1H, H$^{Ar}$), 5.07 (s, 2H, CH$_2$—O), 3.96 (m, 6H, CH$_2$—O—P, CH$_2$—N), 3.24 (d, J=21.6 Hz, 2H, CH$_2$—P), 3.18 (bd, J=11.6 Hz, 2H, H$^2$, H$^6$ pip), 2.64 (d, J=6.7 Hz, 2H, CH$_2$), 2.47 (s, 2H, H$^2$, H$^6$ pip), 1.80 (m, 1H, H$^4$ pip), 1.74 (bd, J=14.9 Hz, 2H, H$^3$, H$^5$ pip), 1.45 (bq, J=14.4 Hz, 2H, H$^3$, H$^5$ pip), 1.20 (t, J=7.1 Hz, 6H, CH$_3$).

$^{13}$C NMR: (101 MHz, MeOD) δ 156.59 (C$^{quat}$—CH$_2$), 153.14 (C$^{quat}$), 149.72 (d, J=2.0 Hz, C$^{quat}$), 138.00 (d, J=3.4 Hz, C$^{quat}$) 131.64 (d, J=9.2 Hz, C$^{quat}$) 130.59 (C$^{Ar}$), 130.25 (C$^{Ar}$) 129.37 (C$^{Ar}$), 129.04 (d, J=6.7 Hz, C$^{Ar}$) 128.82 (C$^{Ar}$), 128.43 (d, J=6.5 Hz, C$^{Ar}$) 128.34 (d, J=3.2 Hz, C$^{Ar}$) 128.29 (C$^{Ar}$) 127.17 (C$^{Ar}$), 126.50 (C$^{Ar}$), 125.72 (C$^{Ar}$), 125.62 (d, J=3.6 Hz, C$^{Ar}$) 120.31 (C$^{Ar}$) 111.65 (C$^{Ar}$), 69.23 (CH$_2$—O), 62.38 (d, J=6.9 Hz, CH$_2$—O—P), 61.80 (CH$_2$—N), 52.70 (C$^2$, C$^6$ pip), 36.13 (CH$_2$), 35.38 (C4 pip), 32.30 (d, J=137.8 Hz, CH$_2$—P), 30.07 (C3, C$^5$ pip), 15.26 (d, J=6.0 Hz, CH$_3$).

$^{31}$P NMR: (162 MHz, MeOD) δ 27.27.

HRMS-ESI (m/z) [M+H]$^+$ calcd for C$_{39}$H$_{47}$N$_3$O$_3$P 638.3146, found 638.3141.

Example 67: Synthesis of (E67) 6-[[4-[[2-[[3-(diethoxyphosphorylmethyl)phenyl]-methoxy]phenyl]methyl]-1-piperidyl]methyl]-2-[4-(trifluoromethyl)phenyl]-1H-benzimidazole

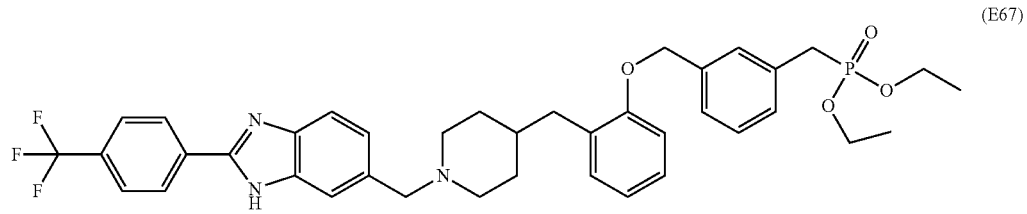 [SMILES: CCOP(=O)(Cc1cccc(COc2ccccc2CC2CCN(Cc3ccc4nc(-c5ccc(C(F)(F)F)cc5)[nH]c4c3)CC2)c1)OCC]

(E67)

Procedure:
The title compound (E67) was obtained following the general procedure 12 from compound (12) (60 mg, 1 eq., 0.20 mmol), SOCl$_2$ (452 μL, 29 eq., 6.20 mmol), compound (45) (80 mg, 1 eq., 0.20 mmol), and diisopropylethylamine (168 μL, 5.3 eq., 0.99 mmol) in acetonitrile (4 mL). After purification by silica gel column chromatography, eluting dichloromethane/methanol 95:5, the title compound (E67) was obtained as an amorphous creamy solid (24 mg, 19%).

Characterization:
$^1$H NMR: (400 MHz, MeOD) δ 8.46 (s, 1H, H$^{Ar}$), 8.37 (d, J=7.6 Hz, 1H, H$^{Ar}$), 7.75 (m, 4H, H$^{Ar}$), 7.33 (m, 5H, H$^{Ar}$), 7.14 (dd, J=7.8, 1.8 Hz, 2H), 7.01 (dd, J=8.3, 1.1 Hz, 1H, H$^{Ar}$) 6.88 (td, J=7.4, 1.2 Hz, 1H, H$^{Ar}$), 5.08 (s, 2H, CH$_2$—O), 4.26 (s, 2H, CH$_2$—N), 3.99 (dqd, J=9.5, 7.1, 1.5 Hz, 4H, CH$_2$—O—P), 3.38 (under MeOD peak, m, 2H, H$^2$, H$^6$ pip), 3.22 (under MeOD peak, m, 2H, CH$_2$—P), 2.81 (t, J=12.0 Hz, 2H, H$^2$, H$^6$ pip), 2.68 (d, J=6.8 Hz, 2H, CH$_2$), 1.90 (m, 1H, H$^4$ pip), 1.82 (bd, J=13.5 Hz, 2H, H$^3$, H$^5$ pip), 1.55 (bt, J=12.0 Hz, 2H, H$^3$, H$^5$ pip), 1.21 (td, J=7.1, 0.6 Hz, 6H, CH$_3$).

$^{13}$C NMR: (101 MHz, MeOD) δ 156.60 (C$^{quat}$—CH$_2$), 151.84 (C$^{quat}$), 137.93 (d, J=3.3 Hz, C$^{quat}$) 131.69 (d, J=9.3 Hz, C$^{quat}$) 131.56 (C$^{quat}$), 130.57 (C$^{Ar}$) 130.36 (C$^{Ar}$) 129.94 (C$^{Ar}$) 129.90 (C$^{quat}$), 129.10 (d, J=6.6 Hz, C$^{Ar}$), 128.45 (d, J=6.5 Hz, C$^{Ar}$) 128.34 (d, J=3.4 Hz, C$^{Ar}$) 127.88 (C$^{Ar}$), 127.35 (C$^{Ar}$), 125.68 (d, J=3.9 Hz, C$^{Ar}$), 123.25 (C$^{Ar}$) 123.18 (C$^{Ar}$) 120.40 (C$^{Ar}$) 111.68 (C$^{Ar}$), 69.24 (CH$_2$—O), 62.41 (d, J=6.9 Hz, CH$_2$—O—P), 60.93 (CH$_2$—N), 52.34 (C$^2$, C$^6$ pip), 35.70 (CH$_2$), 34.86 (C4 pip), 32.16 (d, J=138.0 Hz, CH$_2$—P), 29.22 (C3, C$^5$ pip), 15.24 (d, J=6.0 Hz, CH$_3$).

$^{31}$P NMR: (162 MHz, MeOD) δ 27.22.

$^{19}$F NMR: (376 MHz, MeOD) δ −64.36.

HRMS-ESI (m/z) [M+H]$^+$ calculated for C$_{39}$H$_{44}$F$_3$N$_3$O$_4$P 706.3022, found 706.3013.

Example 68: Synthesis of (E68) 6-[[4-[[2-[[3-(diethoxyphosphorylmethyl)phenyl]-methoxy]phenyl]methyl]-1-piperidyl]methyl]-2-[3-(trifluoromethyl)phenyl]-1H-benzimidazole

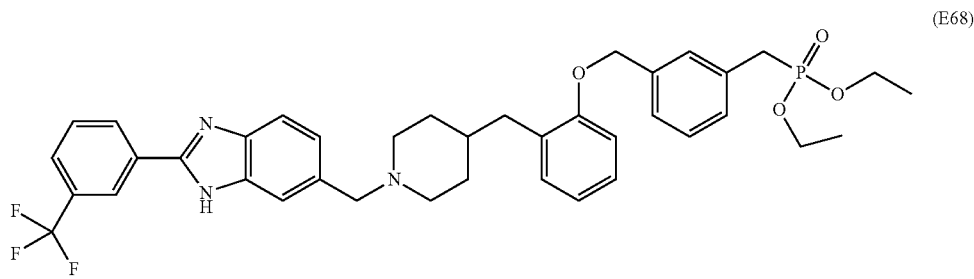 [SMILES: CCOP(=O)(Cc1cccc(COc2ccccc2CC2CCN(Cc3ccc4nc(-c5cccc(C(F)(F)F)c5)[nH]c4c3)CC2)c1)OCC]

(E68)

Procedure:

The title compound (E68) was obtained following the general procedure 12 from compound (14) (60 mg, 1 eq., 0.20 mmol), SOCl$_2$ (452 µL, 29 eq., 6.20 mmol,) compound (45) (80 mg, 1 eq., 0.20 mmol) and diisopropylethylamine (168 µL, 5.3 eq., 0.99 mmol) in acetonitrile (4 mL). After purification by silica gel column chromatography, eluting dichloromethane/methanol 95:5, the clean compound (E68) was obtained as an amorphous creamy solid (26 mg, 20%).

Characterization:

$^1$H NMR: (400 MHz, MeOD) δ 8.46 (s, 1H, H$^{4r}$), 8.37 (d, J=7.8 Hz, 1H, H$^{4r}$), 7.85 (d, J=7.8 Hz, 1H, H$^{4r}$), 7.79 (t, J=7.8 Hz, 1H, H$^{4r}$), 7.68 (m, 2H, H$^{4r}$), 7.44 (s, 1H, H$^{4r}$), 7.35 (m, 3H, H$^{4r}$), 7.27 (m, 1H, H$^{4r}$), 7.16 (dt, J=8.3, 1.8 Hz, 1H, H$^{4r}$), 7.11 (dd, J=7.4, 1.5 Hz, 1H, H$^{4r}$), 6.99 (d, J=7.8 Hz, 1H, H$^{4r}$), 6.87 (td, J=7.5, 1.0 Hz, 1H, H$^{4r}$), 5.09 (s, 2H, CH$_2$—O), 3.97 (m, 6H, CH$_2$—O—P, CH$_2$—N), 3.26 (d, J=21.7 Hz, 2H, CH$_2$—P), 3.13 (bd, J=11.3 Hz, 2H, H$^2$, H$^6$ pip), 2.65 (d, J=6.8 Hz, 2H, CH$_2$), 2.38 (bs, 2H, H$^2$, H$^6$ pip), 1.78 (m, 1H, H$^4$ pip), 1.73 (bd, J=13.4 Hz, 2H, H$^3$, H$^5$ pip), 1.44 (bq, J=13.4 Hz, 2H, H$^3$, H$^5$ pip), 1.22 (t, J=7.1 Hz, 6H, CH$_3$).

$^{13}$C NMR: (101 MHz, MeOD) δ 156.59 (C$^{quat}$—CH$_2$), 151.20 (C$^{quat}$), 138.03 (d, J=3.4 Hz, C$^{quat}$) 131.63 (d, J=9.1 Hz, C$^{quat}$) 131.42 (C$^{quat}$) 131.10 (C$^{quat}$) 130.59 (C$^{Ar}$), 130.55 (C$^{Ar}$) 129.87 (C$^{Ar}$) 129.83 (C$^{Ar}$), 129.02 (d, J=6.4 Hz, C$^{Ar}$) 128.46 (C$^{Ar}$) 128.37 (d, J=4.4 Hz, C$^{Ar}$), 128.33 (d, J=3.2 Hz, C$^{Ar}$) 127.09 (C$^{Ar}$) 126.50 (C$^{Ar}$), 125.60 (d, J=3.8 Hz, C$^{Ar}$), 125.34 (C$^{Ar}$), 123.12 (d, J=4.1 Hz, C$^{Ar}$) 122.64 (C$^{Ar}$) 120.26 (C$^{Ar}$) 111.64 (C$^{Ar}$) 69.22 (CH$_2$—O), 62.36 (d, J=7.0 Hz, CH$_2$—O—P), 62.12 (CH$_2$—N), 52.87 (C$^2$, C$^6$ pip), 36.33 (CH$_2$), 35.64 (C4 pip), 32.30 (d, J=137.2 Hz, CH$_2$—P), 30.46 (C3, C$^5$ pip), 15.25 (d, J=5.9 Hz, CH$_3$).

$^{31}$P NMR: (162 MHz, MeOD) δ 27.29.

$^{19}$F NMR: (376 MHz, MeOD) δ −64.34.

HRMS-ESI (m/z) [M+H]$^+$ calculated for C$_{39}$H$_{44}$F$_3$N$_3$O$_4$P 706.3022, found 706.3013.

Example 69: Synthesis of (E69) 6-[[4-[[2-[[3-(diethoxyphosphorylmethyl)phenyl]-methoxy]phenyl]methyl]-1-piperidyl]methyl]-2-[4-(trifluoromethoxy)phenyl]-1H-benzimidazole Procedure:

The title compound (E69) was obtained following the general procedure 14 from compound (38) (60 mg, 1 eq., 0.20 mmol), SOCl$_2$ (452 µL, 29 eq., 6.20 mmol), compound (45) (80 mg, 1 eq., 0.20 mmol), and diisopropylethylamine (168 µL, 5.3 eq., 0.99 mmol) in acetonitrile (4 mL). After purification by silica gel column chromatography, eluting dichloromethane/methanol 95:5 of the resulting mixture, the title compound (E69) was obtained as an amorphous creamy solid (31 mg, 24%).

Characterization:

$^1$H NMR: (400 MHz, MeOD) δ 8.21 (d, J=8.9 Hz, 2H, H$^{4r}$), 7.67 (m, 2H, H$^{4r}$), 7.49 (d, J=9.0 Hz, 2H, H$^{4r}$), 7.44 (s, 1H, H$^{4r}$), 7.31 (m, 4H, H$^{4r}$), 7.16 (dt, J=8.3, 1.5 Hz, 1H), 7.12 (dd, J=7.6, 1.6 Hz, 1H, H$^{4r}$), 7.00 (d, J=8.3 Hz, 1H, H$^{4r}$), 6.88 (td, J=7.5, 1.0 Hz, 1H, H$^{4r}$), 5.10 (s, 2H, CH$_2$—O), 4.00 (m, 6H, CH$_2$—O—P, CH$_2$—N), 3.27 (d, J=21.8 Hz, 2H, CH$_2$—P), 3.18 (bd, J=11.8 Hz, 2H, H$^2$, H$^6$ pip), 2.67 (d, J=6.8 Hz, 2H, CH$_2$), 2.47 (bs, 2H, H$^2$, H$^6$ pip), 1.81 (m, 1H, H$^4$ pip), 1.75 (bd, J=15.4 Hz, 2H, H$^3$, H$^5$ pip), 1.46 (bq, J=10.4 Hz, 2H, H$^3$, H$^5$ pip), 1.22 (t, J=7.1 Hz, 6H, CH$_3$).

$^{13}$C NMR: (101 MHz, MeOD) δ 156.60 (C$^{quat}$—CH$_2$), 151.64 (C$^{quat}$), 150.52 (C$^{quat}$), 138.00 (d, J=3.3 Hz, C$^{quat}$) 131.64 (d, J=9.2 Hz, C$^{quat}$) 130.59 (C$^{Ar}$), 129.03 (d, J=6.9 Hz, C$^{Ar}$) 128.50 (C$^{Ar}$), 128.43 (d, J=6.6 Hz, C$^{Ar}$) 128.38 (C$^{Ar}$), 128.33 (d, J=3.1 Hz, C$^{Ar}$), 127.15 (C$^{Ar}$), 125.62 (d, J=3.7 Hz, C$^{Ar}$), 125.34 (C$^{Ar}$), 123.12 (d, J=4.1 Hz, C$^{Ar}$) 121.74 (C$^{Ar}$) 121.25 (C$^{Ar}$) 120.29 (C$^{Ar}$) 119.20 (C$^{Ar}$), 111.65 (C$^{Ar}$), 69.23 (CH$_2$—O), 62.38 (d, J=6.9 Hz, CH$_2$—O—P), 61.90 (CH$_2$—N), 52.87 (C$^2$, C$^6$ pip), 36.20 (CH$_2$), 35.45 (C4 pip), 32.26 (d, J=137.8 Hz, CH$_2$—P), 30.19 (C3, C$^5$ pip), 15.25 (d, J=6.0 Hz, CH$_3$)

$^{31}$P NMR: (162 MHz, MeOD) δ 27.27

$^{19}$F NMR: (376 MHz, MeOD) δ −59.39

HRMS-ESI (m/z) [M+H]$^+$ calculated for C$_{39}$H$_{44}$F$_3$N$_3$O$_5$P 722.2971, found 722.2965.

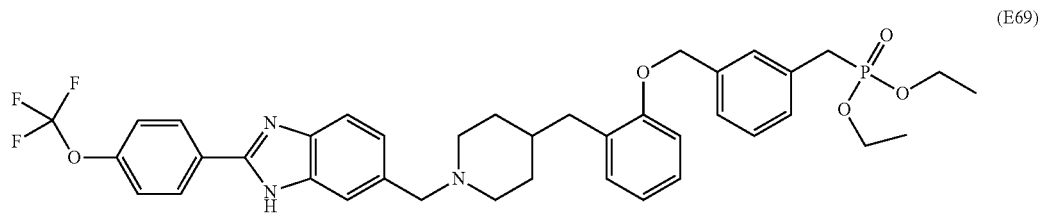 [SMILES: CCOP(=O)(Cc1cccc(COc2ccccc2CC2CCN(Cc3ccc4nc(-c5ccc(OC(F)(F)F)cc5)[nH]c4c3)CC2)c1)OCC]

(E69)

Example 70: Synthesis of (E70) 6-[[4-[[2-[[3-(diethoxyphosphorylmethyl)phenyl]-methoxy]phenyl]methyl]-1-piperidyl]methyl]-2-[3-(trifluoromethoxy)phenyl]-3a,7a-dihydro-1H-benzimidazole

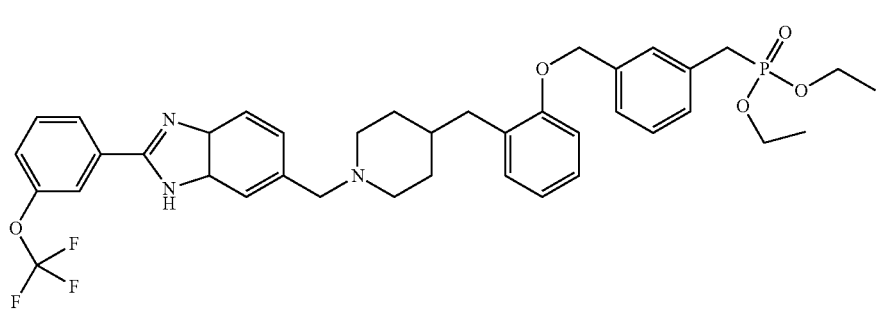

(E70)

Procedure:

The title compound (E70) was obtained following the general procedure 12 from benzimidazole (40) (60 mg, 1 eq., 0.20 mmol), SOCl$_2$ (452 μL, 29 eq., 6.20 mmol) compound (45) (80 mg, 1 eq., 0.20 mmol) and then diisopropylethylamine (168 μL, 5.3 eq., 0.99 mmol) in acetonitrile (4 mL). After purification by silica gel column chromatography, eluting DCM/MeOH 95:5 of the resulting mixture, the title compound (E70) was obtained as an amorphous creamy solid (26 mg, 20%).

Characterization:

$^1$H NMR: (400 MHz, MeOD) δ 8.10 (ddd, J=7.8, 1.3, 0.6 Hz, 1H, H$^{Ar}$), 8.05 (s, 1H, H$^{Ar}$) 7.66 (m, 3H, H$^{Ar}$), 7.45 (m, 2H, H$^{Ar}$), 7.28 (m, 4H, H$^{Ar}$), 7.14 (dt, J=7.4, 1.7 Hz, 1H), 7.10 (dd, J=7.7, 1.7 Hz, 1H, H$^{Ar}$), 6.98 (d, J=8.0 Hz, 1H, H$^{Ar}$), 6.86 (td, J=7.4, 1.0 Hz, 1H, H$^{Ar}$), 5.07 (s, 2H, CH$_2$—O), 3.98 (m, 6H, CH$_2$—O—P, CH$_2$—N), 3.25 (d, J=21.7 Hz, 2H, CH$_2$—P), 3.17 (bd, J=10.2 Hz, 2H, H$^2$, H$^6$ pip), 2.64 (d, J=6.7 Hz, 2H, CH$_2$), 2.47 (bt, J=11.8 Hz, 2H, H$^2$, H$^6$ pip), 1.81 (m, 1H, H$^4$ pip), 1.74 (bd, J=13.0 Hz, 2H, H$^3$, H$^5$ pip), 1.45 (bq, J=13.3 Hz, 2H, H$^3$, H$^5$ pip), 1.20 (t, J=6.8 Hz, 6H, CH$_3$).

$^{13}$C NMR: (101 MHz, MeOD) δ 156.58 (C$^{quat}$—CH$_2$), 151.29 (C$^{quat}$), 149.72 (d, J=2.0 Hz, C$^{quat}$), 137.99 (d, J=3.3 Hz, C$^{quat}$) 131.63 (C$^{quat}$), 131.61 (d, J=9.9 Hz, C$^{quat}$) 130.75 (C$^{Ar}$), 130.58 (C$^{Ar}$), 129.02 (d, J=7.1 Hz, C$^{Ar}$), 128.41 (d, J=6.9 Hz, C$^{Ar}$) 128.36 (C$^{Ar}$) 128.34 (d, J=3.7 Hz, C$^{Ar}$), 127.15 (C$^{Ar}$), 125.61 (d, J=3.7 Hz, C$^{Ar}$), 125.43 (C$^{Ar}$), 125.01 (C$^{Ar}$), 122.57 (C$^{Ar}$), 122.46 (C$^{Ar}$), 120.30 (C$^{Ar}$), 120.29 (Ar), 118.97 (Ar), 118.50 (C$^{Ar}$), 111.64 (C$^{Ar}$), 69.22 (CH$_2$—O), 62.36 (d, J=6.9 Hz, CH$_2$—O—P), 61.80 (CH$_2$—N), 52.70 (C$^2$, C$^6$ pip), 36.14 (CH$_2$), 35.41 (C4 pip), 32.23 (d, J=137.7 Hz, CH$_2$—P), 30.12 (C3, C$^5$ pip), 15.25 (d, J=6.0 Hz, CH$_3$)

$^{31}$P NMR: (162 MHz, MeOD) δ 27.27

$^{19}$F NMR: (376 MHz, MeOD) δ −59.39

HRMS-ESI (m/z) [M+H]$^+$ calculated for C$_{39}$H$_{44}$F$_3$N$_3$O$_5$P 722.2971, found 722.2964.

Example 71: Synthesis of (E71) 6-[[4-[2-[[4-(diethoxyphosphorylmethyl)phenyl]-methoxy]phenoxy]-1-piperidyl]methyl]-2-phenyl-1H-benzimidazole

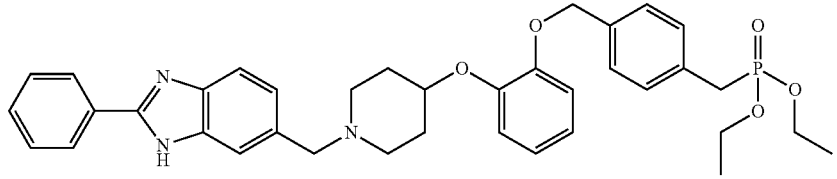

(E71)

Procedure:

1. Synthesis of Compound (46) 2-[2-[[4-(dimethoxyphosphorylmethyl)-phenyl]methoxy]phenoxy]tetrahydropyran

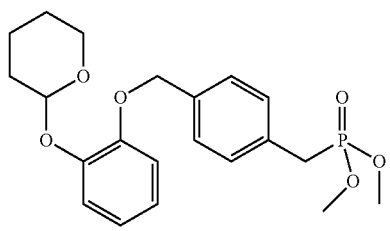

(46)

Compound (30) (1.12 g, 1 eq., 5.74 mmol) was dissolved in dimethylformamide (18 mL) in a 10-20 mL microwave vial. To this solution was added potassium carbonate (1.58 g, 2 eq., 11.48 mmol), compound (26) (2.03 g, 1.1 eq., 6.32 mmol) and few crystals of sodium iodide (catalytic amount). The solution was then stirred for 20 min at 80° C. under microwave irradiation. After evaporation of all volatiles, the residue was purified by silica gel chromatography to afford the title compound (46) as a colorless oil (1.42 g, 57%).

2. Synthesis of Compound (47) 2-[[4-(dimethoxyphosphorylmethyl)-phenyl]methoxy]phenol

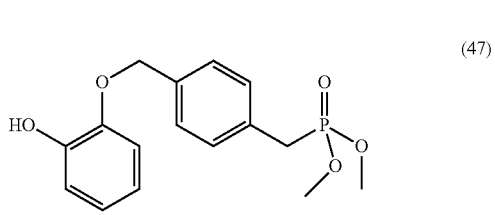 [SMILES: COP(=O)(Cc1ccc(COc2ccccc2O)cc1)OC]

(47)

To a solution of compound (46) (1.16 g, 1 eq., 2.67 mmol) in ethanol (27 mL) was added pyridium p-toluenesulfonate (34 mg, 5 mol %, 0.13 mmol). The solution was then stirred at 55° C. during 3 hours, followed by the evaporation of all volatiles. The residue was then purified by flash chromatography, eluting Petroleum Ether/EtOAc 65:35 to 1:1, to give compound (47) as a white solid (936 mg, quantitative yield).

3. Synthesis of Compound (48) tert-butyl 4-[2-[(4-diethoxyphosphorylphenyl)-methoxy]phenoxy]piperidine-1-carboxylate

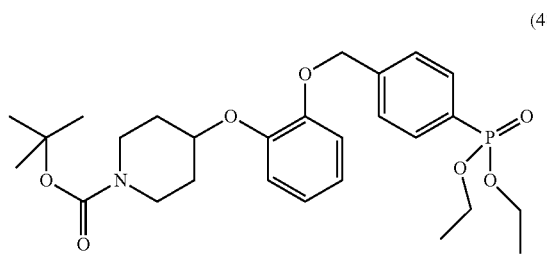

(48)

In a 10-20 mL microwave vial, compound (47) (512 mg, 1 eq., 1.46 mmol) was dissolved in dimethylacetamide (13 mL). To this mixture was then added potassium carbonate (404 mg, 2 eq., 2.92 mmol) and compound (34) (778 mg, 1.5 eq., 2.19 mmol), before being stirred at 140° C. during 30 min under microwave irradiation. The resulting residue was dissolved in ethyl acetate (20 mL) and water (25 mL), and the aqueous phase was extracted three times with ethyl acetate (3×20 mL). The organic phase was then washed 5 times with water (5×25 mL), once with brine (25 mL) and dried over magnesium sulfate. The residue was concentrated under reduced pressure and purified by silica gel column chromatography, eluting dichloromethane/methanol 99:1, to afford the compound (48) as colorless oil (483 mg, 62% of conversion).

4. Synthesis of Compound (49) 4-[2-[(4-diethoxyphosphorylphenyl)-methoxy]phenoxy]piperidine

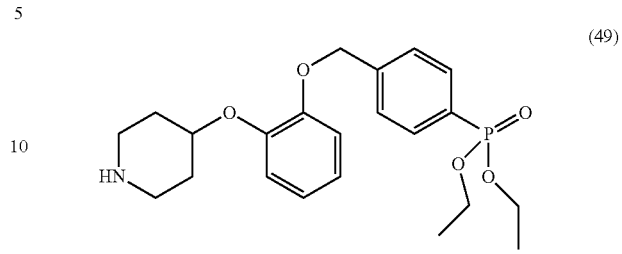

(49)

Following general procedure 11, trifluoroacetic acid (10.6 mL, 100 eq., 139 mmol) was added to a solution of compound (48) (740 mg, 1 eq., 1.39 mmol) in dichloromethane (20 mL). Pure compound (49) was obtained after flash column chromatography (dichloromethane/methanol 95:5), as an orange solid (588 mg, 67%).

5. Synthesis of Compound (E71)

The title compound (E71) was obtained following the general procedure 12 from compound (3) (31 mg, 1 eq., 0.138 mmol), SOCl$_2$ (293 µL, 29 eq., 4.01 mmol), compound (49) (60 mg, 1 eq., 0.138 mmol), and diisopropylethylamine (124 µL, 5.3 eq., 0.73 mmol) in acetonitrile (2 mL). After purification by silica gel column chromatography, eluting dichloromethane/methanol 95:5, the title compound (E71) was obtained as an amorphous creamy solid (29 mg, 40%).

Characterization:
$^1$H NMR: (400 MHz, MeOD) δ 8.12 (d, J=7.0 Hz, 2H, H$^{Ar}$), 7.63 (m, 5H, H$^{Ar}$), 7.37 (m, 5H, H$^{Ar}$), 7.04 (m, 2H, H$^{Ar}$), 6.91 (dquint, J=7.3, 1.9 Hz, 2H, H$^{Ar}$), 5.06 (s, 2H, CH$_2$—O), 4.48 (s, 1H, H$^4$ pip), 4.00 (ddq, J=8.8, 7.0, 1.8 Hz, 4H, CH$_2$—O—P), 3.93 (s, 2H, CH$_2$—N), 3.24 (d, J=21.7 Hz, 2H, CH$_2$—P), 3.06 (bs, 2H, H$^2$, H$^6$ pip), 2.76 (bs, 2H, H$^2$, H$^6$ pip), 1.97 (m, 4H, H$^3$, H$^5$ pip), 1.23 (t, J=7.0 Hz, 6H, CH$_3$).
$^{13}$C NMR: (101 MHz, MeOD) δ 150.15 (C$^{quat}$), 147.01 (C$^{quat}$), 136.24 (d, J=3.9 Hz, C$^{quat}$) 131.11 (d, J=9.2 Hz, C$^{quat}$) 130.19 (C$^{Ar}$), 129.71 (d, J=6.6 Hz, C$^{Ar}$) 129.42 (C$^{Ar}$) 128.79 (C$^{Ar}$) 127.59 (d, J=4.0 Hz, C$^{Ar}$) 126.48 (C$^{Ar}$) 122.46 (C$^{Ar}$) 121.46 (C$^{Ar}$), 118.52 (C$^{Ar}$) 115.23 (C$^{Ar}$), 70.49 (CH$_2$—O), 62.30 (d, J=6.9 Hz, CH$_2$—O—P), 62.09 (CH$_2$—N), 48.99 (C$^2$, C$^6$ pip), 32.00 (d, J=138.2 Hz, CH$_2$—P), 29.14 (C3, C$^5$ pip), 15.23 (d, J=6.0 Hz, CH$_3$).
$^{31}$P NMR: (162 MHz, MeOD) δ 27.43.
HRMS-ESI (m/z) [M+H]$^+$ calculated for C$_{37}$H$_{43}$N$_3$O$_5$P 640.2941, found 640.2935.

Example 72: Synthesis of (E72) 6-[[4-[2-[[4-(diethoxyphosphorylmethyl)phenyl]-methoxy]phenoxy]-1-piperidyl]methyl]-2-[4-(trifluoromethyl)phenyl]-3a,7a-dihydro-1H-benzimidazole

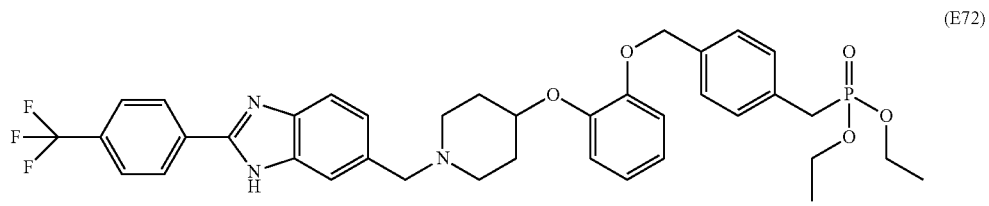

(E72)

Procedure:

The title compound (E72) was obtained following the general procedure 12 from compound (12) (34 mg, 1 eq., 0.115 mmol), SOCl$_2$ (243 µL, 29 eq., 3.35 mmol), compound (49) (50 mg, 1 eq., 0.115 mmol), and diisopropylethylamine (100 µL, 5.3 eq., 0.59 mmol) in acetonitrile (3 mL). After purification by silica gel column chromatography, eluting dichloromethane/methanol 95:5, the clean compound (E72) was obtained as an amorphous creamy solid (28 mg, 32%).

Characterization:

$^1$H NMR: (400 MHz, MeOD) δ 8.42 (bs, 1H, H$^{4r}$), 8.33 (d, J=8.0 Hz, 1H, H$^{4r}$), 7.70 (m, 5H, H$^{4r}$), 7.38 (d, J=8.0 Hz, 2H, H$^{4r}$), 7.28 (m, 3H, H$^{4r}$), 6.98 (m, 2H, H$^{4r}$), 6.88 (m, 2H, H$^{4r}$), 5.01 (s, 2H, CH$_2$—O), 4.37 (d, J=7.4 Hz, 1H, H$^4$ pip), 3.98 (m, 4H, CH$_2$—O—P), 3.75 (s, 2H, CH$_2$—N), 3.20 (d, J=21.8 Hz, 2H, CH$_2$—P), 2.89 (bs, 2H, H$^2$, H$^6$ pip), 2.51 (bs, 2H, H$^2$, H$^6$ pip), 1.89 (m, 4H, H$^3$, H$^5$ pip), 1.20 (t, J=7.1 Hz, 6H, CH$_3$).

$^{13}$C NMR: (101 MHz, MeOD) δ 150.89 (C$^{quat}$), 150.05 (C$^{quat}$), 147.19 (C$^{quat}$), 136.29 (d, J=3.0 Hz, C$^{quat}$) 131.36 (C$^{quat}$), 131.04 (C$^{quat}$) 130.94 (C$^{quat}$), 130.72 (C$^{quat}$), 130.63 (C$^{quat}$) 129.83 (C$^{Ar}$) 129.78 (C$^{Ar}$), 129.67 (d, J=6.6 Hz, C$^{Ar}$), 127.50 (d, J=3.3 Hz, C$^{Ar}$) 126.38 (C$^{Ar}$) 125.36 (C$^{Ar}$), 125.14 (C$^{Ar}$) 123.08 (C$^{Ar}$) 122.66 (C$^{Ar}$) 122.19 (C$^{Ar}$), 121.45 (C$^{Ar}$) 118.29 (C$^{Ar}$), 115.33 (C$^{Ar}$), 70.50 (CH$_2$—O), 62.48 (CH$_2$—N), 62.30 (d, J=7.0 Hz, CH$_2$—O—P), 49.37 (C$^2$, C$^6$ pip), 31.96 (d, J=138.1 Hz, CH$_2$—P), 29.70 (C3, C$^5$ pip), 15.25 (d, J=5.9 Hz, CH$_3$).

$^{31}$P NMR: (162 MHz, MeOD) δ 27.42.

$^{19}$F NMR: (376 MHz, MeOD) δ −64.25.

HRMS-ESI (m/z) [M+H]$^+$ calculated for C$_{39}$H$_{42}$F$_3$N$_3$O$_5$P 708.2811, found 708.2812.

Example 73: Synthesis of (E73) 6-[[4-[2-[[4-(diethoxyphosphorylmethyl)phenyl]-methoxy]phenoxy]-1-piperidyl]methyl]-2-[3-(trifluoromethyl)phenyl]-1H-benzimidazole Procedure:

The title compound (E73) was obtained following the general procedure 12 from compound (14) (47 mg, 1 eq., 0.16 mmol), SOCl$_2$ (340 µL, 29 eq., 4.68 mmol), compound (49) (70 mg, 1 eq., 0.16 mmol), and diisopropylethylamine (144 µL, 5.3 eq., 0.85 mmol) in acetonitrile (4 mL). After purification by silica gel column chromatography, eluting dichloromethane/methanol 95:5, the compound (E73) was obtained as an amorphous creamy solid.

Characterization:

$^1$H NMR: (400 MHz, MeOD) δ 8.42 (bs, 1H, H$^{4r}$), 8.33 (d, J=8.0 Hz, 1H, H$^{4r}$), 7.71 (m, 5H, H$^{4r}$), 7.38 (d, J=8.0 Hz, 2H, H$^{4r}$), 7.28 (m, 3H, H$^{4r}$), 6.99 (m, 2H, H$^{4r}$), 6.87 (m, 2H, H$^{4r}$), 5.02 (s, 2H, CH$_2$—O), 4.40 (s, 1H, H$^4$ pip), 3.96 (m, 4H, CH$_2$—O—P), 3.85 (s, 2H, CH$_2$—N), 3.19 (d, J=23.3 Hz, 2H, CH$_2$—P), 2.97 (bs, 2H, H$^2$, H$^6$ pip), 2.68 (bs, 2H, H$^2$, H$^6$ pip), 1.95 (m, 4H, H$^3$, H$^5$ pip), 1.18 (t, J=6.9 Hz, 6H, CH$_3$).

HRMS-ESI (m/z) [M+H]$^+$ calculated for C$_{39}$H$_{42}$F$_3$N$_3$O$_5$P 708.2811, found 708.2809.

Example 74: Synthesis of (E74) 6-[[4-[2-[[4-(diethoxyphosphorylmethyl)phenyl]-methoxy]phenoxy]-1-piperidyl]methyl]-2-[4-(trifluoromethoxy)phenyl]-1H-benzimidazole

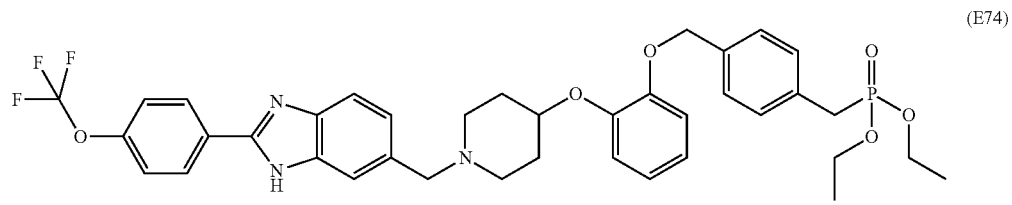 [SMILES: CCOP(=O)(Cc1ccc(COc2ccccc2OC2CCN(Cc3ccc4nc(-c5ccc(OC(F)(F)F)cc5)[nH]c4c3)CC2)cc1)OCC]

(E74)

Procedure:

The title compound (E74) was obtained following the general procedure 12 from compound (38) (36 mg, 1 eq., 0.12 mmol), SOCl$_2$ (244 µL, 29 eq., 3.35 mmol), compound (49) (50 mg, 1 eq., 0.12 mmol), and diisopropylethylamine (104 µL, 5.3 eq., 0.61 mmol) in acetonitrile (2 mL). After purification by silica gel column chromatography, eluting dichloromethane/methanol 95:5, the compound (E74) was obtained as an amorphous creamy solid (17 mg, 23%).

Characterization:

$^1$H NMR: (400 MHz, MeOD) δ 8.17 (d, J=9.0 Hz, 2H, H$^{4r}$), 7.61 (m, 2H, H$^{4r}$), 7.46 (d, J=8.7 Hz, 2H, H$^{4r}$), 7.39 (d, J=7.8 Hz, 2H, H$^{4r}$), 7.30 (m, 3H, H$^{4r}$), 6.99 (m, 2H, H$^{4r}$),

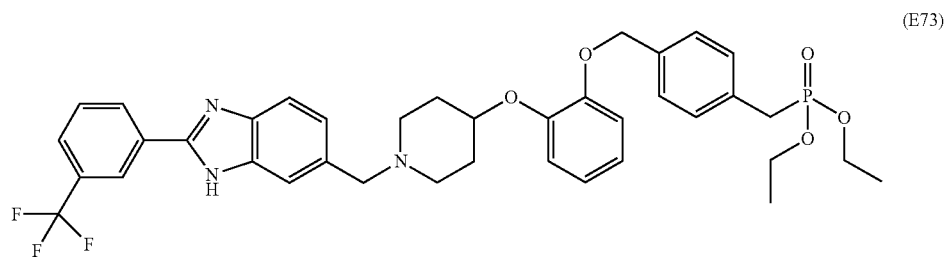

(E73)

6.89 (m, 2H, H$^{Ar}$), 5.02 (s, 2H, CH$_2$—O), 4.40 (s, 1H, H$^4$ pip), 3.99 (dqd, J=9.8, 7.0, 1.6 Hz, 4H, CH$_2$—O—P), 3.80 (s, 2H, CH$_2$—N), 3.21 (d, J=21.9 Hz, 2H, CH$_2$—P), 2.95 (bs, 2H, H$^2$, H$^6$ pip), 2.58 (bs, 2H, H$^2$, H$^6$ pip), 1.92 (m, 4H, H$^3$, H$^5$ pip), 1.21 (t, J=7.1 Hz, 6H, CH$_3$).

$^{13}$C NMR: (101 MHz, MeOD) δ 151.27 (C$^{quat}$), 150.42 (C$^{quat}$), 150.08 (C$^{quat}$), 147.13 (C$^{quat}$) 136.27 (d, J=4.0 Hz, C$^{quat}$) 131.00 (d, J=9.2 Hz, C$^{quat}$) 129.68 (d, J=6.7 Hz, C$^{Ar}$) 128.59 (C$^{Ar}$) 128.33 (C$^{Ar}$), 127.53 (d, J=2.7 Hz, C$^{Ar}$), 125.04 (C$^{Ar}$) 122.29 (C$^{Ar}$) 121.74 (C$^{Ar}$), 121.45 (C$^{Ar}$) 121.18 (C$^{Ar}$) 118.37 (C$^{Ar}$), 115.30 (C$^{Ar}$), 70.50 (CH$_2$—O), 62.30 (d, J=6.9 Hz, CH$_2$—O—P), 62.30 (CH$_2$—N), 49.20 (C$^2$, C$^6$ pip), 31.96 (d, J=137.2 Hz, CH$_2$—P), 29.49 (C3, C$^5$ pip), 15.24 (d, J=6.0 Hz, CH$_3$).

$^{31}$P NMR: (162 MHz, MeOD) δ 27.43.

$^{19}$F NMR: (376 MHz, MeOD) δ −59.34.

HRMS-ESI (m/z) [M+H]$^+$ calculated for C$_{39}$H$_{42}$F$_3$N$_3$O$_6$P 724.2760, found 724.2757.

Example 75: Synthesis of (E75) 6-[[4-[2-[[4-(diethoxyphosphorylmethyl)phenyl]-methoxy]phenoxy]-1-piperidyl]methyl]-2-[3-(trifluoromethoxy)phenyl]-1H-benzimidazole

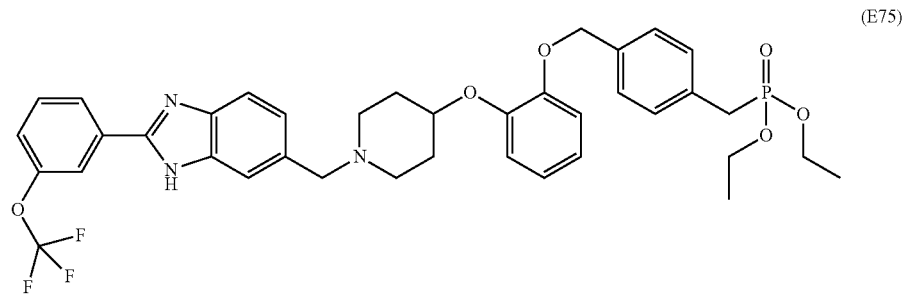 [SMILES: CCOP(=O)(Cc1ccc(COc2ccccc2OC2CCN(Cc3ccc4nc(-c5cccc(OC(F)(F)F)c5)[nH]c4c3)CC2)cc1)OCC]

(E75)

Procedure:

The title compound (E75) was obtained following the general procedure 4 from compound (40) (36 mg, 1 eq., 0.12 mmol), SOCl$_2$ (244 μL, 29 eq., 3.35 mmol), compound (49) (50 mg, 1 eq., 0.12 mmol), and diisopropylethylamine (104 μL, 5.3 eq., 0.61 mmol) in acetonitrile (2 mL). After purification by silica gel column chromatography, eluting dichloromethane/methanol 95:5, the compound (E75) was obtained as an amorphous creamy solid (18 mg, 25%).

Characterization:

$^1$H NMR: (400 MHz, MeOD) δ 8.08 (d, J=8.0 Hz, 1H, H$^{Ar}$), 8.03 (s, 1H, H$^{Ar}$), 7.62 (m, 3H, H$^{Ar}$), 7.41 (m, 3H, H$^{Ar}$), 7.31 (m, 3H, H$^{Ar}$), 6.99 (m, 2H, H$^{Ar}$), 6.88 (m, 2H, H$^{Ar}$), 5.02 (s, 2H, CH$_2$—O), 4.39 (s, 1H, H$^4$ pip), 3.99 (dqd, J=8.0, 7.0, 1.6 Hz, 4H, CH$_2$—O—P), 3.77 (s, 2H, CH$_2$—N), 3.21 (d, J=21.7 Hz, 2H, CH$_2$—P), 2.91 (s, 2H, H$^2$, H$^6$ pip), 2.54 (s, 2H, H$^2$, H$^6$ pip), 1.91 (s, 4H, H$^3$, H$^5$ pip), 1.21 (dt, J=7.0, 0.4 Hz, 6H, CH$_3$).

$^{13}$C NMR: (101 MHz, MeOD) δ 150.88 (C$^{quat}$), 150.06 (C$^{quat}$), 149.71 (d, J=2.0 Hz, 1H, H$^{Ar}$), 147.15 (C$^{quat}$) 136.29 (d, J=3.9 Hz, C$^{quat}$) 131.78 (C$^{Ar}$), 131.00 (d, J=9.5 Hz, C$^{quat}$) 130.69 (C$^{Quat}$), 129.66 (d, J=6.7 Hz, C$^{Ar}$), 127.51 (d, J=3.2 Hz, C$^{Ar}$), 125.01 (C$^{Ar}$) 122.29 (C$^{Ar}$) 122.21 (C$^{Ar}$) 121.82 (Ar), 121.45 (C$^{Ar}$) 119.27 (C$^{Ar}$) 118.92 (C$^{Ar}$) 118.31 (C$^{Ar}$) 115.33 (C$^{Ar}$), 70.50 (CH$_2$—O), 62.43 (CH$_2$—N), 62.31 (d, J=7.0 Hz, CH$_2$—O—P), 49.34 (C$^2$, C$^6$ pip), 32.02 (d, J=138.0 Hz, CH$_2$—P), 29.67 (C3, C$^5$ pip), 15.24 (d, J=6.0 Hz, CH$_3$).

$^{31}$P NMR: (162 MHz, MeOD) δ 27.43.

$^{19}$F NMR: (376 MHz, MeOD) δ −59.35.

HRMS-ESI (m/z) [M+H]$^+$ calculated for C$_{39}$H$_{42}$F$_3$N$_3$O$_6$P 724.2760, found 724.2759.

Example 76: Synthesis of (E76) 6-[[4-[[2-[[4-(diethoxyphosphorylmethyl)phenyl]-methoxy]phenyl]methyl]-1-piperidyl]methyl]-2-phenyl-1H-benzimidazole

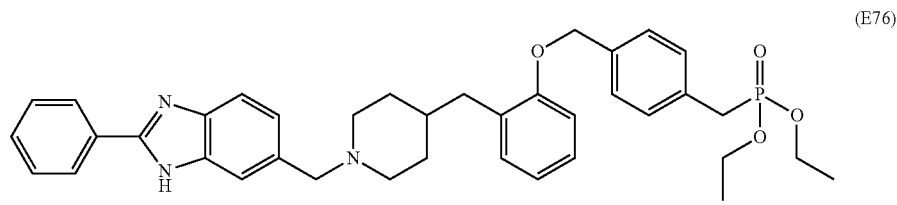 [SMILES: CCOP(=O)(Cc1ccc(COc2ccccc2CC2CCN(Cc3ccc4nc(-c5ccccc5)[nH]c4c3)CC2)cc1)OCC]

(E76)

Procedure:

1. Synthesis of Compound (50) tert-butyl 4-[[2-[[4-(diethoxyphosphorylmethyl)phenyl]-methoxy]phenyl]methyl]piperidine-1-carboxylate

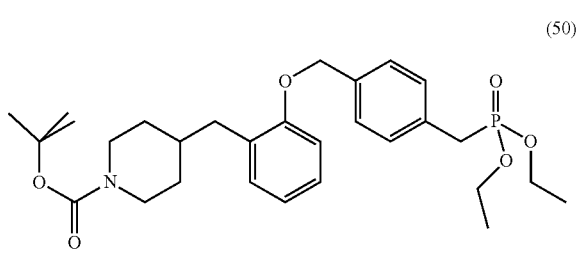 [SMILES: CCOP(=O)(Cc1ccc(COc2ccccc2CC2CCN(C(=O)OC(C)(C)C)CC2)cc1)OCC]
(50)

In a 10-20 mL microwave vial, compound (26) (1.32 mg, 1.5 eq., 4.12 mmol) was dissolved in DMA (20 mL). To this mixture were sequentially added potassium carbonate (760 mg, 2 eq., 5.49 mol), compound (43) (800 mg, 1 eq., 2.45 mmol) and a catalytic amount of sodium iodide (few crystals). This reaction was stirred for 30 min at 140° C. under microwave irradiation, and the obtained solution was dissolved in water (20 mL) and diethyl ether (100 mL). The aqueous phase was then extracted twice ethyl acetate (2×50 mL), and the organic phase washed 5 times with water (5×40 mL), once with brine (40 mL), dried over MgSO$_4$ and evaporated. The residue was consequently purified by column chromatography (dichloromethane/methanol 99:1) to afford compound (50) as a white solid (920 mg, 71% of conversion).

2. Synthesis of Compound (51) 4-[[2-[[4-(diethoxyphosphorylmethyl)phenyl]-methoxy]phenyl]methyl]piperidine

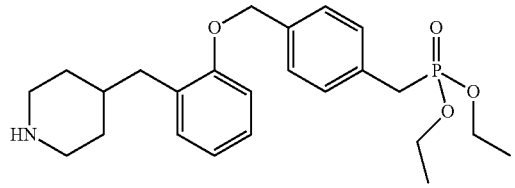
(51)

Following general procedure 11, trifluoroacetic acid (7.2 mL, 100 eq., 94.0 mmol) was added to a solution of compound (50) (500 mg, 1 eq., 0.94 mmol) in dichloromethane (15 mL). Pure compound (51) was obtained after flash column chromatography (dichloromethane/ethanol 95:5), and compound (52) was obtained as a light brown solid (356 mg, 88%).

3. Synthesis of Compound (E76)

The title compound (E76) was obtained following the general procedure 12 from compound (3) (26 mg, 1 eq., 0.12 mmol), SOCl$_2$ (246 μL, 29 eq., 3.37 mmol), compound (51) (50 mg, 1 eq., 0.12 mmol), and diisopropylethylamine (105 μL, 5.3 eq., 0.61 mmol) in acetonitrile (3 mL). After purification by silica gel column chromatography, eluting dichloromethane/methanol 95:5, the title compound (E76) was obtained as an amorphous creamy solid (13 mg, 18%).

Characterization:

$^1$H NMR: (400 MHz, MeOD) δ 8.11 (dd, J=8.0, 2.0 Hz, 2H, H$^{Ar}$), 7.65 (m, 2H, H$^{Ar}$), 7.57 (m, 3H, H$^{Ar}$), 7.42 (d, J=7.8 Hz, 2H, H$^{Ar}$), 7.33 (m, 3H, H$^{Ar}$), 7.16 (dt, J=8.4, 1.6 Hz, 1H), 7.10 (dd, J=7.3, 1.6 Hz, 1H, H$^{Ar}$), 6.98 (d, J=8.4 Hz, 1H, H$^{Ar}$), 6.86 (t, J=7.4 Hz, 1H, H$^{Ar}$), 5.08 (s, 2H, CH$_2$—O), 4.02 (m, 6H, CH$_2$—O—P, CH$_2$—N), 3.25 (d, J=21.2 Hz, 2H, CH$_2$—P), 3.18 (bd, J=12.1 Hz, 2H, H$^2$, H$^6$ pip), 2.64 (d, J=6.7 Hz, 2H, CH$_2$), 2.47 (bs, 2H, H$^2$, H$^6$ pip), 1.82 (m, 1H, H$^4$ pip), 1.74 (bd, J=14.5 Hz, 2H, H$^3$, H$^5$ pip), 1.45 (dq, J=11.2, 2.7 Hz, 2H, H$^3$, H$^5$ pip), 1.24 (t, J=7.1 Hz, 6H, CH$_3$).

$^{13}$C NMR: (101 MHz, MeOD) δ 156.62 (C$^{quat}$—CH$_2$), 153.11 (C$^{quat}$), 136.42 (d, J=4.3 Hz, C$^{quat}$) 130.93 (d, J=9.2 Hz, C$^{quat}$) 130.57 (C$^{Ar}$) 130.24 (C$^{Ar}$), 129.72 (d, J=6.4 Hz, C$^{Ar}$) 129.38 (C$^{Ar}$) 128.81 (C$^{Ar}$) 128.30 (C$^{Ar}$), 127.26 (d, J=3.2 Hz, C$^{Ar}$) 128.29 (C$^{Ar}$) 127.13 (C$^{Ar}$) 126.49 (C$^{Ar}$), 120.25 (C$^{Ar}$) 111.74 (C$^{Ar}$), 69.26 (CH$_2$—O), 62.30 (d, J=7.3 Hz, CH$_2$—O—P), 61.89 (CH$_2$—N), 52.69 (C$^2$, C$^6$ pip), 36.24 (CH$_2$), 35.25 (C$^4$ pip), 31.88 (d, J=138.1 Hz, CH$_2$—P), 30.13 (C$^3$, C$^5$ pip), 15.24 (d, J=6.0 Hz, CH$_3$).

$^{31}$P NMR: (162 MHz, MeOD) δ 27.27.

HRMS-ESI (m/z) [M+H]$^+$ calculated for C$_{39}$H$_{47}$N$_3$O$_3$P 638.3146, found 638.3144.

Example 77: Synthesis of (E77) 6-[[4-[[2-[[4-(diethoxyphosphorylmethyl)phenyl]-methoxy]phenyl]methyl]-1-piperidyl]methyl]-2-[4-(trifluoromethyl)phenyl]-1H-benzimidazole

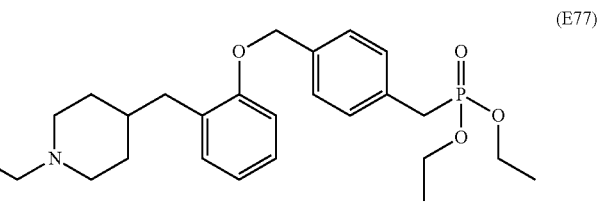
(E77)

Procedure:

The title compound (E77) was obtained following the general procedure 12 from compound (12) (41 mg, 1 eq., 0.14 mmol), SOCl$_2$ (296 μL, 29 eq., 4.06 mmol), compound

(51) (60 mg, 1 eq., 0.14 mmol), and diisopropylethylamine (116 μL, 5.3 eq., 0.70 mmol) in acetonitrile (3 mL). After purification by silica gel column chromatography, eluting dichloromethane/methanol 95:5, the compound (E77) was obtained as an amorphous creamy solid (13 mg, 15%).

Characterization:

$^1$H NMR: (250 MHz, MeOD) δ 8.45 (s, 1H, $H^{4r}$), 8.36 (d, J=7.6 Hz, 1H, $H^{4r}$), 7.75 (m, 4H, $H^{4r}$), 7.35 (m, 5H, $H^{4r}$), 7.10 (m, 2H, $H^{4r}$), 6.96 (dd, J=8.2, 0.9 Hz, 1H, $H^{4r}$), 6.83 (dt, J=7.2, 1.0 Hz, 1H, $H^{4r}$), 5.04 (s, 2H, $CH_2$—O), 4.35 (s, 2H, $CH_2$—N), 3.99 (dqd, J=8.6, 7.1, 0.5 Hz, 4H, $CH_2$—O—P), 3.39 (bd, J=12.0 Hz, 2H, $H^2$, $H^6$ pip), 3.21 (d, J=21.6 Hz, 2H, $CH_2$—P), 2.92 (bt, J=12.0 Hz, 2H, $H^2$, $H^6$ pip), 2.63 (d, J=6.2 Hz, 2H, $CH_2$), 1.92 (m, 1H, $H^4$ pip), 1.81 (bd, J=14.7 Hz, 2H, $H^3$, $H^5$ pip), 1.55 (m, 2H, $H^3$, $H^5$ pip), 1.20 (td, J=7.0, 0.5 Hz, 6H, $CH_3$).

HRMS-ESI (m/z) [M+H]$^+$ calculated for $C_{39}H_{44}F_3N_3O_4P$ 706.3022, found 706.3017.

Example 78: Synthesis of (E78) 6-[[4-[[2-[[4-(di-ethoxyphosphorylmethyl)phenyl]methoxy]phenyl]methyl]-1-piperidyl]methyl]-2-[3-(trifluoromethyl)phenyl]-1H-benzimidazole

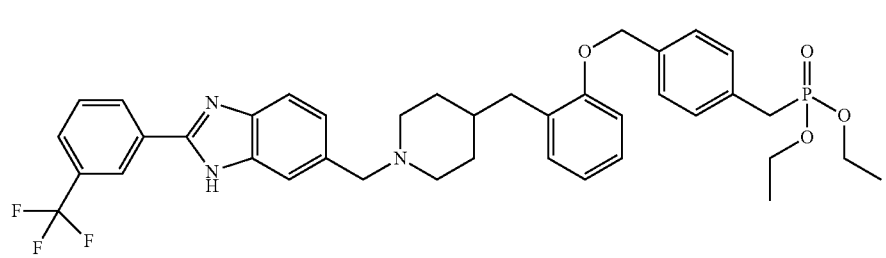

(E78)

Procedure:

The title compound (E78) was obtained following the general procedure 12 from benzimidazole (14) (41 mg, 1 eq., 0.14 mmol), SOCl$_2$ (296 μL, 29 eq., 4.06 mmol,) compound (51) (60 mg, 1 eq., 0.14 mmol), and diisopropylethylamine (116 μL, 5.3 eq., 0.70 mmol) in acetonitrile (3 mL). After purification by silica gel column chromatography, eluting dichloromethane/methanol 95:5, the title compound (E78) was obtained as an amorphous creamy solid (16 mg, 18%).

Characterization:

$^1$H NMR: (250 MHz, MeOD) δ 8.44 (s, 1H, $H^{4r}$), 8.36 (d, J=8.8 Hz, 1H, $H^{4r}$), 7.96 (s, 1H, $H^{4r}$), 7.75 (m, 5H, $H^{4r}$), 7.53 (d, J=7.5 Hz, 1H, $H^{4r}$), 7.44 (s, 1H, $H^{4r}$), 7.32 (m, 2H, $H^{4r}$) 7.18 (d, J=7.6 Hz, 1H, $H^{4r}$), 7.08 (m, 1H, $H^{4r}$), 6.81 (t, J=8.1 Hz, 1H, $H^{4r}$), 4.96 (s, 2H, $CH_2$—O), 4.63 (s, 2H, $CH_2$—N), 3.97 (dqd, J=9.2, 7.0, 1.1 Hz, 4H, $CH_2$—O—P), 3.13 (m, 2H, $H^2$, $H^6$ pip), 3.06 (d, J=21.4 Hz, 2H, $CH_2$—P), 2.67 (d, J=7.6 Hz, 2H, $CH_2$), 2.13 (m, 2H, $H^2$, $H^6$ pip), 1.85 (bd, J=13.4 Hz, 2H, $H^3$, $H^5$ pip), 1.75 (m, 1H, $H^4$ pip), 1.44 (m, 2H, $H^3$, $H^5$ pip), 1.12 (dt, J=7.3, 0.6 Hz, 6H, $CH_3$).

HRMS-ESI (m/z) [M+H]$^+$ calculated for $C_{39}H_{44}F_3N_3O_4P$ 706.3022, found 706.3019.

Example 79: Synthesis of (E79) 6-[[4-[[2-[[4-(di-ethoxyphosphorylmethyl)phenyl]-methoxy]phenyl]methyl]-1-piperidyl]methyl]-2-[4-(trifluoromethoxy)phenyl]-3a,7a-dihydro-1H-benzimidazole

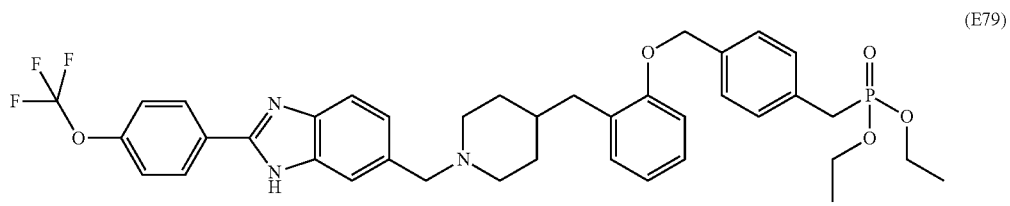 [SMILES: CCOP(=O)(Cc1ccc(COc2ccccc2CC2CCN(Cc3ccc4nc(-c5ccc(OC(F)(F)F)cc5)[nH]c4c3)CC2)cc1)OCC]

(E79)

Procedure:

The title compound (E79) was obtained following the general procedure 12 from compound (38) (43 mg, 1 eq., 0.14 mmol), SOCl$_2$ (296 μL, 29 eq., 4.06 mmol), compound (51) (60 mg, 1 eq., 0.14 mmol), and diisopropylethylamine (116 μL, 5.3 eq., 0.70 mmol) in acetonitrile (3 mL). After purification by silica gel column chromatography, eluting dichloromethane/methanol 95:5, the title compound (E79) was obtained as an amorphous creamy solid (20 mg, 21%).

Characterization:

$^1$H NMR: (250 MHz, MeOD) δ 8.21 (d, J=9.3 Hz, 2H, $H^{4r}$), 7.78 (s, 1H, $H^{4r}$), 7.68 (s, 1H, $H^{4r}$), 7.46 (d, J=8.7 Hz, 2H, $H^{4r}$), 7.39 (s, 1H, $H^{4r}$), 7.32 (m, 4H, $H^{4r}$), 7.11 (m, 2H, $H^{4r}$) 6.97 (d, J=7.5 Hz, 1H, $H^{4r}$), 6.83 (td, J=7.1, 0.6 Hz, 1H, $H^{4r}$), 5.05 (s, 2H, $CH_2$—O), 4.37 (s, 2H, $CH_2$—N), 3.99 (dqd, J=8.8, 7.1, 0.6 Hz, 4H, $CH_2$—O—P), 3.42 (m, 2H, $H^2$, $H^6$ pip), 3.21 (d, J=21.1 Hz, 2H, $CH_2$—P), 2.94 (bs, 2H, $H^2$, $H^6$ pip), 2.61 (d, J=5.7 Hz, 2H, $CH_2$), 1.95 (m, 1H, $H^4$ pip), 1.82 (bd, J=15.8 Hz, 2H, $H^3$, $H^5$ pip), 1.53 (m, $H^3$, $H^5$ pip), 1.20 (dt, J=7.1, 0.5 Hz, 6H, $CH_3$).

HRMS-ESI (m/z) [M+H]$^+$ calculated for $C_{39}H_{44}F_3N_3O_5P$ 722.2971, found 722.2966.

Example 80: Synthesis of (E80) 6-[[4-[[2-[[4-(diethoxyphosphorylmethyl)phenyl]-methoxy]phenyl]methyl]-1-piperidyl]methyl]-2-[3-(trifluoromethoxy)phenyl]-1H-benzimidazole (E80)

Procedure:

The title compound (E80) was obtained following the general procedure 12 from compound (40) (43 mg, 1 eq., 0.14 mmol), SOCl$_2$ (296 µL, 29 eq., 4.06 mmol), compound (51) (60 mg, 1 eq., 0.14 mmol), and diisopropylethylamine (116 µL, 5.3 eq., 0.70 mmol) in acetonitrile (3 mL). After purification by silica gel column chromatography, eluting dichloromethane/methanol 95:5, the clean compound (E80) was obtained as an amorphous creamy solid (16 mg, 17%).

Characterization:

$^1$H NMR: (400 MHz, MeOD) δ 8.11 (d, J=8.9 Hz, 1H, H$^{Ar}$), 8.04 (s, 1H, H$^{Ar}$), 7.66 (m, 3H, H$^{Ar}$), 7.45 (m, 2H, H$^{Ar}$), 7.32 (m, 2H, H$^{Ar}$), 7.21 (m, 2H, H$^{Ar}$), 7.09 (m, 2H, H$^{Ar}$), 6.91 (d, J=8.8 Hz, 1H, H$^{Ar}$), 6.82 (t, J=7.6 Hz, 1H, H$^{Ar}$), 4.98 (s, 2H, CH$_2$—O), 4.63 (s, 2H, CH$_2$—N), 3.92 (dqd, J=9.3, 7.2, 1.0 Hz, 4H, CH$_2$—O—P), 3.58 (m, 2H, H$^2$, H$^6$ pip), 3.07 (d, J=21.4 Hz, 2H, CH$_2$—P), 2.94 (bs, 2H, H$^2$, H$^6$ pip), 2.68 (d, J=5.8 Hz, 2H, CH$_2$), 2.09 (m, 2H, H$^2$, H$^6$ pip), 1.82 (bd, J=13.4 Hz, 2H, H$^3$, H$^5$ pip), 1.74 (m, 1H, H$^4$ pip), 1.6 (m, 2H, H$^3$, H$^5$ pip), 1.13 (dt, J=7.0, 0.3 Hz, 6H, CH$_3$).

HRMS-ESI (m/z) [M+H]$^+$ calculated for C$_{39}$H$_{44}$F$_3$N$_3$O$_5$P 722.2971, found 722.2967.

Example 81: Antiviral Evaluation of the Synthesized Molecules

Some of the synthesized compounds were screened using a virus infection assay following a published procedure (Lee, K.; Ren, T.; Côté, M.; Gholamreza, B.; Misasi, J.; Bruchez, A.; Cunningham, J., Inhibition of Ebola virus infection: Identification of Niemann-Pick C1 as the target by optimization of a chemical probe. ACS Med. Chem. Lett. 2013, 4, 239-243 (Supporting Information)).

Cell Culture, Virus Production and Measurement of Infection

Vero and 293T cells were cultured in DMEM (Invitrogen) supplemented with penicillin/streptomycin (1000 U/ml), L-glutamine (2 mM, Invitrogen), FBS (5%) and FetalPlex (5%, Gemini).

CHO$_{null}$ (Chinese hamster ovary fibroblasts lacking NPC1) and CHO$_{NPC1}$ (Chinese hamster ovary fibroblasts expressing NPC1) cells were cultured in equal mixture of F12 and DMEM media (Invitrogen) with penicillin/streptomycin, L-glutamine (Invitrogen) and FBS.

Ectodomain of Ebola Virus glycoprotein (EboV GP) was produced in 293T cells.

Vesicular stomatitis virus (VSV) particles encoding luciferase and pseudotyped with EboV GP, Lassa fever virus GP or VSV GP were produced in 293T cells.

Virus infection assays were performed in 384-well plate format using luciferase reporter.

Vesicular Stomatitis Virus (VSV) pseudotyped viruses expressing Green Fluorescent Protein (GFP), which are replicon models of EBoV, were added to cells in serial 10-fold dilutions and assayed using fluorescence microscopy.

An infectious unit (i.u.) was defined as one GFP-expressing cell within a range where the change in GFP-positive cells is directly proportional to the virus dilution.

For VSV expressing the luciferase reporter, pseudotyped virus was added to cells and luciferase activity was assayed during 6 to 20 hours post-infection using the firefly luciferase kit (Promega).

Signal was measured in relative luminescence units (RLU) using an EnVison plate reader (Perkin Elmer).

In experiments involving inhibitors, stock solutions of 20 mM or 10 mM in DMSO were diluted to obtain a final concentration of 1% DMSO in media.

Inhibitory activity was stable in the media of cultured cells for more than 72 hours as assessed using a single cycle entry assay.

Infection of target cells with LacZ-encoding retroviral pseudotypes was performed in the presence of 5 µg/ml polybrene (Sigma).

72 hours post-infection, cells were stained for LacZ activity and titer was determined by counting positive foci and expressed as focus forming units (FFU) per ml of virus.

Two different concentrations of compounds were evaluated, 2 and 10 µM. In the table are presented results for the compounds which have been evaluated.

| Compound | Inhibition (%) | |
|---|---|---|
| | 10 µM | 2 µM |
| (E11) | 95 | |
| (E14) | 80 | |
| (E15) | 93.5 | 2 |
| (E16) | 91.6 | 64.1 |
| (E17) | <20 | |
| (E18) | <20 | |
| (E19) | <20 | |
| (E20) | <20 | |
| (E22) | 80 | <20 |
| (E29) | 80 | <20 |
| (E52) | 82.9 | 64.3 |
| (E57) | <20 | |

-continued

| Compound | Inhibition (%) | |
|---|---|---|
| | 10 µM | 2 µM |
| (E58) | 98 | |
| (E59) | <20 | |
| (E60) | 98 | |

The compounds evaluated for their Ebola virus inhibition show good results. Indeed, some compounds evaluated can inhibit Ebola virus with an inhibition rate higher than 80% and some of them, higher than 95%. Even the compounds less active, they show an inhibition rate (with a compound concentration of 10 µM) of about 20%. This inhibition rate shows that all the compounds evaluated show a Ebola virus inhibition activity.

The invention claimed is:

1. A compound of formula (I):

$$(I)$$

wherein:
X represents:
  a C=O group;
  an alkyl group, linear or branched, comprising 1 to 6 carbon atoms; or
  a group of formula —NR—$(C_1-C_6)$alkyl-, the alkyl being linear or branched;
Y represents CH or nitrogen atom;
$R^1$ represents:
  an aryl group, comprising 6 to 10 carbon atoms, non-substituted or substituted by at least one group selected from the group consisting of: haloalkyl, haloalkoxyl, and an alkyl or alkoxyl group, the alkyl being linear or branched, and comprising 1 to 6 carbon atoms;
  an heteroaryl group, comprising 6 to 10 members, non-substituted or substituted by at least one group selected from the group consisting of: haloalkyl, haloalkoxyl, and an alkyl or alkoxyl group, the alkyl being linear or branched, and comprising 1 to 6 carbon atoms;
  a CH-(aryl)$_2$ group, the aryl comprising 6 to 10 carbon atoms, non-substituted or substituted by at least one group selected from the group consisting of: haloalkyl, haloalkoxyl, and an alkyl or alkoxyl group, the alkyl being linear or branched, and comprising 1 to 6 carbon atoms; or
  a CH-(heteroaryl)$_2$ group, the heteroaryl comprising 6 to 10 members, non-substituted or substituted by at least one group selected from the group consisting of: haloalkyl, haloalkoxyl, alkyl or alkoxyl group, the alkyl being linear or branched, and comprising 1 to 6 carbon atoms;
$R^2$ represents:
  a $(C_1-C_6)$alkyl-aryl-$R^3$ group, the aryl comprising 6 to 10 carbon atoms and the alkyl being linear or branched;
  a C(O)N(R)-aryl-$R^5$ group, the aryl comprising between 6 to 10 carbon atoms;
  a C(O)—$(C_1-C_6)$alkyl-O-aryl-Hal group, with Hal represents an halogen, the aryl comprising between 6 and 10 carbon atoms and the alkyl being linear or branched;
  a C(O)O—$(C_1-C_6)$alkyl-aryl group, the aryl comprising between 6 to 10 carbon atoms and the alkyl being linear or branched; or
  a O-aryl-IV group, the aryl comprising between 6 to 10 carbon atoms;
$R^3$ represents a $OR^4$ group, haloalkyl or haloalkoxyl, wherein the alkyl is linear or branched, and comprises 1 to 6 carbon atoms;
$R^4$ represents a $(C_1-C_6)$alkyl-aryl-COOR group, a haloalkyl group or a $(C_1-C_6)$alkyl-aryl-$(C_1-C_6)$alkyl-PO$(OR)_2$ group, wherein alkyl is linear or branched and comprises 1 to 6 carbon atoms and the aryl comprises between 6 and 10 carbon atoms;
$R^5$ represents an alkyl group, linear or branched, comprising 1 to 6 carbon atoms; or a haloalkyl, linear or branched, comprising 1 to 6 carbon atoms;
R represents an alkyl group, linear or branched, comprising 1 to 6 carbon atoms, or a hydrogen atom;
or their pharmaceutically acceptable salts, hydrates, solvates, esters or their optical isomers, racemates, diastereoisomers, enantiomers, tautomers, or a mixture thereof.

2. The compound according to claim 1 for which $R^1$ is selected from the group consisting of:
  a phenyl group, non-substituted or substituted by at least one group selected from the group consisting of: haloalkyl, haloalkoxyl, alkyl or alkoxyl group, the alkyl being linear or branched, and comprising 1 to 6 carbon atoms;
  a pyridine group non-substituted or substituted by at least one group selected from the group consisting of: haloalkyl, haloalkoxyl, alkyl or alkoxyl group, the alkyl being linear or branched, and comprising 1 to 6 carbon atoms;
  a pyrimidine group, non-substituted or substituted by at least one group selected from the group consisting of: haloalkyl, haloalkoxyl, alkyl or alkoxyl group, the alkyl being linear or branched, and comprising 1 to 6 carbon atoms; and
  a benzhydryl group non-substituted or substituted by at least one group selected from the group consisting of: haloalkyl, haloalkoxyl, alkyl or alkoxyl group, the alkyl being linear or branched, and comprising 1 to 6 carbon atoms.

3. The compound according to claim 1 for which R' is selected from the group consisting of:
  a phenyl group non-substituted or substituted by at least one group selected from the group consisting of: fluoroalkyl, fluoroalkoxyl, alkyl or alkoxyl group, the alkyl being linear or branched, and comprising 1 to 6 carbon atoms;
  a pyridine group non-substituted or substituted by at least one group selected from the group consisting of: haloalkyl, haloalkoxyl, alkyl or alkoxyl group, the alkyl being linear or branched, and comprising 1 to 6 carbon atoms; and
  a benzhydryl group non-substituted or substituted by at least one group selected from the group consisting of: fluoroalkyl, fluoroalkoxyl, alkyl or alkoxyl group, the alkyl being linear or branched, and comprising 1 to 6 carbon atoms.

4. The compound according to claim 1 for which X represents:
   a (C=O) group; or
   an alkyl group, linear or branched, comprising 1 to 3 carbon atoms.

5. The compound according to claim 1 for which Y represents a CH group.

6. The compound according to claim 1 for which Y represents a nitrogen atom.

7. A pharmaceutical composition comprising at least one compound of formula (I) according to claim 1 as active principle, and optionally a pharmaceutically acceptable excipient.

8. A method of treating a viral disease comprising administering to a patient in need thereof an effective amount of the compound of formula (I) according to claim 1.

9. A method of treating a filovirus infection comprising administering to a patient in need thereof an effective amount of the compound according to claim 1.

10. A method of treating an Ebola virus infection comprising administering to a patient in need thereof an effective amount of the compound according to claim 1.

11. A method of treating a retrovirus infection comprising administering to a patient in need thereof an effective amount of the compound according to claim 1.

12. A method of treating a Human Immunodeficiency Virus (HIV) infection comprising administering to a patient in need thereof an effective amount of the compound according to claim 1.

13. A method of treating a pathology selected from the group consisting of a cholesterol disorder, a metabolic disorder, obesity, AIDS, congenital disease, genetic disease, and Niemann-Pick disease type C1 comprising administering to a patient in need thereof an effective amount of the compound according to claim 1.

14. A method of treating a viral disease comprising administering to a patient in need thereof an effective amount of the pharmaceutical composition according to claim 7.

15. A method of treating a filovirus infection comprising administering to a patient in need thereof an effective amount of the pharmaceutical composition according to claim 7.

16. A method of treating an Ebola virus infection comprising administering to a patient in need thereof an effective amount of the pharmaceutical composition according to claim 7.

17. A method of treating a retrovirus infection comprising administering to a patient in need thereof an effective amount of the pharmaceutical composition according to claim 7.

18. A method of treating a Human Immunodeficiency Virus (HIV) infection comprising administering to a patient in need thereof an effective amount of the pharmaceutical composition according to claim 7.

19. A method of treating a pathology selected from the group consisting of a cholesterol disorder, a metabolic disorder, obesity, AIDS, congenital disease, genetic disease, and Niemann-Pick disease type C1 comprising administering to a patient in need thereof an effective amount of the pharmaceutical composition according to claim 7.

* * * * *